US010675332B1

(12) United States Patent
Chen et al.

(10) Patent No.: US 10,675,332 B1
(45) Date of Patent: Jun. 9, 2020

(54) RECOMBINANT POLYPEPTIDES AND METHODS OF USE THEREOF

(71) Applicant: Imunami Laboratories Pte. Ltd., Singapore (SG)

(72) Inventors: Ya-Huei Chen, Singapore (SG); Ting-long Lin, Singapore (SG)

(73) Assignee: Imunami Laboratories Pte. Ltd., Singapore (SG)

( * ) Notice: Subject to any disclaimer, the term of this patent is extended or adjusted under 35 U.S.C. 154(b) by 0 days.

(21) Appl. No.: 16/551,659

(22) Filed: Aug. 26, 2019

(51) Int. Cl.
| A61K 38/21 | (2006.01) |
| A61K 38/17 | (2006.01) |
| A61P 35/04 | (2006.01) |
| A61K 9/00  | (2006.01) |
| A61P 35/00 | (2006.01) |

(52) U.S. Cl.
CPC .......... *A61K 38/217* (2013.01); *A61K 9/0019* (2013.01); *A61K 38/1703* (2013.01); *A61P 35/00* (2018.01); *A61P 35/04* (2018.01)

(58) Field of Classification Search
None
See application file for complete search history.

(56) References Cited

U.S. PATENT DOCUMENTS

| 4,579,821 A | 4/1986 | Palmiter et al. |
| 4,599,311 A | 7/1986 | Kawasaki |
| 4,601,978 A | 7/1986 | Karin |
| 4,615,974 A | 10/1986 | Kingsman et al. |
| 4,656,134 A | 4/1987 | Ringold |
| 4,661,454 A | 4/1987 | Botstein et al. |
| 4,713,339 A | 12/1987 | Levinson et al. |
| 4,784,950 A | 11/1988 | Hagen et al. |
| 4,845,075 A | 7/1989 | Murray et al. |
| 4,870,008 A | 9/1989 | Brake |
| 4,882,279 A | 11/1989 | Cregg |
| 4,931,373 A | 6/1990 | Kawasaki et al. |
| 4,935,349 A | 6/1990 | McKnight et al. |
| 4,956,288 A | 9/1990 | Barsoum |
| 4,977,092 A | 12/1990 | Bitter |
| 4,990,446 A | 2/1991 | Oberto et al. |
| 5,037,743 A | 8/1991 | Welch et al. |
| 5,063,154 A | 11/1991 | Fink et al. |
| 5,139,936 A | 8/1992 | Botstein et al. |
| 5,143,830 A | 9/1992 | Holland et al. |
| 5,162,222 A | 11/1992 | Guarino et al. |
| 5,162,228 A | 11/1992 | Sumino et al. |
| 5,300,435 A | 4/1994 | Granados |
| 5,716,808 A | 2/1998 | Raymond |
| 5,736,383 A | 4/1998 | Raymond |
| 5,854,039 A | 12/1998 | Raymond et al. |
| 5,888,768 A | 3/1999 | Raymond |
| 9,701,713 B2 | 7/2017 | Petrash et al. |
| 10,150,801 B1 | 12/2018 | Chen et al. |
| 10,301,364 B1 | 5/2019 | Chen et al. |
| 10,323,071 B1 | 6/2019 | Chen et al. |
| 10,351,607 B1 | 7/2019 | Chen et al. |
| 10,370,421 B2 | 8/2019 | Chen et al. |
| 2014/0017203 A1 | 1/2014 | Choi et al. |
| 2019/0315818 A1 | 10/2019 | Chen et al. |

FOREIGN PATENT DOCUMENTS

| WO | WO 94/06463 A1 | 3/1994 |
| WO | WO 2012/099448 A2 | 7/2012 |
| WO | WO 2012/135575 A2 | 10/2012 |
| WO | WO 2013/174510 A1 | 11/2013 |

OTHER PUBLICATIONS

Andley, U. P. et al., "Differential Protective Activity of αA- and αB-crystallin in Lens Epithelial Cells," The Journal of Biological Chemistry, vol. 275, No. 47, pp. 36823-36831 (2000).

Basu, S. et al., "Calreticulin, a Peptide-binding Chaperone of the Endoplasmic Reticulum, Elicits Tumor- and Peptide-specific Immunity," J. Exp. Med., vol. 189, No. 5, pp. 797-802 (1999).

Basu, S. et al., "CD91 Is a Common Receptor for Heat Shock Proteins gp96, hsp90, hsp70, and Calreticulin," Immunity, vol. 14, pp. 303-313 (2001).

Binder, R. J. et al., "Peptides chaperoned by heat-shock proteins are a necessary and sufficient source of antigen in the cross-priming of CD8+ T cells," Nature Immunology, vol. 6, No. 6, pp. 593-599 (2005).

Blay, J.-Y. et al., "Early Lymphopenia After Cytotoxic Chemotherapy as a Risk Factor for Febrile Neutropenia," Journal of Clinical Oncology, vol. 14, No. 2, pp. 636-643 (1996).

Bonning, B. C. et al., "Superior expression of juvenile hormone esterase and β-galactosidase from the basic protein promoter of Autographa californica nuclear polyhedrosis virus compared to the p10 protein and polyhedrin promoters," Journal of General Virology, 75, pp. 1551-1556 (1994).

Campbell, A. C. et al., "Characteristics of the lymphopenia induced by radiotherapy," Clin. exp. Immunol., 23, pp. 200-208 (1976).

Carreno, B. M. et al., "A dendritic cell vaccine increases the breadth and diversity of melanoma neoantigen-specific T cells," Science, vol. 348, No. 6239, pp. 803-808 (2015) and Supplementary Materials, 27 pages.

Chazenbalk, G. D. et al., "Expression of the Extracellular Domain of the Thyrotropin Receptor in the Baculovirus System Using a Promoter Active Earlier than the Polyhedrin Promoter," The Journal of Biological Chemistry, vol. 270, No. 4, pp. 1543-1549 (1995).

Corsaro, C. M. et al., "Enhancing the Efficiency of DNA-Mediated Gene Transfer in Mammalian Cells," Somatic Cell Genetics, vol. 7, No. 5, pp. 603-616 (1981).

Davila, M. L. et al., "Efficacy and Toxicity Management of 19-28z CAR T Cell Therapy in B Cell Acute Lymphoblastic Leukemia," Sci Transl Med., 6(224):224ra25, 10 pages; doi: 10.1126/scitranslmed.3008226.

(Continued)

*Primary Examiner* — G Steven Vanni
(74) *Attorney, Agent, or Firm* — Cooley LLP; Matthew Pavao

(57) ABSTRACT

The present disclosure provides methods of preventing, delaying the progression of, treating or alleviating a symptom of, or otherwise ameliorating cancer in a subject by administering a recombinant polypeptide and an agent that reduces IL-10 to a subject in need thereof.

28 Claims, 44 Drawing Sheets
Specification includes a Sequence Listing.

(56) References Cited

OTHER PUBLICATIONS

Drocourt, D. et al., "Cassettes of the Streptoalloteichus hindustanus ble gene for transformation of lower and higher eukaryotes to phleomycin resistance," Nucleic Acids Research, vol. 18, No. 13, p. 4009 (1990).
Evans, S. S. et al., "Fever and the thermal regulation of immunity: the immune system feels the heat," Nature Reviews Immunology, 15:335-349 (2015).
Franĕk, F. et al., "Protection of B lymphocyte hybridoma against starvation-induced apoptosis: survival-signal role of some amino acids," Immunology Letters, 52, pp. 139-144 (1996).
Gatignol, A. et al., "Phleomycin resistance encoded by the ble gene from transposon Tn 5 as a dominant selectable marker in *Saccharomyces cerevisiae*," Mol. Gen. Genet., 207, pp. 342-348 (1987).
GenBank Accession No. AAA28635.1, Jun. 10, 2016.
GenBank Accession No. AAA28637.1, Jun. 10, 2016.
GenBank Accession No. AAH69528.1, Jul. 15, 2006.
GenBank Accession No. O12984.1, Feb. 28, 2018.
GenBank Accession No. P02505.1, Oct. 25, 2017.
GenBank Accession No. Q05557.1, Feb. 28, 2018.
GenBank Accession No. XP013036875.1, Jul. 24, 2015.
GenBank Accession No. XP013042703.1, Jul. 24, 2015.
Gerweck, L. E. et al., "Cellular pH Gradient in Tumor versus Normal Tissue: Potential Exploitation for the Treatment of Cancer," Cancer Research, 56, pp. 1194-1198 (1996).
Giavridis, T. et al., "CAR T cell-induced cytokine release syndrome is mediated by macrophages and abated by IL-1 blockade," Nature Medicine, 24(731-738 (2018), and Methods and Reporting Summaries, 6 pages.
Gillies, R. J. et al., "Evolutionary dynamics of carcinogens and why targeted therapy does not work," Nature Reviews, vol. 12, pp. 487-493 (2012).
Gleeson, M. A. et al., "Transformation of the Methylotrophic Yeast *Hansenula polymorpha*," Journal of General Microbiology, 132, pp. 3459-3465 (1986).
Graham, F. L. et al., "A New Technique for the Assay of Infectivity of Human Adenovirus 5 DNA," Virology, 52, pp. 456-467 (1973).
Hill-Perkins, M. S. et al., "A baculovirus expression vector derived from the basic protein promoter of Autographa californica nuclear polyhedrosis virus," Journal of General Virology, 71, pp. 971-976 (1990).
Ingolia, T. D. et al., "Four small *Drosophila* heat shock proteins are related to each other and to mammalian α-crystallin," Proc. Natl. Acad. Sci. USA, vol. 79, pp. 2360-2364 (1982).
Ishii, T. et al., "Isolation of MHC Class I-Restricted Tumor Antigen Peptide and its Precursors Associated with Heat Shock Proteins hsp70, hsp90, and gp96," J. Immunol., 162, pp. 1303-1309 (1999).
Jolles, C. J. et al., "Systemic immunosuppression induced by peritoneal photodynamic therapy," Am. J. Obstet. Gynecol., vol. 158, No. 6, Part 1, pp. 1446-1452 (1988).
Krysko, D. V. et al., "Immunogenic cell death and DAMPs in cancer therapy," Nature Reviews, vol. 12, pp. 860-875 (2012).
Li, Y. et al., "Selective killing of cancer cells by β-lapachone: Direct checkpoint activation as a strategy against cancer," PNAS, vol. 100, No. 5, pp. 2674-2678 (2003).
Li, R. et al., "αA-crystallin and αB-crystallin, newly identified interaction proteins of protease-activated receptor-2, rescue astrocytes from C2-ceramide- and staurosporine-induced cell death," J. Neurochem, vol. 110, pp. 1433-1444 (2009).
Luckow, V. A. et al., "Efficient Generation of Infectious Recombinant Baculoviruses by Site-Specific Transposon-Mediated Insertion of Foreign Genes into a Baculovirus Genome Propagated in *Escherichia coli*," Journal of Virology, vol. 67, No. 8, pp. 4566-4579 (1993).
Malin, D. et al., "αB-Crystallin: A Novel Regulator of Breast Cancer Metastasis to the Brain," Clinical Cancer Research, http://clincancerres.aacrjournals.org/; doi:10.1158/1078-0432.CCR-13-1255, 13 pages (2013).
Mao, Y.-W. et al., "Human αA- and αB-crystallins bind to Bax and Bcl-$X_S$ to sequester their translocation during staurosporine induced apoptosis," Cell Death and Differentiation, vol. 11, pp. 512-526 (2004).
Moyano, J. V. et al., "αB-Crystallin is a novel oncoprotein that predicts poor clinical outcome in breast cancer," The Journal of Clinical Investigation, vol. 116, No. 1, pp. 261-270 (2006).
Neumann, E. et al., "Gene transfer into mouse lyoma cells by electroporation in high electric fields," The EMBO Journal, vol. 1, No. 7, pp. 841-845 (1982).
NCBI Blast Protein Sequence, SEQ ID No. 9, Jun. 19, 2018, 6 pages.
Obeid, M. et al., "Calreticulin exposure dictates the immunogenicity of cancer cell death," Nature Medicine, vol. 13, No. 1, pp. 54-61 (2007).
Panaretakis, T. et al., "Mechanisms of pre-apoptotic calreticulin exposure in immunogenic cell death," The EMBO Journal, vol. 28, pp. 578-590 (2009).
Pasupuleti, N. et al., "The anti-apoptotic function of human αA-crystallin is directly related to its chaperone activity," Cell Death and Disease, 1, e31, doi:10.1038/cddis.2010.3, 12 pages (2010).
Penjweini, R. et al., "Optimizing the antitumor selectivity of PVP-Hypericin re A546 cancer cells and HLF normal cells through pulsed blue light," Photodiagnosis and Photodynamic Therapy, 10, pp. 591-599 (2013).
Photodynamic Therapy for Cancer, National Cancer Institute, https://www.cancer.gov/about-cancer/treatment/types/surgery/photodynamic-fact-sheet#r3, 3 pages (2011).
Physiochemical Principles of Pharmacy, Ch. 3, "Physiochemical properties of drugs in solution," 4th Edition, pp. 1-38 (2006).
Raghunand, N. et al., "pH and drug resistance in tumors," Drug Resistance Updates, 3, pp. 39-47 (2000).
Raymond, C. K. et al., "Development of the Methylotrophic Yeast *Pichia methanolica* for the Expression of the 65 Kilodalton Isoform of Human Glutamate Decarboxylase," Yeast, vol. 14, pp. 11-23 (1998).
Savill, J., "Recognition and phagocytosis of cells undergoing apoptosis," British Medical Bulletin, vol. 53, No. 3, pp. 491-508 (1997).
Sinkar, V. P. et al., "Molecular biology of RI-plasmid—A review," J. Biosci., vol. 11, Nos. 1-4, pp. 47-57 (1987).
Trédan, O. et al., "Drug Resistance and the Solid Tumor Microenvironment," JNCI, vol. 99, No. 19, pp. 1441-1454 (2007).
Urlaub, G. et al., "Effect of Gamma Rays at the Dihydrofolate Reductase Locus: Deletions and Inversions," Somatic Cell and Molecular Genetics, vol. 12, No. 6, pp. 555-566 (1986).
Wakshlag, J. J. et al., "The Effects of Branched-Chain Amino Acids on Canine Neoplastic Cell Proliferation and Death," J. Nutrition, 136, pp. 2007S-2010S (2006).
Wigler, M. et al., "Biochemical Transfer of Single-Copy Eucaryotic Genes Using total Cellular DNA as Donor," Cell, vol. 14, pp. 725-731 (1978).
Yadav, M. et al., "Predicting immunogenic tumour mutations by combining mass spectrometry and exome sequencing," Nature, vol. 515, pp. 572-576 and Supplementary Materials, 7 pages (2014).
Yang, L. et al., "Improvement of the viability of cultured rat neurons by the non-essential amino acids L-serine and glycine that upregulates expression of the anti-apoptotic gene product Bcl-w," Neuroscience Letters, 295, pp. 97-100 (2000).

*: CRT/HSP70/HSP90p: Calreticulin/HSP70/HSP90-Peptide Complex

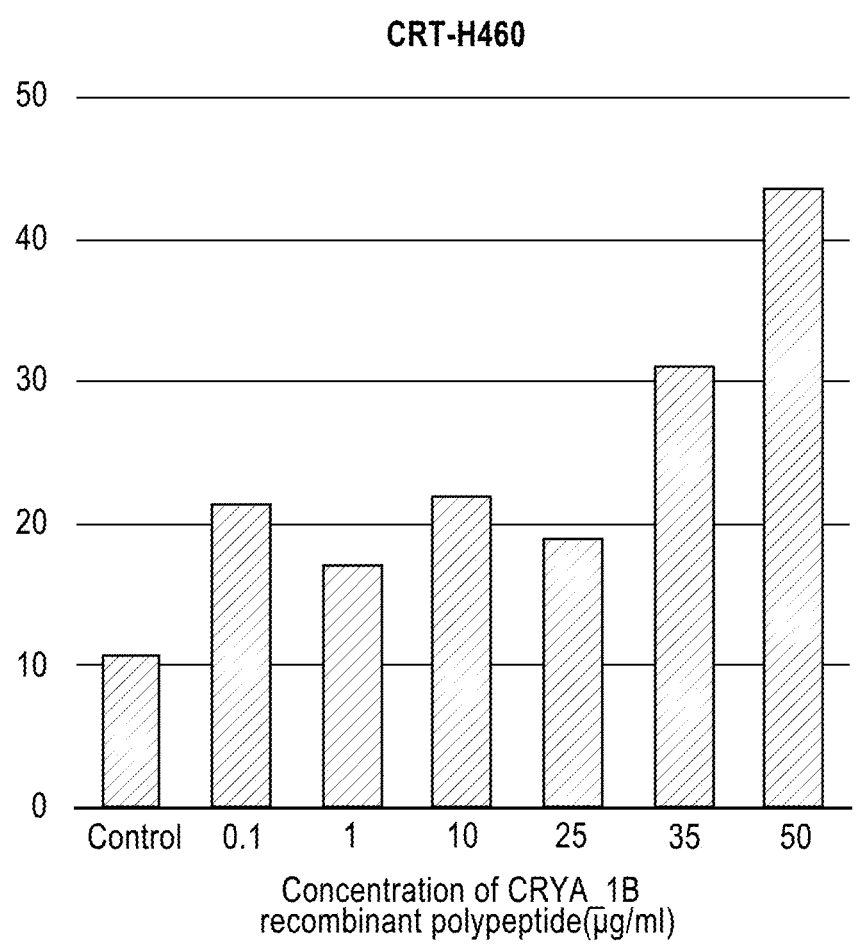

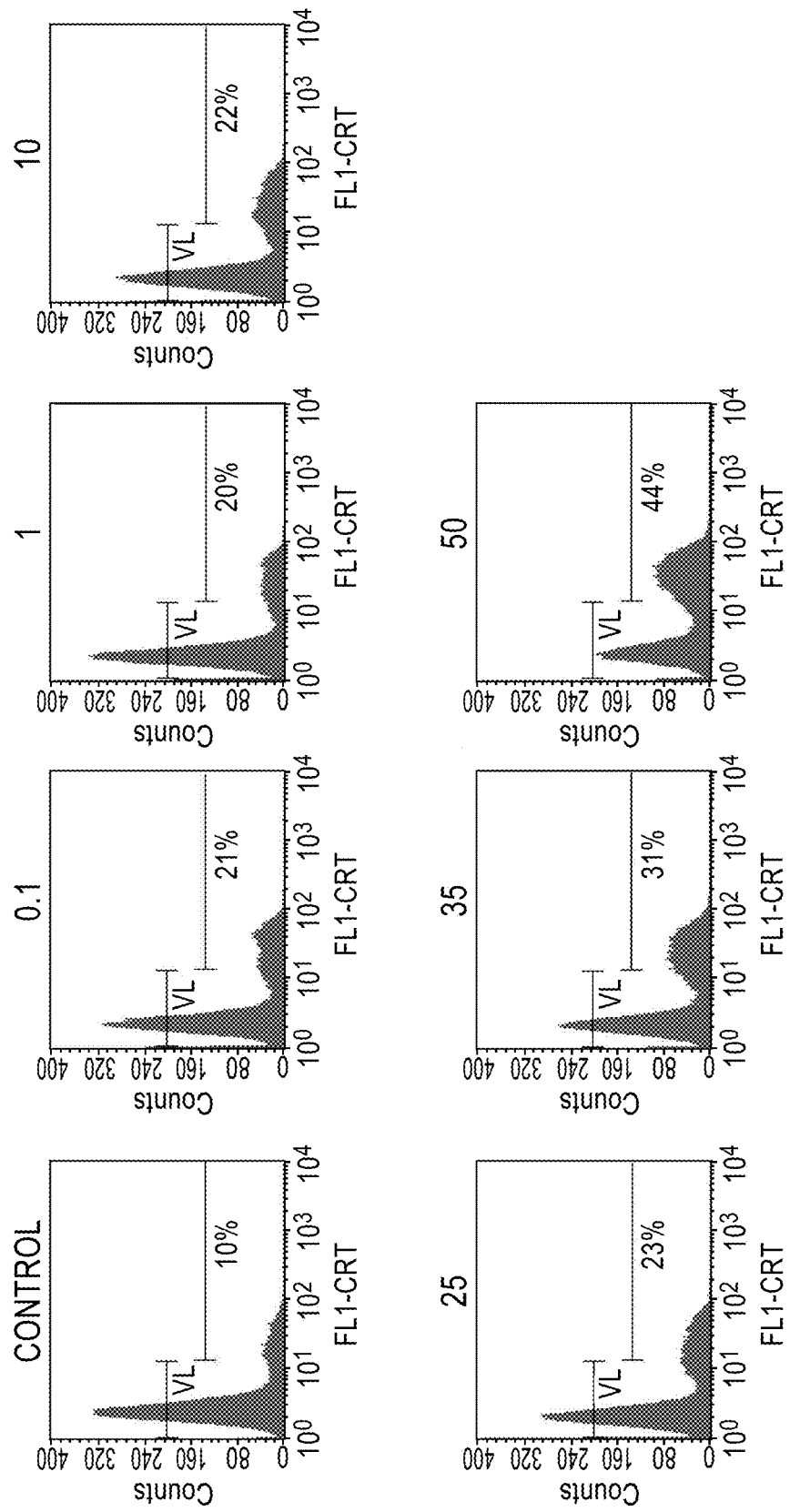

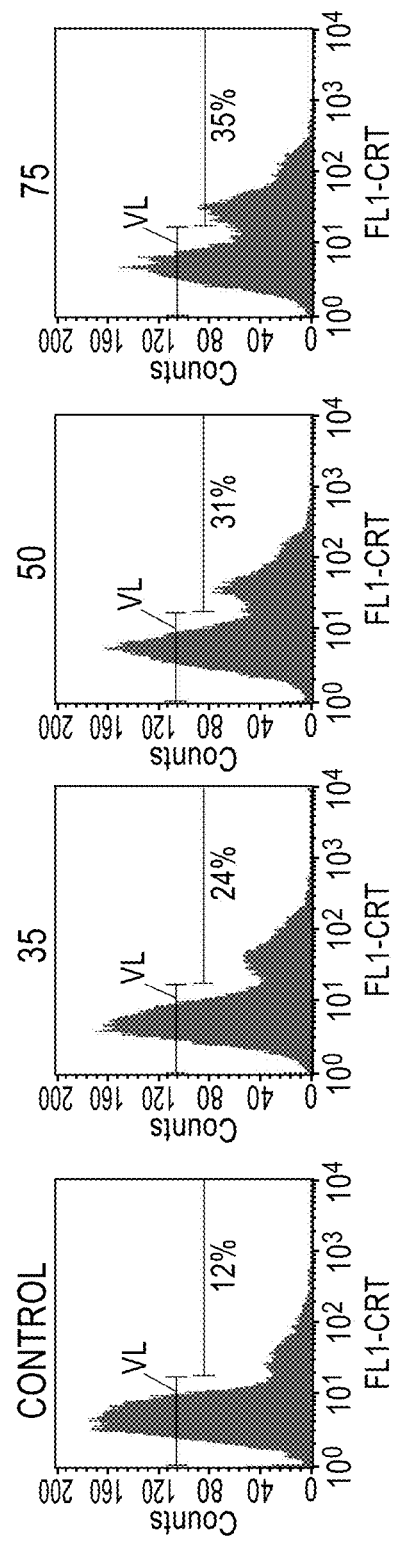

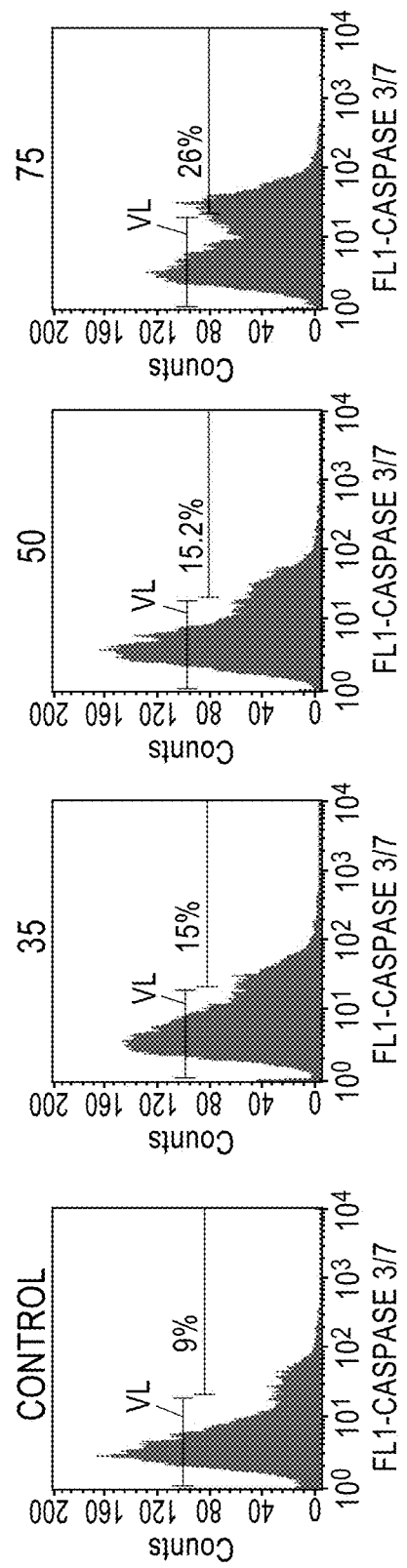

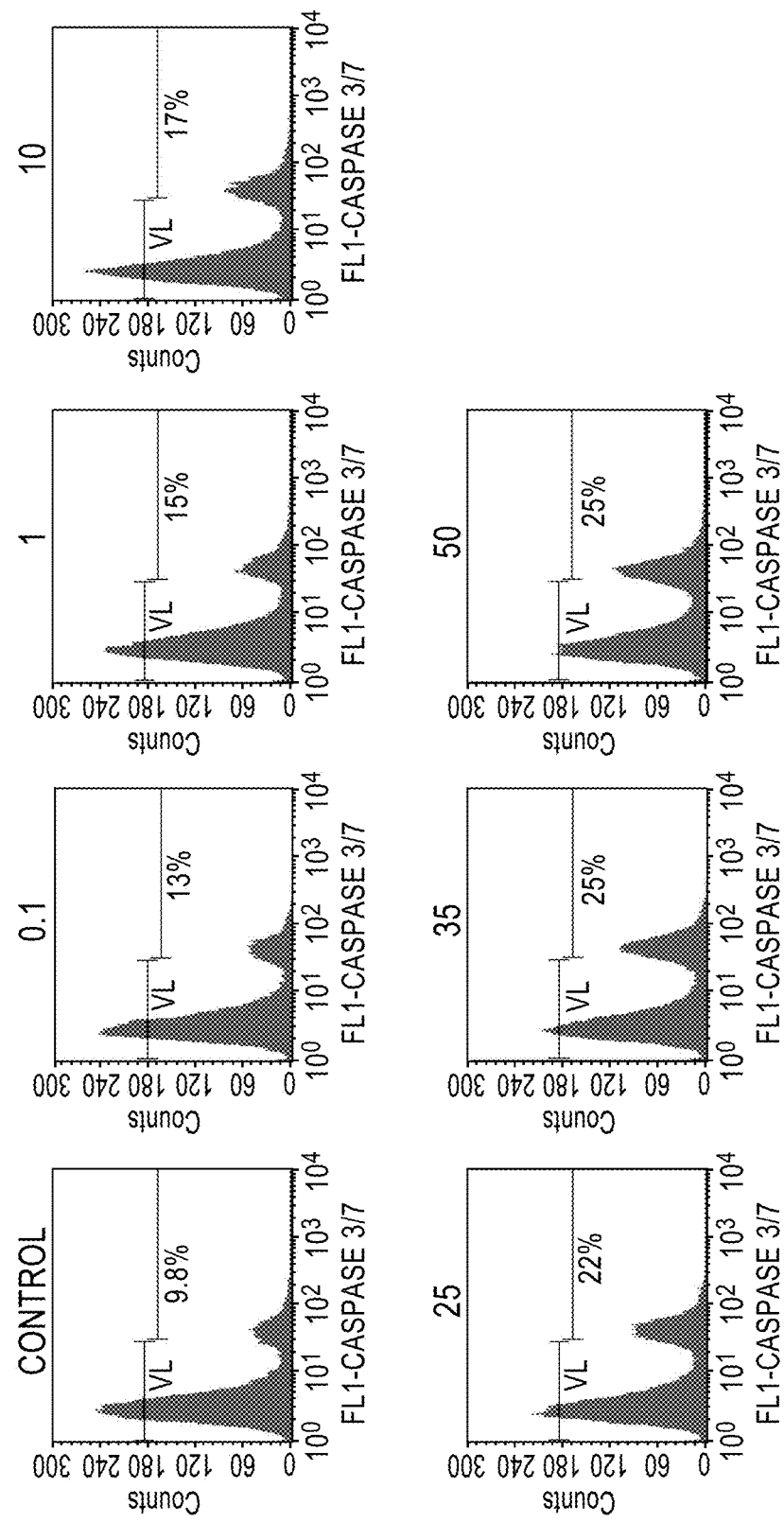

FIG. 21

—o— CRP/SAP $Y = 10.4X - 2.6$

Concentration of CRYA_1B recombinant polypeptide (mg/kg)

CRP/SAP (mg/L)

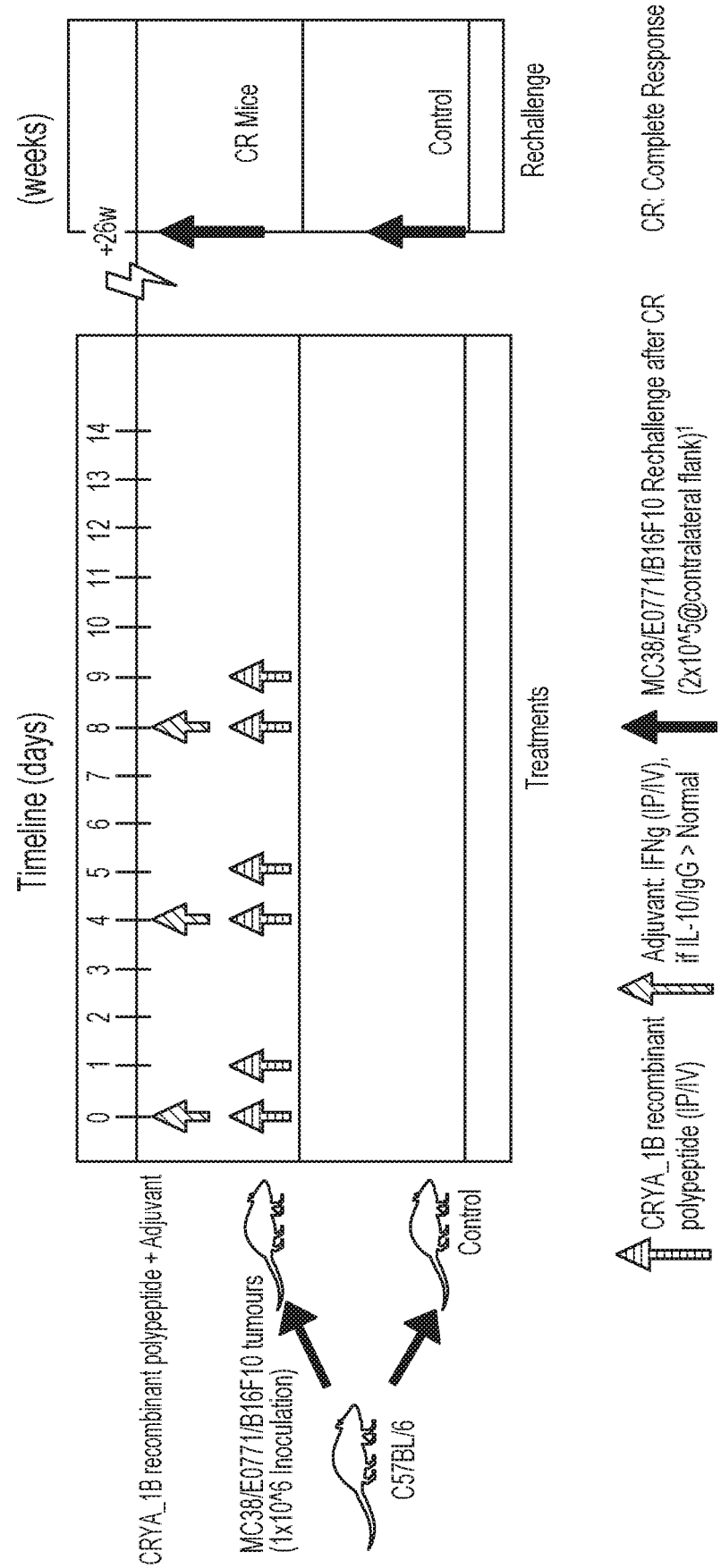

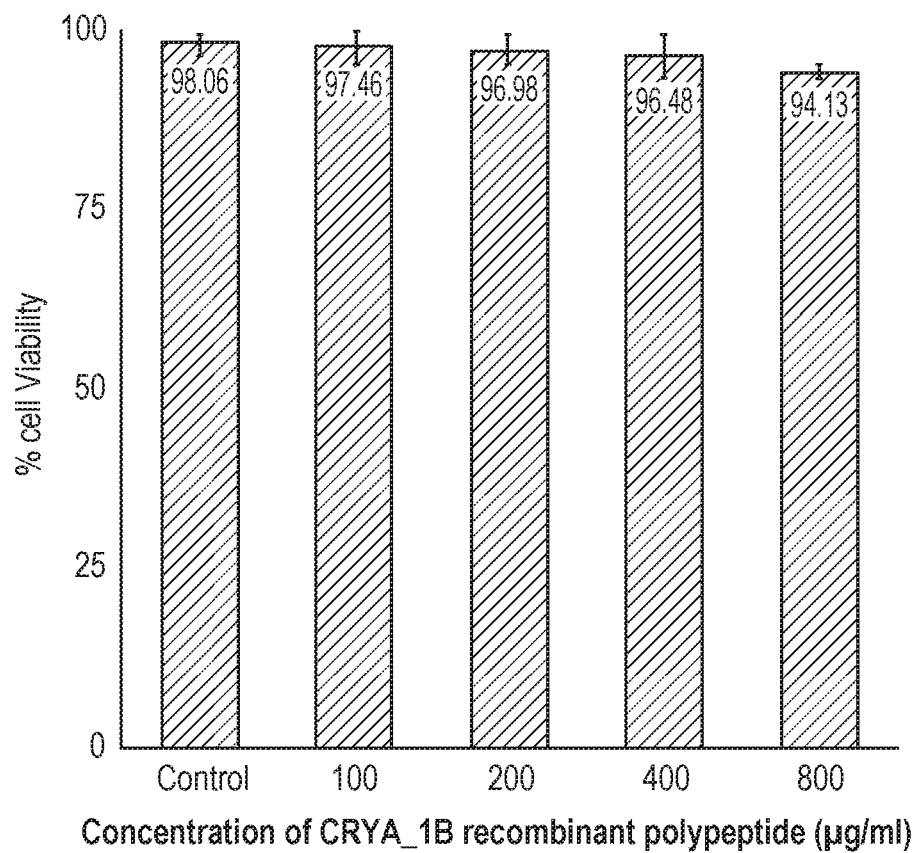

SEQUENCE LISTING

```
<160> NUMBER OF SEQ ID NOS: 52

<210> SEQ ID NO 1
<211> LENGTH: 173
<212> TYPE: PRT
<213> ORGANISM: Anser cygnoides

<400> SEQUENCE: 1

Met Asp Ile Thr Ile Gln His Pro Trp Phe Lys Arg Ala Leu Gly Pro
1               5                   10                  15

Leu Ile Pro Ser Arg Leu Phe Asp Gln Phe Gly Glu Gly Leu Leu
            20                  25                  30

Glu Tyr Asp Leu Leu Pro Leu Phe Ser Ser Thr Ile Ser Pro Tyr Tyr
            35                  40                  45

Arg Gln Ser Leu Phe Arg Ser Val Leu Glu Ser Gly Ile Ser Glu Val
    50                  55                  60

Arg Ser Asp Arg Asp Lys Phe Thr Ile Met Leu Asp Val Lys His Phe
65                  70                  75                  80

Ser Pro Glu Asp Leu Ser Val Lys Ile Ile Asp Asp Phe Val Glu Ile
                85                  90                  95

His Gly Lys His Ser Glu Arg Gln Asp Asp His Gly Tyr Ile Ser Arg
                100                 105                 110

Glu Phe His Arg Arg Tyr Arg Leu Pro Ala Asn Val Asp Gln Ser Ala
            115                 120                 125

Ile Thr Cys Ser Leu Ser Gly Asp Gly Met Leu Thr Phe Ser Gly Pro
        130                 135                 140

Lys Val Pro Ser Asn Met Asp Pro Thr His Ser Glu Arg Pro Ile Pro
145                 150                 155                 160

Val Ser Arg Glu Glu Lys Pro Thr Ser Ala Pro Ser Ser
                165                 170

<210> SEQ ID NO 2
```

```
<211> LENGTH: 173
<212> TYPE: PRT
<213> ORGANISM: Rhea americana

<400> SEQUENCE: 2

Met Asp Ile Thr Ile Gln His Pro Trp Phe Lys Arg Ala Leu Gly Pro
1               5                   10                  15

Leu Ile Pro Ser Arg Leu Phe Asp Gln Phe Gly Glu Gly Leu Leu
            20                  25                  30

Glu Tyr Asp Leu Leu Pro Leu Phe Ser Ser Thr Ile Ser Pro Tyr Tyr
            35                  40                  45

Arg Gln Ser Leu Phe Arg Ser Val Leu Glu Ser Gly Ile Ser Glu Val
        50                  55                  60

Arg Ser Asp Arg Glu Lys Phe Thr Ile Met Leu Asp Val Lys His Phe
65                  70                  75                  80

Ser Pro Glu Asp Leu Ser Val Lys Ile Ile Asp Asp Phe Val Glu Ile
                85                  90                  95

His Gly Lys His Ser Glu Arg Gln Asp Asp His Gly Tyr Ile Ser Arg
            100                 105                 110

Glu Phe His Arg Arg Tyr Arg Leu Pro Ser Asn Val Asp Gln Ser Ala
        115                 120                 125

Ile Thr Cys Ser Leu Ser Ser Asp Gly Met Leu Thr Phe Ser Gly Pro
130                 135                 140

Lys Val Gln Ala Asn Met Asp Pro Ser His Ser Glu Arg Pro Ile Pro
145                 150                 155                 160

Val Ser Arg Glu Glu Lys Pro Thr Ser Ala Pro Ser Ser
                165                 170

<210> SEQ ID NO 3
<211> LENGTH: 149
<212> TYPE: PRT
<213> ORGANISM: Anas platyrhynchos

<400> SEQUENCE: 3

Arg Ala Leu Gly Pro Leu Ile Pro Ser Arg Leu Phe Asp Gln Phe Phe
1               5                   10                  15

Gly Glu Gly Leu Leu Glu Tyr Asp Leu Leu Pro Leu Phe Ser Ser Thr
            20                  25                  30

Ile Ser Pro Tyr Tyr Arg Gln Ser Leu Phe Arg Ser Val Leu Glu Ser
        35                  40                  45

Gly Ile Ser Glu Val Arg Ser Asp Arg Asp Lys Phe Thr Ile Met Leu
    50                  55                  60

Asp Val Lys His Phe Ser Pro Glu Asp Leu Ser Val Lys Ile Ile Asp
65                  70                  75                  80

Asp Phe Val Glu Ile His Gly Lys His Ser Glu Arg Gln Asp Asp His
                85                  90                  95

Gly Tyr Ile Ser Arg Glu Phe His Arg Arg Tyr Arg Leu Pro Ala Asn
            100                 105                 110

Val Asp Gln Ser Ala Ile Thr Cys Ser Leu Ser Gly Asp Gly Met Leu
        115                 120                 125

Thr Phe Ser Gly Pro Lys Val Pro Ser Asn Met Asp Pro Thr His Ser
    130                 135                 140

Glu Arg Pro Ile Pro
145

<210> SEQ ID NO 4
```

```
<211> LENGTH: 174
<212> TYPE: PRT
<213> ORGANISM: Anas platyrhynchos

<400> SEQUENCE: 4
```

| | | | | | | | | | | | | | | |
|---|---|---|---|---|---|---|---|---|---|---|---|---|---|---|
|Met|Asp|Ile|Thr|Ile|His|Asn|Pro|Leu|Ile|Arg|Arg|Pro|Leu|Phe|Ser|
|1| | | |5| | | | |10| | | | |15|
|Trp|Leu|Ala|Pro|Ser|Arg|Ile|Phe|Asp|Gln|Ile|Phe|Gly|Glu|His|Leu|
| | | |20| | | | |25| | | | |30| | |
|Gln|Glu|Ser|Glu|Leu|Leu|Pro|Ala|Ser|Pro|Ser|Leu|Ser|Pro|Phe|Leu|
| | |35| | | | |40| | | | |45| | | |
|Met|Arg|Ser|Pro|Ile|Phe|Arg|Met|Pro|Ser|Trp|Leu|Glu|Thr|Gly|Leu|
| |50| | | | |55| | | | |60| | | | |
|Ser|Glu|Met|Arg|Leu|Glu|Lys|Asp|Lys|Phe|Ser|Val|Asn|Leu|Asp|Val|
|65| | | | |70| | | | |75| | | | |80|
|Lys|His|Phe|Ser|Pro|Glu|Glu|Leu|Lys|Val|Lys|Val|Leu|Gly|Asp|Met|
| | | | |85| | | | |90| | | | |95| |
|Val|Glu|Ile|His|Gly|Lys|His|Glu|Glu|Arg|Gln|Asp|Glu|His|Gly|Phe|
| | | |100| | | | |105| | | | |110| | |
|Ile|Ala|Arg|Glu|Phe|Asn|Arg|Lys|Tyr|Arg|Ile|Pro|Ala|Asp|Val|Asp|
| | |115| | | | |120| | | | |125| | | |
|Pro|Leu|Thr|Ile|Thr|Ser|Ser|Leu|Ser|Leu|Asp|Gly|Val|Leu|Thr|Val|
| |130| | | | |135| | | | |140| | | | |
|Ser|Ala|Pro|Arg|Lys|Gln|Ser|Asp|Val|Pro|Glu|Arg|Ser|Ile|Pro|Ile|
|145| | | | |150| | | | |155| | | | |160|
|Thr|Arg|Glu|Glu|Lys|Pro|Ala|Ile|Ala|Gly|Ala|Gln|Arg|Lys| | |
| | | | |165| | | | |170| | | | | | |

```
<210> SEQ ID NO 5
<211> LENGTH: 173
<212> TYPE: PRT
<213> ORGANISM: Homo sapiens

<400> SEQUENCE: 5
```

| | | | | | | | | | | | | | | |
|---|---|---|---|---|---|---|---|---|---|---|---|---|---|---|
|Met|Asp|Val|Thr|Ile|Gln|His|Pro|Trp|Phe|Lys|Arg|Thr|Leu|Gly|Pro|
|1| | | |5| | | | |10| | | | |15|
|Phe|Tyr|Pro|Ser|Arg|Leu|Phe|Asp|Gln|Phe|Phe|Gly|Glu|Gly|Leu|Phe|
| | | |20| | | | |25| | | | |30| | |
|Glu|Tyr|Asp|Leu|Leu|Pro|Phe|Leu|Ser|Ser|Thr|Ile|Ser|Pro|Tyr|Tyr|
| | |35| | | | |40| | | | |45| | | |
|Arg|Gln|Ser|Leu|Phe|Arg|Thr|Val|Leu|Asp|Ser|Gly|Ile|Ser|Glu|Val|
| |50| | | | |55| | | | |60| | | | |
|Arg|Ser|Asp|Arg|Asp|Lys|Phe|Val|Ile|Phe|Leu|Asp|Val|Lys|His|Phe|
|65| | | | |70| | | | |75| | | | |80|
|Ser|Pro|Glu|Asp|Leu|Thr|Val|Lys|Val|Gln|Asp|Asp|Phe|Val|Glu|Ile|
| | | | |85| | | | |90| | | | |95| |
|His|Gly|Lys|His|Asn|Glu|Arg|Gln|Asp|Asp|His|Gly|Tyr|Ile|Ser|Arg|
| | | |100| | | | |105| | | | |110| | |
|Glu|Phe|His|Arg|Arg|Tyr|Arg|Leu|Pro|Ser|Asn|Val|Asp|Gln|Ser|Ala|
| | |115| | | | |120| | | | |125| | | |
|Leu|Ser|Cys|Ser|Leu|Ser|Ala|Asp|Gly|Met|Leu|Thr|Phe|Cys|Gly|Pro|
| |130| | | | |135| | | | |140| | | | |
|Lys|Ile|Gln|Thr|Gly|Leu|Asp|Ala|Thr|His|Ala|Glu|Arg|Ala|Ile|Pro|
|145| | | | |150| | | | |155| | | | |160|
|Val|Ser|Arg|Glu|Glu|Lys|Pro|Thr|Ser|Ala|Pro|Ser|Ser| | | |
| | | | |165| | | | |170| | | | | | |

```
<210> SEQ ID NO 6
<211> LENGTH: 186
<212> TYPE: PRT
<213> ORGANISM: Drosophila melanogaster

<400> SEQUENCE: 6

Met Ala Asn Ile Pro Leu Leu Leu Ser Leu Ala Asp Asp Leu Gly Arg
1               5                   10                  15

Met Ser Met Val Pro Phe Tyr Glu Pro Tyr Cys Gln Arg Gln Arg
            20                  25                  30

Asn Pro Tyr Leu Ala Leu Val Gly Pro Met Glu Gln Gln Leu Arg Gln
        35                  40                  45

Leu Glu Lys Gln Val Gly Ala Ser Ser Gly Ser Ser Gly Ala Val Ser
    50                  55                  60

Lys Ile Gly Lys Asp Gly Phe Gln Val Cys Met Asp Val Ser His Phe
65                  70                  75                  80

Lys Pro Ser Glu Leu Val Val Lys Val Gln Asp Asn Ser Val Leu Val
                85                  90                  95

Glu Gly Asn His Glu Glu Arg Glu Asp Asp His Gly Phe Ile Thr Arg
            100                 105                 110

His Phe Val Arg Arg Tyr Ala Leu Pro Pro Gly Tyr Glu Ala Asp Lys
        115                 120                 125

Val Ala Ser Thr Leu Ser Ser Asp Gly Val Leu Thr Ile Lys Val Pro
    130                 135                 140

Lys Pro Pro Ala Ile Glu Asp Lys Gly Asn Glu Arg Ile Val Gln Ile
145                 150                 155                 160

Gln Gln Val Gly Pro Ala His Leu Asn Val Lys Glu Asn Pro Lys Glu
                165                 170                 175

Ala Val Glu Gln Asp Asn Gly Asn Asp Lys
            180                 185

<210> SEQ ID NO 7
<211> LENGTH: 174
<212> TYPE: PRT
<213> ORGANISM: Drosophila melanogaster

<400> SEQUENCE: 7

Met Arg Ser Leu Pro Met Phe Trp Arg Met Ala Glu Glu Met Ala Arg
1               5                   10                  15

Met Pro Arg Leu Ser Ser Pro Phe His Ala Phe Phe His Glu Pro Pro
            20                  25                  30

Val Trp Ser Val Ala Leu Pro Arg Asn Trp Gln His Ile Ala Arg Trp
        35                  40                  45

Gln Glu Gln Glu Leu Ala Pro Pro Ala Thr Val Asn Lys Asp Gly Tyr
    50                  55                  60

Lys Leu Thr Leu Asp Val Lys Asp Tyr Ser Glu Leu Lys Val Lys Val
65                  70                  75                  80

Leu Asp Glu Ser Val Val Leu Val Glu Ala Lys Ser Glu Gln Gln Glu
                85                  90                  95

Ala Glu Gln Gly Gly Tyr Ser Ser Arg His Phe Leu Gly Arg Tyr Val
            100                 105                 110

Leu Pro Asp Gly Tyr Glu Ala Asp Lys Val Ser Ser Ser Leu Ser Asp
        115                 120                 125

Asp Gly Val Leu Thr Ile Ser Val Pro Asn Pro Pro Gly Val Gln Glu
    130                 135                 140
```

```
Thr Leu Lys Glu Arg Glu Val Thr Ile Glu Gln Thr Gly Glu Pro Ala
145                 150                 155                 160

Lys Lys Ser Ala Glu Glu Pro Lys Asp Lys Thr Ala Ser Gln
            165                 170

<210> SEQ ID NO 8
<211> LENGTH: 174
<212> TYPE: PRT
<213> ORGANISM: Anser cygnoides

<400> SEQUENCE: 8

Met Asp Ile Thr Ile His Asn Pro Leu Ile Arg Arg Pro Leu Phe Ser
1               5                   10                  15

Trp Leu Ala Pro Ser Arg Ile Phe Asp Gln Ile Phe Gly Glu His Leu
            20                  25                  30

Gln Glu Ser Glu Leu Leu Pro Ala Ser Pro Ser Leu Ser Pro Phe Leu
        35                  40                  45

Met Arg Ser Pro Ile Phe Arg Met Pro Ser Trp Leu Glu Thr Gly Leu
    50                  55                  60

Ser Glu Met Arg Leu Glu Lys Asp Lys Phe Ser Val Asn Leu Asp Val
65                  70                  75                  80

Lys His Phe Ser Pro Glu Glu Leu Lys Val Lys Val Leu Gly Asp Met
                85                  90                  95

Val Glu Ile His Gly Lys His Glu Glu Arg Gln Asp Glu His Gly Phe
            100                 105                 110

Ile Ala Arg Glu Phe Asn Arg Lys Tyr Arg Ile Pro Ala Asp Val Asp
        115                 120                 125

Pro Leu Thr Ile Thr Ser Ser Leu Ser Leu Asp Gly Val Leu Thr Val
    130                 135                 140

Ser Ala Pro Arg Lys Gln Ser Asp Val Pro Glu Arg Ser Ile Pro Ile
145                 150                 155                 160

Thr Arg Glu Glu Lys Pro Ala Ile Ala Gly Ala Gln Arg Lys
                165                 170

<210> SEQ ID NO 9
<211> LENGTH: 173
<212> TYPE: PRT
<213> ORGANISM: Artificial Sequence
<220> FEATURE:
<223> OTHER INFORMATION: artificial polypeptide

<400> SEQUENCE: 9

Met Asp Ile Thr Ile Gln His Pro Trp Phe Lys Arg Ala Leu Gly Pro
1               5                   10                  15

Leu Ile Pro Glu Arg Leu Phe Asp Gln Phe Phe Gly Ser Gly Leu Leu
            20                  25                  30

Ser Tyr Asp Leu Leu Pro Leu Phe Glu Glu Thr Ile Glu Pro Tyr Tyr
        35                  40                  45

Arg Gln Glu Leu Phe Arg Glu Val Leu Ser Glu Gly Ile Glu Ser Val
    50                  55                  60

Arg Glu Asp Arg Asp Lys Phe Thr Ile Met Leu Asp Val Lys His Phe
65                  70                  75                  80

Glu Pro Ser Asp Leu Glu Val Lys Ile Asp Asp Phe Val Ser Ile
                85                  90                  95

His Gly Lys His Glu Ser Arg Gln Asp Asp His Gly Tyr Ile Glu Arg
            100                 105                 110
```

Ser Phe His Arg Arg Tyr Arg Leu Pro Ala Asn Val Asp Gln Glu Ala
            115                 120                 125

Ile Thr Cys Glu Leu Glu Gly Asp Gly Met Leu Thr Phe Glu Gly Pro
        130                 135                 140

Lys Val Pro Glu Asn Met Asp Pro Thr His Glu Ser Arg Pro Ile Pro
145                 150                 155                 160

Val Glu Arg Ser Ser Lys Pro Thr Glu Ala Pro Glu Glu
                165                 170

<210> SEQ ID NO 10
<211> LENGTH: 173
<212> TYPE: PRT
<213> ORGANISM: Artificial Sequence
<220> FEATURE:
<223> OTHER INFORMATION: artificial polypeptide

<400> SEQUENCE: 10

Met Asp Ile Thr Ile Gln His Pro Trp Phe Lys Arg Ala Leu Gly Pro
1               5                   10                  15

Leu Ile Pro Glu Arg Leu Phe Asp Gln Phe Phe Gly Ser Gly Leu Leu
            20                  25                  30

Ser Tyr Asp Leu Leu Pro Leu Phe Glu Glu Thr Ile Glu Pro Tyr Tyr
        35                  40                  45

Arg Gln Glu Leu Phe Arg Glu Val Leu Ser Glu Gly Ile Glu Ser Val
50                  55                  60

Arg Glu Asp Arg Ser Lys Phe Thr Ile Met Leu Asp Val Lys His Phe
65                  70                  75                  80

Glu Pro Ser Asp Leu Glu Val Lys Ile Ile Asp Asp Phe Val Ser Ile
                85                  90                  95

His Gly Lys His Glu Ser Arg Gln Asp Asp His Gly Tyr Ile Glu Arg
            100                 105                 110

Ser Phe His Arg Arg Tyr Arg Leu Pro Glu Asn Val Asp Gln Glu Ala
        115                 120                 125

Ile Thr Cys Glu Leu Glu Gly Asp Gly Met Leu Thr Phe Glu Gly Pro
    130                 135                 140

Lys Val Gln Ala Asn Met Asp Pro Glu His Glu Ser Arg Pro Ile Pro
145                 150                 155                 160

Val Glu Arg Ser Ser Lys Pro Thr Glu Ala Pro Glu Glu
                165                 170

<210> SEQ ID NO 11
<211> LENGTH: 149
<212> TYPE: PRT
<213> ORGANISM: Artificial Sequence
<220> FEATURE:
<223> OTHER INFORMATION: artificial polypeptide

<400> SEQUENCE: 11

Arg Ala Leu Gly Pro Leu Ile Pro Glu Arg Leu Phe Asp Gln Phe Phe
1               5                   10                  15

Gly Ser Gly Leu Leu Ser Tyr Asp Leu Leu Pro Leu Phe Glu Glu Thr
            20                  25                  30

Ile Glu Pro Tyr Tyr Arg Gln Glu Leu Phe Arg Glu Val Leu Ser Glu
        35                  40                  45

Gly Ile Glu Ser Val Arg Glu Asp Arg Asp Lys Phe Thr Ile Met Leu
50                  55                  60

Asp Val Lys His Phe Glu Pro Ser Asp Leu Glu Val Lys Ile Ile Asp
65                  70                  75                  80

```
Asp Phe Val Ser Ile His Gly Lys His Glu Ser Arg Gln Asp Asp His
                85                  90                  95
Gly Tyr Ile Glu Arg Ser Phe His Arg Tyr Arg Leu Pro Ala Asn
            100                 105                 110
Val Asp Gln Glu Ala Ile Thr Cys Glu Leu Glu Gly Asp Gly Met Leu
        115                 120                 125
Thr Phe Glu Gly Pro Lys Val Pro Glu Asn Met Asp Pro Thr His Glu
130                 135                 140
Ser Arg Pro Ile Pro
145
```

<210> SEQ ID NO 12
<211> LENGTH: 174
<212> TYPE: PRT
<213> ORGANISM: Artificial Sequence
<220> FEATURE:
<223> OTHER INFORMATION: artificial polypeptide

<400> SEQUENCE: 12

```
Met Ser Ile Thr Ile His Asn Pro Leu Ile Arg Arg Pro Leu Phe Asp
1               5                   10                  15
Trp Leu Ala Pro Asp Arg Ile Phe Ser Gln Ile Phe Gly Glu His Leu
            20                  25                  30
Gln Glu Asp Glu Leu Leu Pro Ala Asp Pro Leu Asp Pro Phe Leu
        35                  40                  45
Met Arg Asp Pro Ile Phe Arg Met Pro Asp Trp Leu Glu Thr Gly Leu
    50                  55                  60
Asp Glu Met Arg Leu Glu Lys Ser Lys Phe Asp Val Asn Leu Ser Val
65                  70                  75                  80
Lys His Phe Asp Pro Glu Glu Leu Lys Val Lys Val Leu Gly Ser Met
                85                  90                  95
Val Glu Ile His Gly Lys His Glu Glu Arg Gln Ser Glu His Gly Phe
            100                 105                 110
Ile Ala Arg Glu Phe Asn Arg Lys Tyr Arg Ile Pro Ala Ser Val Ser
        115                 120                 125
Pro Leu Thr Ile Thr Asp Asp Leu Asp Leu Ser Gly Val Leu Thr Val
    130                 135                 140
Asp Ala Pro Arg Lys Gln Asp Ser Val Pro Glu Arg Asp Ile Pro Ile
145                 150                 155                 160
Thr Arg Glu Glu Lys Pro Ala Ile Ala Gly Ala Gln Arg Lys
                165                 170
```

<210> SEQ ID NO 13
<211> LENGTH: 173
<212> TYPE: PRT
<213> ORGANISM: Artificial Sequence
<220> FEATURE:
<223> OTHER INFORMATION: artificial polypeptide

<400> SEQUENCE: 13

```
Met Asp Val Thr Ile Gln His Pro Trp Phe Lys Arg Thr Leu Gly Pro
1               5                   10                  15
Phe Tyr Pro Glu Arg Leu Phe Asp Gln Phe Phe Gly Ser Gly Leu Phe
            20                  25                  30
Ser Tyr Asp Leu Leu Pro Phe Leu Glu Glu Thr Ile Glu Pro Tyr Tyr
        35                  40                  45
Arg Gln Glu Leu Phe Arg Thr Val Leu Asp Glu Gly Ile Glu Ser Val
```

```
                50                  55                  60
Arg Glu Asp Arg Asp Lys Phe Val Ile Phe Leu Asp Val Lys His Phe
 65                  70                  75                  80

Glu Pro Ser Asp Leu Thr Val Lys Val Gln Asp Asp Phe Val Ser Ile
                 85                  90                  95

His Gly Lys His Asn Ser Arg Gln Asp Asp His Gly Tyr Ile Glu Arg
                100                 105                 110

Ser Phe His Arg Tyr Arg Leu Pro Glu Asn Val Asp Gln Glu Ala
                115                 120                 125

Leu Glu Cys Glu Leu Glu Ala Asp Gly Met Leu Thr Phe Cys Gly Pro
                130                 135                 140

Lys Ile Gln Thr Gly Leu Asp Ala Thr His Ala Ser Arg Ala Ile Pro
145                 150                 155                 160

Val Glu Arg Ser Ser Lys Pro Thr Glu Ala Pro Glu Glu
                165                 170
```

<210> SEQ ID NO 14
<211> LENGTH: 186
<212> TYPE: PRT
<213> ORGANISM: Artificial Sequence
<220> FEATURE:
<223> OTHER INFORMATION: artificial polypeptide

<400> SEQUENCE: 14

```
Met Ala Asn Ile Pro Leu Leu Leu Ser Leu Ala Val Val Leu Gly Arg
  1               5                  10                  15

Met Ser Met Asp Pro Phe Tyr Glu Pro Tyr Tyr Cys Gln Arg Gln Arg
                 20                  25                  30

Asn Pro Tyr Leu Ala Leu Asp Gly Pro Met Glu Gln Gln Leu Arg Gln
                 35                  40                  45

Leu Glu Lys Gln Asp Gly Ala Ser Ser Gly Ser Ser Gly Ala Asp Ser
             50                  55                  60

Lys Ile Gly Lys Val Gly Phe Gln Asp Cys Met Val Asp Ser His Phe
 65                  70                  75                  80

Lys Pro Ser Glu Leu Asp Asp Lys Asp Gln Val Asn Ser Asp Leu Asp
                 85                  90                  95

Glu Gly Asn His Glu Glu Arg Glu Val Val His Gly Phe Ile Thr Arg
                100                 105                 110

His Phe Asp Arg Arg Tyr Ala Leu Pro Pro Gly Tyr Glu Ala Val Lys
                115                 120                 125

Asp Ala Ser Thr Leu Ser Ser Val Gly Asp Leu Thr Ile Lys Asp Pro
            130                 135                 140

Lys Pro Pro Ala Ile Glu Val Lys Gly Asn Glu Arg Ile Asp Gln Ile
145                 150                 155                 160

Gln Gln Asp Gly Pro Ala His Leu Asn Asp Lys Glu Asn Pro Lys Glu
                165                 170                 175

Ala Asp Glu Gln Val Asn Gly Asn Val Lys
                180                 185
```

<210> SEQ ID NO 15
<211> LENGTH: 174
<212> TYPE: PRT
<213> ORGANISM: Artificial Sequence
<220> FEATURE:
<223> OTHER INFORMATION: artificial polypeptide

<400> SEQUENCE: 15

Met Arg Leu Ser Pro Met Phe Trp Arg Met Ala Glu Glu Met Ala Arg
1               5                   10                  15

Met Pro Arg Ser Leu Leu Pro Phe His Ala Phe Phe His Glu Pro Pro
            20                  25                  30

Asp Trp Leu Asp Ala Ser Pro Arg Asn Trp Gln His Ile Ala Arg Trp
            35                  40                  45

Gln Glu Gln Glu Ser Ala Pro Pro Ala Thr Asp Asn Lys Val Gly Tyr
        50                  55                  60

Lys Ser Thr Ser Val Asp Lys Val Tyr Leu Glu Ser Lys Asp Lys Asp
65                  70                  75                  80

Ser Val Glu Leu Asp Asp Ser Asp Glu Ala Lys Leu Glu Gln Gln Glu
                85                  90                  95

Ala Glu Gln Gly Gly Tyr Leu Leu Arg His Phe Ser Gly Arg Tyr Asp
                100                 105                 110

Ser Pro Val Gly Tyr Glu Ala Val Lys Asp Leu Leu Leu Ser Leu Val
            115                 120                 125

Val Gly Asp Ser Thr Ile Leu Asp Pro Asn Pro Pro Gly Asp Gln Glu
            130                 135                 140

Thr Ser Lys Glu Arg Glu Asp Thr Ile Glu Gln Thr Gly Glu Pro Ala
145                 150                 155                 160

Lys Lys Leu Ala Glu Glu Pro Lys Val Lys Thr Ala Leu Gln
                165                 170

<210> SEQ ID NO 16
<211> LENGTH: 174
<212> TYPE: PRT
<213> ORGANISM: Artificial Sequence
<220> FEATURE:
<223> OTHER INFORMATION: artificial polypeptide

<400> SEQUENCE: 16

Met Ser Ile Thr Ile His Asn Pro Leu Ile Arg Arg Pro Leu Phe Asp
1               5                   10                  15

Trp Leu Ala Pro Asp Arg Ile Phe Ser Gln Ile Phe Gly Glu His Leu
            20                  25                  30

Gln Glu Asp Glu Leu Leu Pro Ala Asp Pro Asp Leu Asp Pro Phe Leu
        35                  40                  45

Met Arg Asp Pro Ile Phe Arg Met Pro Asp Trp Leu Glu Thr Gly Leu
    50                  55                  60

Asp Glu Met Arg Leu Glu Lys Ser Lys Phe Asp Val Asn Leu Ser Val
65                  70                  75                  80

Lys His Phe Asp Pro Glu Glu Leu Lys Val Lys Val Leu Gly Ser Met
                85                  90                  95

Val Glu Ile His Gly Lys His Glu Glu Arg Gln Ser Glu His Gly Phe
                100                 105                 110

Ile Ala Arg Glu Phe Asn Arg Lys Tyr Arg Ile Pro Ala Ser Val Ser
            115                 120                 125

Pro Leu Thr Ile Thr Asp Asp Leu Asp Leu Ser Gly Val Leu Thr Val
            130                 135                 140

Asp Ala Pro Arg Lys Gln Asp Ser Val Pro Glu Arg Asp Ile Pro Ile
145                 150                 155                 160

Thr Arg Glu Glu Lys Pro Ala Ile Ala Gly Ala Gln Arg Lys
                165                 170

<210> SEQ ID NO 17
<211> LENGTH: 519

<212> TYPE: DNA
<213> ORGANISM: Anser cygnoides

<400> SEQUENCE: 17

```
atggatatta ccattcagca tccgtggttt aaacgcgcgc tgggcccgct gattccgagc      60
cgcctgtttg atcagttttt tggcgaaggc ctgctggaat atgatctgct gccgctgttt     120
agcagcacca ttagcccgta ttatcgccag agcctgtttc gcagcgtgct ggaaagcggc     180
attagcgaag tgcgcagcga tcgcgataaa tttaccatta tgctggatgt gaaacatttt     240
agcccggaag atctgagcgt gaaaattatt gatgattttg tggaaattca tggcaaacat     300
agcgaacgcc aggatgatca tggctatatt agccgcgaat tcatcgccg ctatcgcctg      360
ccggcgaacg tggatcagag cgcgattacc tgcagcctga gcggcgatgg catgctgacc     420
tttagcggcc cgaaagtgcc gagcaacatg gatccgaccc atagcgaacg cccgattccg     480
gtgagccgcg aagaaaaaacc gaccagcgcg ccgagcagc                           519
```

<210> SEQ ID NO 18
<211> LENGTH: 519
<212> TYPE: DNA
<213> ORGANISM: Rhea americana

<400> SEQUENCE: 18

```
atggatatta ccattcagca tccgtggttt aaacgcgcgc tgggcccgct gattccgagc      60
cgcctgtttg atcagttttt tggcgaaggc ctgctggaat atgatctgct gccgctgttt     120
agcagcacca ttagcccgta ttatcgccag agcctgtttc gcagcgtgct ggaaagcggc     180
attagcgaag tgcgcagcga tcgcgaaaaa tttaccatta tgctggatgt gaaacatttt     240
agcccggaag atctgagcgt gaaaattatt gatgattttg tggaaattca tggcaaacat     300
agcgaacgcc aggatgatca tggctatatt agccgcgaat tcatcgccg ctatcgcctg      360
ccgagcaacg tggatcagag cgcgattacc tgcagcctga gcagcgatgg catgctgacc     420
tttagcggcc cgaaagtgca ggcgaacatg gatccgagcc atagcgaacg cccgattccg     480
gtgagccgcg aagaaaaaacc gaccagcgcg ccgagcagc                           519
```

<210> SEQ ID NO 19
<211> LENGTH: 447
<212> TYPE: DNA
<213> ORGANISM: Anas platyrhynchos

<400> SEQUENCE: 19

```
cgcgcgctgg gcccgctgat tccgagccgc ctgtttgatc agttttttgg cgaaggcctg      60
ctggaatatg atctgctgcc gctgtttagc agcaccatta gcccgtatta tcgccagagc     120
ctgtttcgca gcgtgctgga aagcggcatt agcgaagtgc gcagcgatcg cgataaattt     180
accattatgc tggatgtgaa acattttagc ccggaagatc tgagcgtgaa aattattgat     240
gattttgtgg aaattcatgg caaacatagc gaacgcagg atgatcatgg ctatattagc      300
cgcgaatttc atcgccgcta tcgcctgccg gcgaacgtgg atcagagcgc gattacctgc     360
agcctgagcg gcgatggcat gctgaccttt agcggcccga agtgccgag caacatggat      420
ccgacccata gcgaacgccc gattccg                                         447
```

<210> SEQ ID NO 20
<211> LENGTH: 522
<212> TYPE: DNA
<213> ORGANISM: Anas platyrhynchos

<400> SEQUENCE: 20

```
atggatatta ccattcataa cccgctgatt cgccgcccgc tgtttagctg gctggcgccg    60
agccgcattt ttgatcagat ttttggcgaa catctgcagg aaagcgaact gctgccggcg   120
agcccgagcc tgagcccgtt tctgatcgcg agcccgattt ttcgcatgcc gagctggctg   180
gaaaccggcc tgagcgaaat gcgcctggaa aaagataaat ttagcgtgaa cctggatgtg   240
aaacatttta gcccggaaga actgaaagtg aaagtgctgg gcgatatggt ggaaattcat   300
ggcaaacatg aagaacgcca ggatgaacat ggctttattg cgcgcgaatt taaccgcaaa   360
tatcgcattc cggcggatgt ggatccgctg accattacca gcagcctgag cctggatggc   420
gtgctgaccg tgagcgcgcc gcgcaaacag agcgatgtgc cggaacgcag cattccgatt   480
acccgcgaag aaaaaccggc gattgcgggc gcgcagcgca aa                     522
```

<210> SEQ ID NO 21
<211> LENGTH: 519
<212> TYPE: DNA
<213> ORGANISM: Homo sapiens

<400> SEQUENCE: 21

```
atggatgtga ccattcagca tccgtggttt aaacgcaccc tgggcccgtt ttatccgagc    60
cgcctgtttg atcagttttt tggcgaaggc ctgtttgaat atgatctgct gccgtttctg   120
agcagcacca ttagcccgta ttatcgccag agcctgtttc gcaccgtgct ggatagcggc   180
attagcgaag tgcgcagcga tcgcgataaa tttgtgattt ttctggatgt gaaacatttt   240
agcccggaag atctgaccgt gaaagtgcag gatgattttg tggaaattca tggcaaacat   300
aacgaacgcc aggatgatca tggctatatt agccgcgaat tcatcgcccg ctatcgcctg   360
ccgagcaacg tggatcagag cgcgctgagc tgcagcctga gcgcggatgg catgctgacc   420
ttttgcggcc cgaaaattca gaccggcctg gatgcgaccc atgcggaacg cgcgattccg   480
gtgagccgcg aagaaaaacc gaccagcgcg ccgagcagc                         519
```

<210> SEQ ID NO 22
<211> LENGTH: 558
<212> TYPE: DNA
<213> ORGANISM: Drosophila melanogaster

<400> SEQUENCE: 22

```
atggcgaaca ttccgctgct gctgagcctg gcggatgatc tgggccgcat gagcatggtg    60
ccgtttatg aaccgtatta ttgccagcgc cagcgcaacc cgtatctggc gctggtgggc   120
ccgatggaac agcagctgcg ccagctggaa aaacaggtgg gcgcgagcag cggcagcagc   180
ggcgcggtga gcaaaattgg caaagatggc tttcaggtgt gcatggatgt gagccatttt   240
aaaccgagcg aactggtggt gaaagtgcag ataacagcg tgctggtgga aggcaaccat   300
gaagaacgcg aagatgatca tggctttatt acccgccatt ttgtgcgccg ctatgcgctg   360
ccgccgggct atgaagcgga taagtggcg agcaccctga gcgcgatgg cgtgctgacc   420
attaaagtgc gaaaccgcc ggcgattgaa gataaaggca cgaacgcat tgtgcagatt   480
cagcaggtgg gccggcgca tctgaacgtg aaagaaaacc gaaagaagc ggtggaacag   540
gataacggca acgataaa                                                558
```

<210> SEQ ID NO 23
<211> LENGTH: 522
<212> TYPE: DNA
<213> ORGANISM: Drosophila melanogaster

<400> SEQUENCE: 23

```
atgcgcagcc tgccgatgtt ttggcgcatg gcggaagaaa tggcgcgcat gccgcgcctg      60
agcagcccgt tcatgcgtt ttttcatgaa ccgccggtgt ggagcgtggc gctgccgcgc     120
aactggcagc atattgcgcg ctggcaggaa caggaactgg cgccgccggc gaccgtgaac     180
aaagatggct ataaactgac cctggatgtg aaagattata gcgaactgaa agtgaaagtg     240
ctggatgaaa gcgtggtgct ggtggaagcg aaaagcgaac agcaggaagc ggaacagggc     300
ggctatagca gccgccattt tctgggccgc tatgtgctgc cggatggcta tgaagcggat     360
aaagtgagca gcagcctgag cgatgatggc gtgctgacca ttagcgtgcc gaacccgccg     420
ggcgtgcagg aaaccctgaa agaacgcgaa gtgaccattg aacagaccgg cgaaccggcg     480
aaaaaaagcg cggaagaacc gaaagataaa accgcgagcc ag                       522
```

<210> SEQ ID NO 24
<211> LENGTH: 522
<212> TYPE: DNA
<213> ORGANISM: Anser cygnoides

<400> SEQUENCE: 24

```
atggatatta ccattcataa cccgctgatt cgccgcccgc tgtttagctg gctggcgccg      60
agccgcattt ttgatcagat ttttggcgaa catctgcagg aaagcgaact gctgccggcg     120
agcccgagcc tgagcccgtt tctgatgcgc agcccgattt ttcgcatgcc gagctggctg     180
gaaaccggcc tgagcgaaat cgccctggaa aaagataaat ttagcgtgaa cctggatgtg     240
aaacatttta gcccggaaga actgaaagtg aaagtgctgg gcgatatggt ggaaattcat     300
ggcaaacatg aagaacgcca ggatgaacat ggctttattg cgcgcgaatt taaccgcaaa     360
tatcgcattc cggcggatgt ggatccgctg accattacca gcagcctgag cctggatggc     420
gtgctgaccg tgagcgcgcc cgcaaacag agcgatgtgc cggaacgcag cattccgatt     480
acccgcgaag aaaaaccggc gattgcgggc gcgcagcgca aa                       522
```

<210> SEQ ID NO 25
<211> LENGTH: 519
<212> TYPE: DNA
<213> ORGANISM: Artificial Sequence
<220> FEATURE:
<223> OTHER INFORMATION: artificial polynucleotide

<400> SEQUENCE: 25

```
atggatatta ccattcagca tccgtggttt aaacgcgcgc tgggcccgct gattccggaa      60
cgcctgtttg atcagttttt tggcagcggc ctgctgagct atgatctgct gccgctgttt     120
gaagaaacca ttgaaccgta ttatcgccag gaactgtttc gcgaagtgct gagcgaaggc     180
attgaaagcg tgcgcgaaga tcgcgataaa tttaccatta tgctggatgt gaaacatttt     240
gaaccgagcg atctggaagt gaaaattatt gatgattttg tgagcattca tggcaaacat     300
gaaagccgcc aggatgatca tggctatatt gaacgcagct tcatcgccg ctatcgcctg     360
ccggcgaacg tggatcagga agcgattacc tgcgaactgg aaggcgatgg catgctgacc     420
tttgaaggcc cgaaagtgcc ggaaaacatg atccgaccc atgaaagccg cccgattccg     480
gtggaacgca gcagcaaacc gaccgaagcg ccggaagaa                           519
```

<210> SEQ ID NO 26
<211> LENGTH: 519
<212> TYPE: DNA

<213> ORGANISM: Artificial Sequence
<220> FEATURE:
<223> OTHER INFORMATION: artificial polynucleotide

<400> SEQUENCE: 26

```
atggatatta ccattcagca tccgtggttt aaacgcgcgc tgggcccgct gattccggaa      60
cgcctgtttg atcagttttt tggcagcggc ctgctgagct atgatctgct gccgctgttt     120
gaagaaacca ttgaaccgta ttatcgccag gaactgtttc gcgaagtgct gagcgaaggc     180
attgaaagcg tgcgcgaaga tcgcagcaaa tttaccatta tgctggatgt gaaacatttt     240
gaaccgagcg atctggaagt gaaaattatt gatgattttg tgagcattca tggcaaacat     300
gaaagccgcc aggatgatca tggctatatt gaacgcagct tcatcgccg ctatcgcctg      360
ccggaaaacg tggatcagga agcgattacc tgcgaactgg aagaagatgg catgctgacc     420
tttgaaggcc cgaaagtgca ggcgaacatg gatccggaac atgaaagccg cccgattccg     480
gtggaacgca gcagcaaacc gaccgaagcg ccggaagaa                            519
```

<210> SEQ ID NO 27
<211> LENGTH: 447
<212> TYPE: DNA
<213> ORGANISM: Artificial Sequence
<220> FEATURE:
<223> OTHER INFORMATION: artificial polynucleotide

<400> SEQUENCE: 27

```
cgcgcgctgg gcccgctgat tccggaacgc ctgtttgatc agttttttgg cagcggcctg      60
ctgagctatg atctgctgcc gctgtttgaa gaaaccattg aaccgtatta tcgccaggaa     120
ctgtttcgcg aagtgctgag cgaaggcatt gaaagcgtgc gcgaagatcg cgataaattt     180
accattatgc tggatgtgaa acattttgaa ccgagcgatc tggaagtgaa aattattgat     240
gattttgtga gcattcatgg caaacatgaa agccgccagg atgatcatgg ctatattgaa     300
cgcagctttc atcgccgcta tcgcctgccg cgaacgtgg atcaggaagc gattacctgc      360
gaactggaag gcgatggcat gctgaccttt gaaggcccga agtgccgga aacatggat      420
ccgacccatg aaagccgccc gattccg                                         447
```

<210> SEQ ID NO 28
<211> LENGTH: 522
<212> TYPE: DNA
<213> ORGANISM: Artificial Sequence
<220> FEATURE:
<223> OTHER INFORMATION: artificial polynucleotide

<400> SEQUENCE: 28

```
atgagcatta ccattcataa cccgctgatt cgccgcccgc tgtttgattg gctggcgccg      60
gatcgcattt ttagccagat ttttggcgaa catctgcagg aagatgaact gctgccggcg     120
gatccggatc tggatccgtt tctgatgcgc gatccgattt ttcgcatgcc ggattggctg     180
gaaaccggcc tggatgaaat gcgcctggaa aaaagcaaat ttgatgtgaa cctgagcgtg     240
aaacatttg atccggaaga actgaaagtg aaagtgctgg gcagcatggt ggaaattcat      300
ggcaaacatg aagaacgcca gagcgaacat ggctttattg cgcgcgaatt taaccgcaaa     360
tatcgcattc cggcgagcgt gagcccgctg accattaccg atgatctgga tctgagcggc     420
gtgctgaccg tggatgcgcc gcgcaaacag gatagcgtgc cggaacgcga tattccgatt     480
acccgcgaag aaaaaccggc gattgcgggc gcgcagcgca aa                        522
```

```
<210> SEQ ID NO 29
<211> LENGTH: 519
<212> TYPE: DNA
<213> ORGANISM: Artificial Sequence
<220> FEATURE:
<223> OTHER INFORMATION: artificial polynucleotide

<400> SEQUENCE: 29
atggatgtga ccattcagca tccgtggttt aaacgcaccc tgggcccgtt ttatccggaa    60
cgcctgtttg atcagttttt tggcagcggc ctgtttagct atgatctgct gccgtttctg   120
gaagaaacca ttgaaccgta ttatcgccag gaactgtttc gcaccgtgct ggatgaaggc   180
attgaaagcg tgcgcgaaga tcgcgataaa tttgtgattt ttctggatgt gaaacatttt   240
gaaccgagcg atctgaccgt gaaagtgcag gatgattttg tgagcattca tggcaaacat   300
aacagccgcc aggatgatca tggctatatt gaacgcagct tcatcgcccg ctatcgcctg   360
ccggaaaacg tggatcagga agcgctggaa tgcgaactgg aagcggatgg catgctgacc   420
ttttgcggcc cgaaaattca gaccggcctg atgcgacccc atgcgagccg cgcgattccg   480
gtggaacgca gcagcaaacc gaccgaagcg ccggaagaa                          519

<210> SEQ ID NO 30
<211> LENGTH: 558
<212> TYPE: DNA
<213> ORGANISM: Artificial Sequence
<220> FEATURE:
<223> OTHER INFORMATION: artificial polynucleotide

<400> SEQUENCE: 30
atggcgaaca ttccgctgct gctgagcctg gcggtggtgc tgggccgcat gagcatggat    60 ccgtttatg aaccgtatta ttgccagcgc cagcgcaacc cgtatctggc gctggatggc   120
ccgatggaac agcagctgcg ccagctggaa aaacaggatg cgcgagcag cggcagcagc   180 ggcgcggata gcaaaattgg caaagtgggc tttcaggatt gcatggtgga tagccatttt   240
aaaccgagcg aactggatga taaagatcag gtgaacagcg atctggatga aggcaaccat   300
gaagaacgcg aagtggtgca tggctttatt acccgccatt ttgatcgccg ctatgcgctg   360
ccgccgggct atgaagcggt gaaagatgcg agcaccctga gcagcgtggg cgatctgacc   420
attaaagatc cgaaaccgcc ggcgattgaa gtgaaaggca cgaacgcat tgatcagatt    480 cagcaggatg gcccggcgca tctgaacgat aaagaaaacc cgaaagaagc ggatgaacag   540
gtgaacggca acgtgaaa                                                 558

<210> SEQ ID NO 31
<211> LENGTH: 522
<212> TYPE: DNA
<213> ORGANISM: Artificial Sequence
<220> FEATURE:
<223> OTHER INFORMATION: artificial polynucleotide

<400> SEQUENCE: 31
atgcgcctga gcccgatgtt ttggcgcatg gcggaagaaa tggcgcgcat gccgcgcagc    60
ctgctgccgt tcatgcgtt ttttcatgaa ccgccggatt ggctggatgc gagcccgcgc   120
aactggcagc atattgcgcg ctggcaggaa caggaaagcg cgccgccggc gaccgataac   180
aaagtgggct ataaaagcac cagcgtggat aaagtgtatc tggaaagcaa agataaagat   240
agcgtggaac tggatgatag cgatgaagcg aaactggaac agcaggaagc ggaacagggc   300
ggctatctgc tgcgccattt tagcggccgc tatgatagcc cggtgggcta tgaagcggtg   360
```

```
aaagatctgc tgctgagcct ggtggtgggc gatagcacca ttctggatcc gaacccgccg    420
ggcgatcagg aaaccagcaa agaacgcgaa gataccattg aacagaccgg cgaaccggcg    480
aaaaaactgg cggaagaacc gaaagtgaaa accgcgctgc ag                       522

<210> SEQ ID NO 32
<211> LENGTH: 522
<212> TYPE: DNA
<213> ORGANISM: Artificial Sequence
<220> FEATURE:
<223> OTHER INFORMATION: artificial polynucleotide

<400> SEQUENCE: 32
atgagcatta ccattcataa cccgctgatt cgccgcccgc tgtttgattg gctggcgccg     60
gatcgcattt ttagccagat ttttggcgaa catctgcagg aagatgaact gctgccggcg    120
gatccggatc tggatccgtt tctgatgcgc gatccgattt tcgcatgcc ggattggctg    180 gaaaccggcc tggatgaaat gcgcctgaaa aaagcaaat ttgatgtgaa cctgagcgtg    240
aaacattttg atccggaaga actgaaagtg aaagtgctgg cagcatggt ggaaattcat    300 ggcaaacatg aagaacgcca gagcgaacat ggctttattg cgcgcgaatt taaccgcaaa    360
tatcgcattc cggcgagcgt gagcccgctg accattaccg atgatctgga tctgagcggc    420
gtgctgaccg tggatgcgcc gcgcaaacag gatagcgtgc cggaacgcga tattccgatt    480
acccgcgaag aaaaaccggc gattgcgggc gcgcagcgca aa                       522

<210> SEQ ID NO 33
<211> LENGTH: 50
<212> TYPE: DNA
<213> ORGANISM: Anser cygnoides

<400> SEQUENCE: 33 gggggggcata tggacattac catccagcac ccctggttca agcgcgctct               50

<210> SEQ ID NO 34
<211> LENGTH: 39
<212> TYPE: DNA
<213> ORGANISM: Anser cygnoides

<400> SEQUENCE: 34 gggggggaagc ttttactcct caggcgcctc ggtgggctt                           39

<210> SEQ ID NO 35
<211> LENGTH: 32
<212> TYPE: DNA
<213> ORGANISM: Artificial Sequence
<220> FEATURE:
<223> OTHER INFORMATION: artificial polynucleotide

<400> SEQUENCE: 35
cctctgttcg aggagactat cgagccctac ta                                   32

<210> SEQ ID NO 36
<211> LENGTH: 32
<212> TYPE: DNA
<213> ORGANISM: Artificial Sequence
<220> FEATURE:
<223> OTHER INFORMATION: artificial polynucleotide

<400> SEQUENCE: 36
tagtagggct cgatagtctc ctcgaacaga gg                                   32
```

<210> SEQ ID NO 37
<211> LENGTH: 64
<212> TYPE: DNA
<213> ORGANISM: Artificial Sequence
<220> FEATURE:
<223> OTHER INFORMATION: artificial polynucleotide

<400> SEQUENCE: 37
accggcagga gctgttccgc gaggtgctgt cggagggcat tgagtcggtg agggaggacc    60
ggga                                                                64

<210> SEQ ID NO 38
<211> LENGTH: 64
<212> TYPE: DNA
<213> ORGANISM: Artificial Sequence
<220> FEATURE:
<223> OTHER INFORMATION: artificial polynucleotide

<400> SEQUENCE: 38
tcccggtcct ccctcaccga ctcaatgccc tccgacagca cctcgcggaa cagctcctgc    60
cggt                                                                64

<210> SEQ ID NO 39
<211> LENGTH: 52
<212> TYPE: DNA
<213> ORGANISM: Artificial Sequence
<220> FEATURE:
<223> OTHER INFORMATION: artificial polynucleotide

<400> SEQUENCE: 39
actatgctgg acgtaaaaca ctttgagcct tcggacctgg aggtgaagat ta            52

<210> SEQ ID NO 40
<211> LENGTH: 52
<212> TYPE: DNA
<213> ORGANISM: Artificial Sequence
<220> FEATURE:
<223> OTHER INFORMATION: artificial polynucleotide

<400> SEQUENCE: 40
taatcttcac ctccaggtcc gaaggctcaa agtgttttac gtccagcatg at            52

<210> SEQ ID NO 41
<211> LENGTH: 33
<212> TYPE: DNA
<213> ORGANISM: Artificial Sequence
<220> FEATURE:
<223> OTHER INFORMATION: artificial polynucleotide

<400> SEQUENCE: 41
aagattatcg acgactttgt gtcgatccat ggc                                 33

<210> SEQ ID NO 42
<211> LENGTH: 33
<212> TYPE: DNA
<213> ORGANISM: Artificial Sequence
<220> FEATURE:
<223> OTHER INFORMATION: artificial polynucleotide

<400> SEQUENCE: 42
gccatggatc gacacaaagt cgtcgataat ctt                                 33

<210> SEQ ID NO 43
<211> LENGTH: 57
<212> TYPE: DNA

```
<213> ORGANISM: Artificial Sequence
<220> FEATURE:
<223> OTHER INFORMATION: artificial polynucleotide

<400> SEQUENCE: 43
ggcaagcacg agtcgagaca ggacgaccac ggctacatcg agcggtcgtt tcaccgc          57

<210> SEQ ID NO 44
<211> LENGTH: 57
<212> TYPE: DNA
<213> ORGANISM: Artificial Sequence
<220> FEATURE:
<223> OTHER INFORMATION: artificial polynucleotide

<400> SEQUENCE: 44
gcggtgaaac gaccgctcga tgtagccgtg gtcgtcctgt ctcgactcgt gcttgcc          57

<210> SEQ ID NO 45
<211> LENGTH: 41
<212> TYPE: DNA
<213> ORGANISM: Artificial Sequence
<220> FEATURE:
<223> OTHER INFORMATION: artificial polynucleotide

<400> SEQUENCE: 45
gcggaccagg aggccatcac ctgcgagctg gagggcgacg g                          41

<210> SEQ ID NO 46
<211> LENGTH: 41
<212> TYPE: DNA
<213> ORGANISM: Artificial Sequence
<220> FEATURE:
<223> OTHER INFORMATION: artificial polynucleotide

<400> SEQUENCE: 46
ccgtcgccct ccagctcgca ggtgatggcc tcctggtcca c                          41

<210> SEQ ID NO 47
<211> LENGTH: 54
<212> TYPE: DNA
<213> ORGANISM: Artificial Sequence
<220> FEATURE:
<223> OTHER INFORMATION: artificial polynucleotide

<400> SEQUENCE: 47
ttcgaccagt ttttcggatc gggtctgctg tcgtatgacc tgctgcctct gttc             54

<210> SEQ ID NO 48
<211> LENGTH: 39
<212> TYPE: DNA
<213> ORGANISM: Artificial Sequence
<220> FEATURE:
<223> OTHER INFORMATION: artificial polynucleotide

<400> SEQUENCE: 48
ggggaccttg gggccctcga aggtcagcat gccgtcgcc                              39

<210> SEQ ID NO 49
<211> LENGTH: 57
<212> TYPE: DNA
<213> ORGANISM: Artificial Sequence
<220> FEATURE:
<223> OTHER INFORMATION: artificial polynucleotide

<400> SEQUENCE: 49
ttcaagcgcg ctctgggacc cctgattcca gagcgtctgt tcgaccagtt tttcgga          57
```

```
<210> SEQ ID NO 50
<211> LENGTH: 55
<212> TYPE: DNA
<213> ORGANISM: Artificial Sequence
<220> FEATURE:
<223> OTHER INFORMATION: artificial polynucleotide

<400> SEQUENCE: 50
cacggggatg ggcctcgact cgtgggtggg gtccatgttc tcggggacct tgggg          55

<210> SEQ ID NO 51
<211> LENGTH: 18
<212> TYPE: DNA
<213> ORGANISM: Artificial Sequence
<220> FEATURE:
<223> OTHER INFORMATION: artificial polynucleotide

<400> SEQUENCE: 51
atggacatta ccatccag                                                  18

<210> SEQ ID NO 52
<211> LENGTH: 60
<212> TYPE: DNA
<213> ORGANISM: Artificial Sequence
<220> FEATURE:
<223> OTHER INFORMATION: artificial polynucleotide

<400> SEQUENCE: 52
aagcttttac tcctcaggcg cctcggtggg cttcgacgac cgctccacgg ggatgggcct    60
```

US 10,675,332 B1

RECOMBINANT POLYPEPTIDES AND METHODS OF USE THEREOF

SEQUENCE LISTING

The instant application contains a Sequence Listing which has been submitted in ASCII format via EFS-Web and is hereby incorporated by reference in its entirety. Said ASCII copy, created on Jul. 17, 2019, is named "IMHC-002_SequenceListing_ST25" and is 41 KB in size.

BACKGROUND OF THE INVENTION

Immunogenic cell death is a form of cell death or apoptosis. Unlike traditional apoptosis, which is mostly non-immunogenic, immunogenic cell death in cancer cells can induce an effective anti-tumor immune response through the activation of dendritic cells. The pre-apoptotic state is defined as the state before the activation of Caspase 3/7, the manifestation of cell apoptosis. Immunogenic cell death is characterized by the expression of pre-apoptotic damage-associated-molecular-patterns (DAMPs) on the surface of a dying cell. There are three important pre-apoptotic DAMPs which are exposed to the cell surface during immunogenic cell death: calreticulin (CRT), HSP70 and HSP90. These three pre-apoptotic DAMP signals play an important role in dendritic cell recruitment and cell phagocytosis by CRT and dendritic cell maturation/activation by HSP70 and HSP90, resulting in effective anti-tumor immune response. Selected forms of chemotherapy and radiotherapy can induce collateral immunogenic cell death. While these therapies can induce one or two of the three pre-apoptotic DAMP signals, they do not induce the expression of all three pre-apoptotic DAMP signals. Furthermore, chemotherapy and radiotherapy are immunosuppressive therapies, which reduce numbers of lymphocytes and also cause collateral damages to surrounding non-tumor cells, resulting in poor anti-tumor immune responses and also adverse events respectively.

There is a need for compositions and methods that induce immunogenic cell death with increased efficiency and potency by inducing the expression of all three pre-apoptotic DAMP signals, while minimizing adverse effects. There is a need for compositions and methods of personalized and universal cancer immunotherapies by inducing dendritic cell mediated long-term adaptive immune responses. There is a need for compositions and methods of inducing T-cell polyclonal diversity with neoantigenic breadth in order to prevent cancer occurrence, irrespective of the cancer type or the tumor phenotype. The present disclosure addresses these needs.

SUMMARY OF THE INVENTION

The present disclosure provides a method of treating cancer in a subject in need thereof comprising a) administering a first amount of an agent that reduces IL-10 to the subject; b) administering a first amount of a recombinant polypeptide comprising an amino acid sequence having at least 95% sequence identity to the polypeptide of SEQ ID NO: 9, or a nucleic acid encoding the recombinant polypeptide comprising an amino acid sequence having at least 95% sequence identity to the polypeptide of SEQ ID NO: 9 to the subject between 2-24 hours after the administration of the first amount of the agent; and c) administering a second amount of the recombinant polypeptide or the nucleic acid to the subject at least 20 hours after the administration of the first amount of the recombinant polypeptide or the nucleic acid. In one aspect, the first amount of the recombinant polypeptide or the nucleic acid of b) is administered to the subject at about 3-4 hours after the administration of the first amount of the agent; and the second amount of the recombinant polypeptide or the nucleic acid of c) is administered to the subject at least 24 hours after the administration of the first amount of the recombinant polypeptide or the nucleic acid. In one aspect, the recombinant polypeptide comprises an amino acid sequence having at least 99% sequence identity to the polypeptide of SEQ ID NO: 9, or a nucleic acid encoding the recombinant polypeptide comprising an amino acid sequence having at least 99% sequence identity to the polypeptide of SEQ ID NO: 9. In one aspect, the recombinant polypeptide or the nucleic acid is formulated with a pharmaceutically acceptable carrier.

In one aspect, the method of the disclosure further comprises d) administering a second amount of the agent to the subject at least 24 hours after the administration of the second amount of the recombinant polypeptide or the nucleic acid; e) administering a third amount of the recombinant polypeptide or the nucleic acid to the subject between 2-24 hours after the administration of the second amount of the agent to the subject; and f) administering a fourth amount of the recombinant polypeptide or the nucleic acid to the subject at least 20 hours after the administration of the third amount of the recombinant polypeptide or the nucleic acid to the subject. In one aspect, the third amount of the recombinant polypeptide or the nucleic acid of e) is administered to the subject at about 3-4 hours after the administration of the second amount of the agent; and the fourth amount of the recombinant polypeptide or the nucleic acid of f) is administered to the subject at least 24 hours after the administration of the third amount of the recombinant polypeptide or the nucleic acid.

In one aspect, the method of the disclosure further comprises g) administering a third amount of the agent to the subject at least 24 hours after the administration of the fourth amount of the recombinant polypeptide or the nucleic acid; h) administering a fifth amount of the recombinant polypeptide or the nucleic acid between 2-24 hours after the administration of the third amount of the agent; and i) administering a sixth amount of the recombinant polypeptide or the nucleic acid to the subject at least 20 hours after the administration of the fifth amount of the recombinant polypeptide or the nucleic acid. In one aspect, the fifth amount of a recombinant polypeptide or the nucleic acid of h) is administered to the subject at about 3-4 hours after the administration of the third amount of the agent; and the sixth amount of the recombinant polypeptide or the nucleic acid of i) is administered to the subject at least 24 hours after the administration of the fifth amount of the recombinant polypeptide or the nucleic acid.

In one aspect, the method of the disclosure further comprises j) administering a fourth amount of the agent to the subject at least 24 hours after the administration of the sixth amount of the recombinant polypeptide or the nucleic acid; k) administering a seventh amount of the recombinant polypeptide or the nucleic acid at between 2-24 hours after the administration of the fourth amount of the agent; and l) administering a eighth amount of the recombinant polypeptide or the nucleic acid to the subject at least 20 hours after the administration of the seventh amount of the recombinant polypeptide or the nucleic acid. In one aspect, the seventh amount of the recombinant polypeptide or the nucleic acid of k) is administered to the subject at about 3-4 hours after the administration of the fourth amount of the agent; and the eighth amount of the recombinant polypeptide or the nucleic acid of 1) is administered to the subject at least 24 hours after the administration of the seventh amount of the recombinant polypeptide or the nucleic acid.

In one aspect, any of the first amount, the second amount, the third amount and/or the fourth amount of the agent is selected based on the ratio: $IgG_{subject}$:$IgG_{healthy}$, wherein $IgG_{subject}$ is the amount of IgG in serum from the subject prior to administration of the first amount, the second amount, the third amount or the fourth amount of recombinant polypeptide or the nucleic acid and $IgG_{healthy}$ is the amount of IgG in serum from a healthy subject.

In one aspect, any of the first amount, the second amount, the third amount and/or the fourth amount of the agent is selected based on the ratio: $IL\text{-}10_{subject}$:$IL\text{-}10_{healthy}$, wherein $IL\text{-}10_{subject}$ is the amount of IL-10 in serum from the subject prior to administration of the first amount, the third amount, the fifth amount or the seventh amount of recombinant polypeptide or the nucleic acid and $IL\text{-}10_{healthy}$ is the amount of IL-10 in serum from a healthy subject. In one aspect, any of the first amount, the second amount, the third amount and/or the fourth amount of the agent is selected from about 25 μg/m² when the ratio is about 1.09 to about 1.13, about 50 μg/m² when the ratio is about 1.23 to about 1.27, about 75 μg/m² when the ratio is about 1.30 to about 1.35, about 100 μg/m² when the ratio is about 1.40 to about 1.45, about 150 μg/m² when the ratio is about 1.80 to about 1.85, about 300 μg/m² when the ratio is about 2.80 to about 2.90 or about 600 μg/m² when the ratio is about 7.10 to about 7.20.

In one aspect, any of the first amount, the second amount, the third amount and/or the fourth amount of the agent is selected based on the ratio: $IL\text{-}10_{subject}$:$IL\text{-}10_{healthy}$, wherein $IL\text{-}10_{subject}$ is the amount of IL-10 in serum from the subject prior to administration of the first amount, the third amount, the fifth amount or the seventh amount of recombinant polypeptide or the nucleic acid and $IL\text{-}10_{healthy}$ is the amount of IL-10 in serum from a healthy subject. In one aspect, any of the first amount, the second amount, the third amount and/or the fourth amount of the agent is selected from about 25 μg/m² when the ratio is about 1.11, about 50 μg/m² when the ratio is about 1.25, about 75 μg/m² when the ratio is about 1.33, about 100 μg/m² when the ratio is about 1.43, about 150 μg/m² when the ratio is about 1.82, about 300 μg/m² when the ratio is about 2.86 or about 600 μg/m² when the ratio is about 7.14.

In one aspect, wherein the first amount of the agent, the second amount of the agent, the third amount of the agent and the fourth amount of the agent are administered via intravenous injection or intraperitoneal injection. In one aspect, the agent that reduces IL-10 is an interferon gamma (IFNg), an IFNg mimetic, an IFNg agonist or a combination thereof. In one aspect, the agent that reduces IL-10 is IFNg. In one aspect, the agent that reduces IL-10 is formulated with a pharmaceutically acceptable carrier.

In one aspect, the first amount of recombinant polypeptide or the nucleic acid is effective to obtain an amount of C-Reactive Protein (CRP) in the blood from the subject of between about 170 mg/L to about 220 mg/L. In one aspect, the first amount of the recombinant polypeptide is between about 18 mg/kg to about 22 mg/kg. In one aspect, the first amount of the recombinant polypeptide is between 19.5-21.4 mg/kg. In one aspect, the first amount of the recombinant polypeptide is about 20 mg/kg.

In one aspect, the second amount of the recombinant polypeptide is effective to obtain an amount of C-Reactive Protein (CRP) in the blood from the subject of between about 130 mg/L to about 180 mg/L. In one aspect, the second amount of the recombinant polypeptide is between about 11 mg/kg to about 16 mg/kg. In one aspect, the second amount of the recombinant polypeptide is between 12.9-14.1 mg/kg. In one aspect, the second amount of the recombinant polypeptide is about 13.5 mg/kg.

In one aspect, the third amount of the recombinant polypeptide or the nucleic acid is determined by
a) determining the constants a and b in the following system of equations:

$$CRP_1 = a \times Amount_1 + b$$

$$CRP_1 = a \times Amount_1 + b$$
$$CRP_2 - CRP_1/8 = a \times Amount_2 + b$$

wherein $CRP_1$ is the amount of CRP in blood from the subject about 20 hours after the administration of the first amount of the recombinant polypeptide or the nucleic acid, $CRP_2$ is the amount of CRP in blood from the subject about 20 hours after the administration of the second amount of the recombinant polypeptide or the nucleic acid, $Amount_1$ is the first amount of the recombinant polypeptide or the nucleic acid and $Amount_2$ is the second amount of the recombinant polypeptide or the nucleic acid; and
b) determining the third amount of the recombinant polypeptide or the nucleic acid, $Amount_3$, wherein $$Amount_3 = \frac{CRP^{Optimal_1} - b}{a},$$

wherein $CRP^{Optimal_1}$ is the intended optimal amount of CRP present in the blood of the subject after administration of the third amount of the recombinant polypeptide or the nucleic acid,
wherein the $CRP_1$ and $CRP_2$ is measured in mg/L.

In one aspect, the $CRP^{Optimal_1}$ is between about 170 mg/L to about 220 mg/L. In one aspect, the $CRP^{Optimal_1}$ is between about 200 mg/L to about 220 mg/L.

In one aspect, the fourth amount of the recombinant polypeptide or the nucleic acid is determined by:
a) determining the constants a and b in the following system of equations:

$$CRP_1 = a \times Amount_1 + b$$

$$CRP_1 = a \times Amount_1 + b$$
$$CRP_2 - CRP_1/8 = a \times Amount_2 + b$$

wherein $CRP_1$ is the amount of CRP in blood from the subject about 20 hours after the administration of the first amount of the recombinant polypeptide or the nucleic acid, $CRP_2$ is the amount of CRP in blood from the subject about 20 hours after the administration of the second amount of the recombinant polypeptide or the nucleic acid, $Amount_1$ is the first amount of the recombinant polypeptide or the nucleic acid and $Amount_2$ is the second amount of the recombinant polypeptide or the nucleic acid; b) determining the fourth amount, $Amount_4$, wherein $$Amount_4 = \frac{(CRP^{Optimal_2} - CRP^{Optimal_1}/8) - b}{a}$$

wherein $CRP_1$ and $CRP_2$ is measured in mg/L.

In one aspect, the $CRP^{Optimal_2}$ is between about 130 mg/L to about 180 mg/L. In one aspect, the $CRP^{Optimal_2}$ is between about 159 mg/mL to about 169 mg/mL.

In one aspect, the fifth amount of the recombinant polypeptide or the nucleic acid is the same as the third amount of the recombinant polypeptide or the nucleic acid. In one aspect, the sixth amount of the recombinant polypeptide or the nucleic acid is the same as the fourth amount of the recombinant polypeptide or the nucleic acid. In one aspect, the seventh amount of the recombinant polypeptide or the nucleic acid is the same as the third amount of the recombinant polypeptide or the nucleic acid. In one aspect, the eighth amount of the recombinant polypeptide or the nucleic acid is the same as the fourth amount of the recombinant polypeptide or the nucleic acid.

In one aspect, any of the first amount of the recombinant polypeptide or the nucleic acid, the second amount of the recombinant polypeptide or the nucleic acid, the third amount of the recombinant polypeptide or the nucleic acid, the fourth amount of the recombinant polypeptide or the nucleic acid, the fifth amount of the recombinant polypeptide or the nucleic acid, the sixth amount of the recombinant polypeptide or the nucleic acid, the seventh amount of the recombinant polypeptide or the nucleic acid and the eighth amount of the recombinant polypeptide or the nucleic acid are administered via intravenous injection or intraperitoneal injection.

In one aspect, the cancer is a recurrence of an earlier presentation of cancer. In one aspect, the cancer is a metastasis of an earlier presentation of cancer. In one aspect, the cancer is a more severe subtype or more severe presentation of an earlier presentation of cancer. In one aspect, the subject has a recurrence of a cancer following a remission of the cancer. In one aspect, the cancer is a solid tumor cancer. In one aspect, the cancer is a breast cancer, a lung cancer or a colorectal cancer.

The present disclosure provides a method of treating cancer in a subject comprising a) administering a first amount of a recombinant polypeptide comprising an amino acid sequence having at least 95% sequence identity to the polypeptide of SEQ ID NO: 9, or a nucleic acid encoding the recombinant polypeptide comprising an amino acid sequence having at least 95% sequence identity to the polypeptide of SEQ ID NO: 9 to the subject; and b) administering a second amount of the recombinant polypeptide or the nucleic acid to the subject at least 20 hours after the administration of the first amount of the recombinant polypeptide or the nucleic acid. In one aspect, the second amount of the recombinant polypeptide or the nucleic acid in step b) is administered at least 24 hours after the administration of the first amount of recombinant polypeptide or the nucleic acid. In one aspect, the recombinant polypeptide comprises an amino acid sequence having at least 99% sequence identity to the polypeptide of SEQ ID NO: 9, or a nucleic acid encoding the recombinant polypeptide comprising an amino acid sequence having at least 99% sequence identity to the polypeptide of SEQ ID NO: 9.

In one aspect, the method of the disclosure further comprises c) administering a third amount of the recombinant polypeptide or the nucleic acid to the subject at least 72 hours after the administration of second amount of the recombinant polypeptide or the nucleic acid; and d) administering a fourth amount of the recombinant polypeptide or the nucleic acid to the subject at least 20 hours after the administration of the third amount of the recombinant polypeptide or the nucleic acid. In one aspect, the fourth amount of the recombinant polypeptide or the nucleic acid in step d) is administered at least 24 hours after the administration of the third amount of recombinant polypeptide or the nucleic acid.

In one aspect, the method of the disclosure further comprises e) administering a fifth amount of the recombinant polypeptide or the nucleic acid at least 72 hours after the administration of the fourth amount of the recombinant polypeptide or the nucleic acid; f) administering a sixth amount of the recombinant polypeptide or the nucleic acid to the subject at least 20 hours after the administration of the fifth amount of the recombinant polypeptide or the nucleic acid. In one aspect, the sixth amount of the recombinant polypeptide or the nucleic acid in step f) is administered at least 24 hours after the administration of the fifth amount of recombinant polypeptide or the nucleic acid.

In one aspect, the method of the disclosure further comprises administering a seventh amount of the recombinant polypeptide or the nucleic acid at least 72 hours after the administration of sixth amount of the recombinant polypeptide or the nucleic acid; h) administering a eighth amount of the recombinant polypeptide or the nucleic acid to the subject at least 20 hours after the administration of the seventh amount of the recombinant polypeptide or the nucleic acid. In one aspect the eighth amount of the recombinant polypeptide or the nucleic acid in step h) is administered at least 24 hours after the administration of the seventh amount of recombinant polypeptide or the nucleic acid.

In one aspect, the first amount of the recombinant polypeptide is between about 18 mg/kg to about 22 mg/kg. In one aspect, the first amount of the recombinant polypeptide is between 19.5-21.4 mg/kg. In one aspect, the first amount of the recombinant polypeptide is about 20 mg/kg. In one aspect the second amount of the recombinant polypeptide is between about 11 mg/kg to about 16 mg/kg. In one aspect, the second amount of the recombinant polypeptide is between 12.9-14.1 mg/kg. In one aspect, second amount of the recombinant polypeptide is about 13.5 mg/kg.

In one aspect, the third amount of the recombinant polypeptide is determined by:

a) determining the constants a and b in the following system of equations:

$$CRP_1 = a \times Amount_1 + b$$

$$CRP_1 = a \times Amount_1 + b$$
$$CRP_2 - CRP_1/8 = a \times Amount_2 + b$$

wherein $CRP_1$ is the amount of CRP in blood from the subject about 20 hours after the administration of the first amount of the recombinant polypeptide, $CRP_2$ is the amount of CRP in blood from the subject about 20 hours after the administration of the second amount of the recombinant polypeptide, $Amount_1$ is the first amount of the recombinant polypeptide and $Amount_2$ is the second amount of the recombinant polypeptide; b) determining the third amount of the recombinant polypeptide, $Amount_3$, wherein $$Amount_3 = \frac{CRP^{Optimal1} - b}{a},$$

wherein $CRP^{Optimal_1}$ is the intended optimal amount of CRP present in the blood of the subject after administration of the third amount of the recombinant polypeptide wherein the $CRP_1$ and $CRP_2$ is measured in mg/L.

In one aspect, the $CRP^{Optimal_1}$ is between about 170 mg/L to about 220 mg/L. In one aspect, the $CRP^{Optimal_1}$ is between about 200 mg/L to about 220 mg/L.

In one aspect, the fourth amount of the recombinant polypeptide is determined by:
a) determining the constants a and b in the following system of equations:

$$CRP_1 = a \times Amount_1 + b$$
$$CRP_2 - CRP_1/8 = a \times Amount_2 + b$$

wherein $CRP_1$ is the amount of CRP in blood from the subject about 20 hours after the administration of the first amount of the recombinant polypeptide, $CRP_2$ is the amount of CRP in blood from the subject about 20 hours after the administration of the second amount of the recombinant polypeptide, $Amount_1$ is the first amount of the recombinant polypeptide and $Amount_2$ is the second amount of the recombinant polypeptide; b) determining the fourth amount, $Amount_4$, wherein $$Amount_4 = \frac{(CRP^{Optimal_2} - CRP^{Optimal_1}/8) - b}{a};$$

wherein the $CRP_1$ and $CRP_2$ is measured in mg/L.

In one aspect, the $CRP^{Optimal_2}$ is between about 130 mg/L to about 180 mg/L. In one aspect, the $CRP^{Optimal_2}$ is between about 159 mg/mL to about 169 mg/mL.

In one aspect, the fifth amount of the recombinant polypeptide is the same as the third amount of the recombinant polypeptide. In one aspect, the sixth amount of the recombinant polypeptide is the same as the fourth amount of the recombinant polypeptide.

In one aspect, the seventh amount of the recombinant polypeptide is the same as the third amount of the recombinant polypeptide. In one aspect, the eighth amount of the recombinant polypeptide is the same as the fourth amount of the recombinant polypeptide.

In one aspect, any of the first amount of the recombinant polypeptide, the second amount of the recombinant polypeptide, the third amount of the recombinant polypeptide, the fourth amount of the recombinant polypeptide, the fifth amount of the recombinant polypeptide, the sixth amount of the recombinant polypeptide, the seventh amount of the recombinant polypeptide and/or the eighth amount of the recombinant polypeptide are administered via intravenous or intraperitoneal injection. In one aspect, the recombinant polypeptide is formulated with a pharmaceutically acceptable carrier.

In one aspect, the cancer is a recurrence of an earlier presentation of cancer. In one aspect, the cancer is a metastasis of an earlier presentation of cancer. In one aspect, the cancer is a more severe subtype or more severe presentation of an earlier presentation of cancer. In one aspect, the subject has a recurrence of a cancer following a remission of the cancer. In one aspect, the cancer is a solid tumor cancer. In one aspect, the cancer is a breast cancer, a lung cancer or a colorectal cancer.

The present disclosure provides a method of treating cancer in a subject in need thereof comprising: a) administering a first amount of an immunotherapy agent effective to obtain an amount of C-Reactive Protein (CRP) in blood from the subject between about 170 mg/L to about 220 mg/L; and b) administering at least a second amount of the immunotherapy agent to the subject at least 12 hours after the administration of the first amount, wherein the second amount is effective to obtain an amount of CRP in blood from the subject between about 130 mg/L to about 180 mg/L, thereby treating cancer in the subject.

In one aspect, the first amount of the immunotherapy agent is effective to obtain an amount of CRP in blood from the subject between about 180 mg/L to about 220 mg/L. In one aspect, the first amount of the immunotherapy agent is effective to obtain an amount of CRP in blood from the subject between about 190 mg/L to about 220 mg/L. In one aspect, the first amount of the immunotherapy agent is effective to obtain an amount of CRP in blood from the subject between about 200 mg/L to about 220 mg/L.

In one aspect, the second amount of the immunotherapy agent is effective to obtain an amount of CRP in blood from the subject between about 140 mg/L to about 170 mg/L. In one aspect, the second amount of the immunotherapy agent is effective to obtain an amount of CRP in blood from the subject between about 150 mg/L to about 170 mg/L. In one aspect, the second amount of the immunotherapy agent is effective to obtain an amount of CRP in blood from the subject between about 159 mg/L to about 169 mg/L. In one aspect, the second amount of the immunotherapy agent is administered to the subject at least 20 hours after the administration of the first amount.

In one aspect, the second amount of the immunotherapy agent is administered to the subject at least 24 hours after the administration of the first amount.

In one aspect, the first amount of the immunotherapy agent is effective to initiate an immune response against the cancer within the subject. In one aspect, the second amount of the immunotherapy agent is effective to initiate an immune response or maintain an immune response against the cancer within the subject. In one aspect, the immune response against the cancer comprises dendritic cell activation and/or macrophage activation.

In one aspect, the first amount of the immunotherapy agent does not induce life threatening adverse events within the subject. In one aspect, the second amount of the immunotherapy agent does not induce hypercytokinemia nor life threatening adverse events within the subject.

In one aspect, the immunotherapy agent is a recombinant polypeptide, a nucleic acid encoding a recombinant polypeptide, an antibody, a checkpoint inhibitor, an interferon, an interleukin, an oncolytic virus, a chimeric antigen receptor (CAR) T cell, a T-cell Receptor (TCR) T cell, a cancer vaccine, or a combination thereof.

In one aspect, the immunotherapy agent is a recombinant polypeptide comprising an amino acid sequence having at least 95% sequence identity to the polypeptide of SEQ ID NO: 9, or a nucleic acid encoding the recombinant polypeptide comprising an amino acid sequence having at least 95% sequence identity to the polypeptide of SEQ ID NO: 9.

In one aspect, the immunotherapy agent is a recombinant polypeptide comprising an amino acid sequence having at least 95% sequence identity to the polypeptide of SEQ ID NO: 9, or a nucleic acid encoding the recombinant polypeptide comprising an amino acid sequence having at least 95% sequence identity to the polypeptide of SEQ ID NO: 9.

In one aspect, wherein the immunotherapy agent is administered via intravenous injection, arterial injection, intraperitoneal injection, subcutaneous injection, orally or a combination thereof. In one aspect, the immunotherapy agent is administered intratumorally, locally to the site of the tumor or to a lymph node associated with the tumor.

In one aspect, the method further comprises administering an agent that reduces IL-10 in the subject prior to administration of the first amount of the immunotherapy agent. In one aspect, the agent that reduces IL-10 is administered between 2-24 hours before the administration of the first amount of the immunotherapy agent. In one aspect, the agent that reduces IL-10 is an interferon gamma (IFNg), an IFNg mimetic, an IFNg agonist, or a combination thereof. In one aspect, the agent that reduces IL-10 is administered via intravenous injection, arterial injection, intraperitoneal injection, subcutaneous injection, orally or a combination thereof.

In one aspect, the cancer is a solid tumor cancer. In one aspect, the cancer is a hematologic cancer. In one aspect, the cancer is a recurrence of an earlier presentation of cancer. In one aspect, the cancer is metastatic cancer.

The present disclosure provides a recombinant polypeptide comprising an amino acid sequence having at least 95% sequence identity to the polypeptide of SEQ ID NO: 9, or a nucleic acid encoding the recombinant polypeptide comprising an amino acid sequence having at least 95% sequence identity to the polypeptide of SEQ ID NO: 9, for use in a method of treating cancer, wherein the method of treating comprises a) administering a first amount of an agent that reduces IL-10 to the subject; b) administering a first amount of the recombinant polypeptide or the nucleic acid to the subject between 2-24 hours after the administration of the first amount of the agent; and c) administering a second amount of the recombinant polypeptide or the nucleic acid to the subject at least 20 hours after the administration of the first amount of the recombinant polypeptide or the nucleic acid.

The present disclosure provides a recombinant polypeptide comprising an amino acid sequence having at least 95% sequence identity to the polypeptide of SEQ ID NO: 9, for use in a method of treating cancer, wherein the method of treating comprises a) administering a first amount of an agent that reduces IL-10 to the subject; b) administering a first amount of the recombinant polypeptide to the subject between 2-24 hours after the administration of the first amount of the agent; and c) administering a second amount of the recombinant polypeptide to the subject at least 20 hours after the administration of the first amount of the recombinant polypeptide.

The present disclosure provides a nucleic acid encoding a recombinant polypeptide comprising an amino acid sequence having at least 95% sequence identity to the polypeptide of SEQ ID NO: 9, for use in a method of treating cancer, wherein the method of treating comprises administering a first amount of an agent that reduces IL-10 to the subject; b) administering a first amount of the nucleic acid to the subject between 2-24 hours after the administration of the first amount of the agent; and c) administering a second amount of the nucleic acid to the subject at least 20 hours after the administration of the first amount of the nucleic acid.

The present disclosure provides an agent that reduces IL-10 for use in a method of treating cancer, wherein the method of treating comprises a) administering a first amount of the agent to the subject; b) administering a first amount of a recombinant polypeptide comprising an amino acid sequence having at least 95% sequence identity to the polypeptide of SEQ ID NO: 9, or a nucleic acid encoding the recombinant polypeptide comprising an amino acid sequence having at least 95% sequence identity to the polypeptide of SEQ ID NO: 9 to the subject between 2-24 hours after the administration of the first amount of the agent; and c) administering a second amount of the recombinant polypeptide or the nucleic acid to the subject at least 20 hours after the administration of the first amount of the recombinant polypeptide or the nucleic acid.

In one aspect, the recombinant polypeptide, the nucleic acid, or the agent for use in the method of treating cancer comprises the first amount of the recombinant polypeptide or the nucleic acid of b) is administered to the subject at about 3-4 hours after the administration of the first amount of the agent; and the second amount of the recombinant polypeptide or the nucleic acid of c) is administered to the subject at least 24 hours after the administration of the first amount of the recombinant polypeptide or the nucleic acid.

In one aspect, the recombinant polypeptide, the nucleic acid, or the agent for use in the method of treating cancer further comprises d) administering a second amount of the agent to the subject; e) administering a third amount of the recombinant polypeptide or the nucleic acid to the subject between 2-24 hours or between 3-4 hours after the administration of the second amount of the agent to the subject; and f) administering a fourth amount of the recombinant polypeptide or the nucleic acid to the subject at least 20 hours or at least 24 hours after the administration of the third amount of the recombinant polypeptide or the nucleic acid to the subject.

In one aspect, the recombinant polypeptide, nucleic acid, or agent for use in the method of treating cancer, further comprises g) administering a third amount of the agent to the subject; h) administering a fifth amount of the recombinant polypeptide or the nucleic acid between 2-24 hours or about 3-4 hours after the administration of the third amount of the agent; and i) administering a sixth amount of the recombinant polypeptide or the nucleic acid to the subject at least 20 hours or at least 24 hours after the administration of the fifth amount of the recombinant polypeptide or the nucleic acid; and optionally further comprises j) administering a fourth amount of the agent to the subject; k) administering a seventh amount of the recombinant polypeptide or the nucleic acid at between 2-24 hours or about 3-4 hours after the administration of the fourth amount of the agent; and 1) administering a eighth amount of the recombinant polypeptide or the nucleic acid to the subject at least 20 hours or at least 24 hours after the administration of the seventh amount of the recombinant polypeptide or the nucleic acid.

In one aspect, the first amount, the second amount, the third amount and/or the fourth amount of the agent selected based on the ratio: IL-10$_{subject}$:IL-10$_{healthy}$, wherein IL-10$_{subject}$ is the amount of IL-10 in serum from the subject prior to administration of any of the first amount, the second amount, the third amount or the fourth amount of recombinant polypeptide or the nucleic acid and IL-10$_{healthy}$ is the amount of IL-10 in serum from a healthy subject; optionally wherein any of the first amount, the second amount, the third amount or the fourth amount of the agent is about 25 µg/m$^2$ when the ratio is about 1.09 to about 1.13, is about 50 µg/m$^2$ when the ratio is about 1.23 to about 1.27, is about 75 µg/m$^2$ when the ratio is about 1.30 to about 1.35, is about 100 µg/m$^2$ when the ratio is about 1.40 to about 1.45, is about 150 µg/m$^2$ when the ratio is about 1.80 to about 1.85, is about 300 µg/m² when the ratio is about 2.80 to about 2.90, or is about 600 µg/m² when the ratio is about 7.10 to about 7.20.

In one aspect, the first amount, the second amount, the third amount and/or the fourth amount of the agent selected based on the ratio: IL-10$_{subject}$:IL-10$_{healthy}$, wherein IL-10$_{subject}$ is the amount of IL-10 in serum from the subject prior to administration of any of the first amount, the second amount, the third amount or the fourth amount of recombinant polypeptide or the nucleic acid and IL-10$_{healthy}$ is the amount of IL-10 in serum from a healthy subject; optionally wherein any of the first amount, the second amount, the third amount or the fourth amount of the agent is about 25 µg/m² when the ratio is about 1.11, is about 50 µg/m² when the ratio is about 1.25, is about 75 µg/m² when the ratio is about 1.33, is about 100 µg/m² when the ratio is about 1.43, is about 150 µg/m² when the ratio is about 1.82, is about 300 µg/m² when the ratio is about 2.86, or is about 600 µg/m² when the ratio is about 7.14.

In one aspect, (1) the first amount of recombinant polypeptide is effective to obtain an amount of C-Reactive Protein (CRP) in the blood from the subject of between about 170 mg/L to about 220 mg/L, and wherein the first amount of the recombinant polypeptide is between 19.5-21.4 mg/kg; optionally wherein the first amount of the recombinant polypeptide is about 20 mg/kg; and/or (2) the second amount of the recombinant polypeptide is effective to obtain an amount of CRP in the blood from the subject of between about 130 mg/L to about 180 mg/L, and wherein the second amount of the recombinant polypeptide is between 12.9-14.1 mg/kg; optionally wherein the second amount of the recombinant polypeptide is about 13.5 mg/kg.

In one aspect, any of the first amount of the agent, the second amount of the agent, the third amount of the agent, and/or the fourth amount of the agent are administered via intravenous injection or intraperitoneal injection.

In one aspect, the agent that reduces IL-10 is an interferon gamma (IFNg), an IFNg mimetic, an IFNg agonist or a combination thereof, optionally wherein the agent that reduces IL-10 is IFNg.

The present disclosure provides a recombinant polypeptide comprising an amino acid sequence having at least 95% sequence identity to the polypeptide of SEQ ID NO: 9, or a nucleic acid encoding the recombinant polypeptide comprising an amino acid sequence having at least 95% sequence identity to the polypeptide of SEQ ID NO: 9, for use in a method of treating cancer comprising a) administering a first amount of the recombinant polypeptide or the nucleic acid to the subject; and b) administering a second amount of the recombinant polypeptide or the nucleic acid to the subject at least 20 hours after the administration of the first amount of the recombinant polypeptide or the nucleic acid.

The present disclosure provides a recombinant polypeptide comprising an amino acid sequence having at least 95% sequence identity to the polypeptide of SEQ ID NO: 9, for use in a method of treating cancer comprising a) administering a first amount of the recombinant polypeptide to the subject; and b) administering a second amount of the recombinant polypeptide to the subject at least 20 hours after the administration of the first amount of the recombinant polypeptide.

The present disclosure provides a nucleic acid encoding a recombinant polypeptide comprising an amino acid sequence having at least 95% sequence identity to the polypeptide of SEQ ID NO: 9, for use in a method of treating cancer comprising a) administering a first amount of the nucleic acid to the subject; and b) administering a second amount of the nucleic acid to the subject at least 20 hours after the administration of the first amount of the nucleic acid.

In one aspect, the second amount of the recombinant polypeptide or the nucleic acid in step b) is administered at least 24 hours after the administration of the first amount of recombinant polypeptide or the nucleic acid.

In one aspect, the recombinant polypeptide or nucleic acid for use in the method of treating cancer, the method further comprises c) administering a third amount of the recombinant polypeptide or the nucleic acid to the subject at least 72 hours after the administration of second amount of the recombinant polypeptide or the nucleic acid; and d) administering a fourth amount of the recombinant polypeptide or the nucleic acid to the subject at least 20 hours or at least 24 hours after the administration of the third amount of the recombinant polypeptide or the nucleic acid.

In one aspect, (1) the first amount of the recombinant polypeptide is: between 19.5-21.4 mg/kg, or about 20 mg/kg; and/or (2) the second amount of the recombinant polypeptide is between 12.9-14.1 mg/kg, or about 13.5 mg/kg.

In one aspect, (1) the third amount of the recombinant polypeptide or the nucleic acid is determined by: a) determining the constants a and b in the following system of equations:

$$CRP_1 = a \times \text{Amount}_1 + b$$
$$CRP_2 - CRP_1/8 = a \times \text{Amount}_2 + b$$

wherein $CRP_1$ is the amount of C-Reactive Protein (CRP) in blood from the subject about 20 hours after the administration of the first amount of the recombinant polypeptide or the nucleic acid, $CRP_2$ is the amount of CRP in blood from the subject about 20 hours after the administration of the second amount of the recombinant polypeptide or the nucleic acid, $\text{Amount}_1$ is the first amount of the recombinant polypeptide and $\text{Amount}_2$ is the second amount of the recombinant polypeptide or the nucleic acid;
b) determining the third amount of the recombinant polypeptide or the nucleic acid, $\text{Amount}_3$, wherein $$\text{Amount}_3 = \frac{CRP^{Optimal_1} - b}{a},$$

wherein $CRP^{Optimal_1}$ is the intended optimal amount of CRP present in the blood of the subject after administration of the third amount of the recombinant polypeptide or the nucleic acid; wherein the $CRP_1$ and $CRP_2$ is measured in mg/L; and wherein the $CRP^{Optimal_1}$ is between about 170 mg/L to about 220 mg/L; optionally wherein the $CRP^{Optimal_1}$ is between about 200 mg/L to about 220 mg/L; and/or
(2) the fourth amount of the recombinant polypeptide or the nucleic acid is determined by:
a) determining the constants a and b in the following system of equations:

$$CRP_1 = a \times \text{Amount}_1 + b$$
$$CRP_2 - CRP_1/8 = a \times \text{Amount}_2 + b$$

wherein CRP₁ is the amount of CRP in blood from the subject about 20 hours after the administration of the first amount of the recombinant polypeptide or the nucleic acid, CRP₂ is the amount of CRP in blood from the subject about 20 hours after the administration of the second amount of the recombinant polypeptide or the nucleic acid, Amount₁ is the first amount of the recombinant polypeptide or the nucleic acid and Amount₂ is the second amount of the recombinant polypeptide or the nucleic acid;
b) determining the fourth amount, Amount₄, wherein $$Amount_4 = \frac{(CRP^{Optimal_2} - CRP^{Optimal_1}/8) - b}{a};$$

wherein the CRP₁ and CRP₂ is measured in mg/L and wherein the $CRP^{Optimal2}$ is between about 130 mg/mL to about 180 mg/mL; optionally wherein the $CRP^{Optimal2}$ is between about 159 mg/mL to about 169 mg/mL.

In one aspect, (1) the fifth amount of the recombinant polypeptide or the nucleic acid is the same as the third amount of the recombinant polypeptide or the nucleic acid; and/or (2) the sixth amount of the recombinant polypeptide or the nucleic acid is the same as the fourth amount of the recombinant polypeptide or the nucleic acid; and/or (3) the seventh amount of the recombinant polypeptide or the nucleic acid is the same as the third amount of the recombinant polypeptide or the nucleic acid; and/or (4) the eighth amount of the recombinant polypeptide or the nucleic acid is the same as the fourth amount of the recombinant polypeptide or the nucleic acid.

In one aspect, any of the first amount, the second amount, the third amount, the fourth amount, the fifth amount, the sixth amount, the seventh amount and/or the eighth amount of the recombinant polypeptide or the nucleic acid are administered via intravenous injection or intraperitoneal injection.

In one aspect, (1) the recombinant polypeptide comprises an amino acid sequence having at least 99% sequence identity to the polypeptide of SEQ ID NO: 9, or a nucleic acid encoding the recombinant polypeptide comprising an amino acid sequence having at least 99% sequence identity to the polypeptide of SEQ ID NO: 9; or (2) the recombinant polypeptide comprises an amino acid sequence of SEQ ID NO: 9, or a nucleic acid encoding the recombinant polypeptide comprising an amino acid sequence of SEQ ID NO: 9.

In one aspect, the cancer is a recurrence of an earlier presentation of cancer, a metastasis of an earlier presentation of cancer, a more severe subtype or more severe presentation of an earlier presentation of cancer, a recurrence of a cancer following a remission of the cancer, a solid tumor cancer, a breast cancer, a lung cancer, or a colorectal cancer.

In one aspect, the recombinant polypeptide or the nucleic acid for use in a method of treating cancer comprises administering a first amount of an agent that reduces IL-10 to the subject between 2-24 hours before the administration of the first amount of the recombinant polypeptide or the nucleic acid.

The present disclosure provides an immunotherapy agent for use in a method of treating cancer, wherein the method of treating comprises a) administering a first amount of the immunotherapy agent effective to obtain an amount of C-Reactive Protein (CRP) in blood from the subject between about 170 mg/L to about 220 mg/L; and b) administering at least a second amount of the immunotherapy agent to the subject at least 12 hours after the administration of the first amount, wherein the second amount is effective to obtain an amount of CRP in blood from the subject between about 130 mg/L to about 180 mg/L.

In one aspect, the first amount of the immunotherapy agent is effective to obtain an amount of CRP in blood from the subject between about 180 mg/L to about 220 mg/L, optionally wherein the amount is between about 190 mg/L to about 220 mg/L, or optionally wherein the amount is between about 200 mg/L to about 220 mg/L. In one aspect, the second amount of the immunotherapy agent is effective to obtain an amount of CRP in blood from the subject between about 140 mg/L to about 170 mg/L, optionally wherein the amount is between about 150 mg/L to about 170 mg/L, or optionally wherein the amount is between about 159 mg/L to about 169 mg/L.

In one aspect, the second amount of the immunotherapy agent is administered to the subject at least 20 hours after the administration of the first amount or at least 24 hours after the administration of the first amount.

In one aspect, the first amount of the immunotherapy agent is effective to initiate an immune response against the cancer, the second amount of the immunotherapy agent is effective to initiate an immune response or maintain an immune response against the cancer, or a combination thereof.

In one aspect, the immune response against the cancer comprises dendritic cell activation and/or macrophage activation.

In one aspect, the first amount of the immunotherapy agent does not induce a life threatening adverse event within the subject. In one aspect, the second amount of the immunotherapy agent does not induce hypercytokinemia nor a life threatening adverse event within the subject.

In one aspect, the immunotherapy agent is a recombinant polypeptide or a nucleic acid encoding a recombinant polypeptide, an antibody, a checkpoint inhibitor, an interferon, an interleukin, an oncolytic virus, a chimeric antigen receptor (CAR) T cell, a T-cell Receptor (TCR) T cell, a cancer vaccine, or a combination thereof.

In one aspect, the method for treating cancer, further comprises administering an agent that reduces IL-10 in the subject prior to administration of the first amount of the immunotherapy agent.

In one aspect, the agent that reduces IL-10 is administered between 2-24 hours before the administration of the first amount of the immunotherapy agent. In one aspect, the agent that reduces IL-10 is an interferon gamma (IFNg), an IFNg mimetic, an IFNg agonist, or a combination thereof.

Any of the above aspects can be combined with any other aspect.

Unless otherwise defined, all technical and scientific terms used herein have the same meaning as commonly understood by one of ordinary skill in the art to which this disclosure belongs.

As used herein, the singular forms of a word also include the plural form of the word, unless the context clearly dictates otherwise; as examples, the terms "a," "an," and "the" are understood to be singular or plural and the term "or" is understood to be inclusive. By way of example, "an element" means one or more element.

Throughout the specification the word "comprising," or variations such as "comprises," will be understood to imply the inclusion of a stated element, integer or step, or group of elements, integers or steps, but not the exclusion of any other element, integer or step, or group of elements, integers or steps. Throughout the specification the word "consisting of,"

or variations such as "consists of," will be understood to imply the inclusion of a stated element, integer or step, or group of elements, integers or steps, and the exclusion of any other element, integer or step, or group of elements, integers or steps. Throughout the specification the word "consisting essentially of," or variations such as "consists essentially of," will be understood to imply the inclusion of a stated element, integer or step, or group of elements, integers or steps, and any other element, integer or step, or group of elements, integers or steps that do not materially affect the basic and novel characteristics of the claimed invention.

About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed disclosure. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

FIG. 4A shows a bar graph quantifying the percentage of cells that express CRT following treatment of H460 human lung cancer cell lines (HTB-177, ATCC) with various concentrations of CRYA_1B recombinant polypeptide (SEQ ID NO: 9). The stock CRYA_1B recombinant polypeptide (SEQ ID NO: 9) was diluted to the final concentration of 0.1, 1, 10, 25, 35, 50 µg/ml and the H460 cells were incubated for 30 minutes at 37° C. The CRT-expressing H460 cells were determined by FACSCalibur (BD Biosciences) flow cytometry using CRT mAb (Abcam). FIG. 4B shows the flow cytometry profiles used for quantification.

FIG. 5B shows the flow cytometry profiles used for quantification.

FIG. 15B shows the flow cytometry profiles used for quantification.

FIG. 16B shows the flow cytometry profiles used for quantification.

FIG. 21 shows a line graph of the levels of CRP/SAP following treatment with recombinant polypeptide CRYA_1B (SEQ ID NO: 9). Blood was sampled in 20 hrs after recombinant polypeptide CRYA_1B treatment to MC38 tumour-bearing mice (n=2 mice for each dose). SAP was determined by Luminex assays. Treatment with recombinant polypeptide CRYA_1B (SEQ ID NO: 9) (mg/kg) correlates linearly with the CRP/SAP level (mg/L) with the equation of the line as y=10.4x−2.6. 200 mg/L<= $CRP/SAP^{optimal\_d}$ <=220 mg/L; 159 mg/L<=$CRP/SAP^{optimal\_d+1}$<=169 mg/L.

FIG. 24 shows a schematic diagram of a murine dosage regimen for CRYA_1B recombinant polypeptide (SEQ ID NO: 9). C57BL/6 are challenged with 1×10$^6$ cell inoculation of MC38, E0771 and B16F10 cells, respectively. Blue arrows indicated the timing of the intraperitoneal or intravenous injection of the recombinant polypeptide. Orange arrows indicate the timing of the intraperitoneal or intravenous injection of IFNg injection. Mice with a complete response after the first treatment regimen are subjected to a rechallenge using an inoculation of 2×10$^5$ cells of the same cell type prior to the first treatment regimen.

FIG. 25A shows a MC38 tumour volume (mm$^3$) and complete response (CR) rate after recombinant polypeptide and IFNg treatment regimen (starting on day 7, n=10 mice) or vehicle (n=5 mice) after MC38 tumour challenge (1×10$^6$ cells/mouse on day 0). FIG. 25B shows a MC38 tumour volume and relapse-free-survival (RFS) rate (n=12 CR mice pooled from two tumour challenge experiments) or vehicle (n=5 mice) after MC38 tumour rechallenge (2×10$^5$ cells/mouse on day 0: 6 months from CR). FIG. 25C shows a E0771 tumour volume and CR rate after recombinant polypeptide CRYA_1B/IFNg treatments (starting on day 10, n=10 mice) or vehicle (n=5 mice) after E0771 tumour challenge (1×10$^6$ cells/mouse on day 0). FIG. 25D shows a E0771 tumour volume and RFS rate (n=10 CR mice pooled from two tumour challenge experiments) or vehicle (n=5 mice) after E0771 tumour rechallenge (2×10$^5$ cells/mouse on day 0: 6 months from CR). Four independent experiments are shown in FIGS. 25A and 25C. Two independent experiments are shown in FIGS. 25C and 25D.

FIG. 26A B16F10 tumour volume and complete response (CR) rate after recombinant polypeptide CRYA_1B/IFNg treatments (starting on day 7, n=10 mice) or vehicle (n=5 mice) after B16F10 tumour challenge (1×10$^6$ cells/mouse on day 0). FIG. 26B B16F10 tumour volume and relapse-free-survival (RFS) rate (n=8 CR mice pooled from two tumour challenge experiments) or vehicle (n=5 mice) after B16F10 tumour rechallenge (2×10$^5$ cells/mouse on day 0: 6 months from CR). Four independent experiments are shown in FIG. 26A. Two independent experiments are shown in FIG. 26B.

FIG. 27 PBMC viability. PBMC were incubated in the absence or in the presence of various concentrations of recombinant polypeptide CRYA_1B for 3 hours 45 minutes. Afterwards, the cells were stained with CellEvent™ Caspase 3/7 and analysed by flow cytometry. The PBMC viability is the inverse of apoptosis. Results are one representative data from three independent experiments.

DETAILED DESCRIPTION OF THE INVENTION

Figure 1:
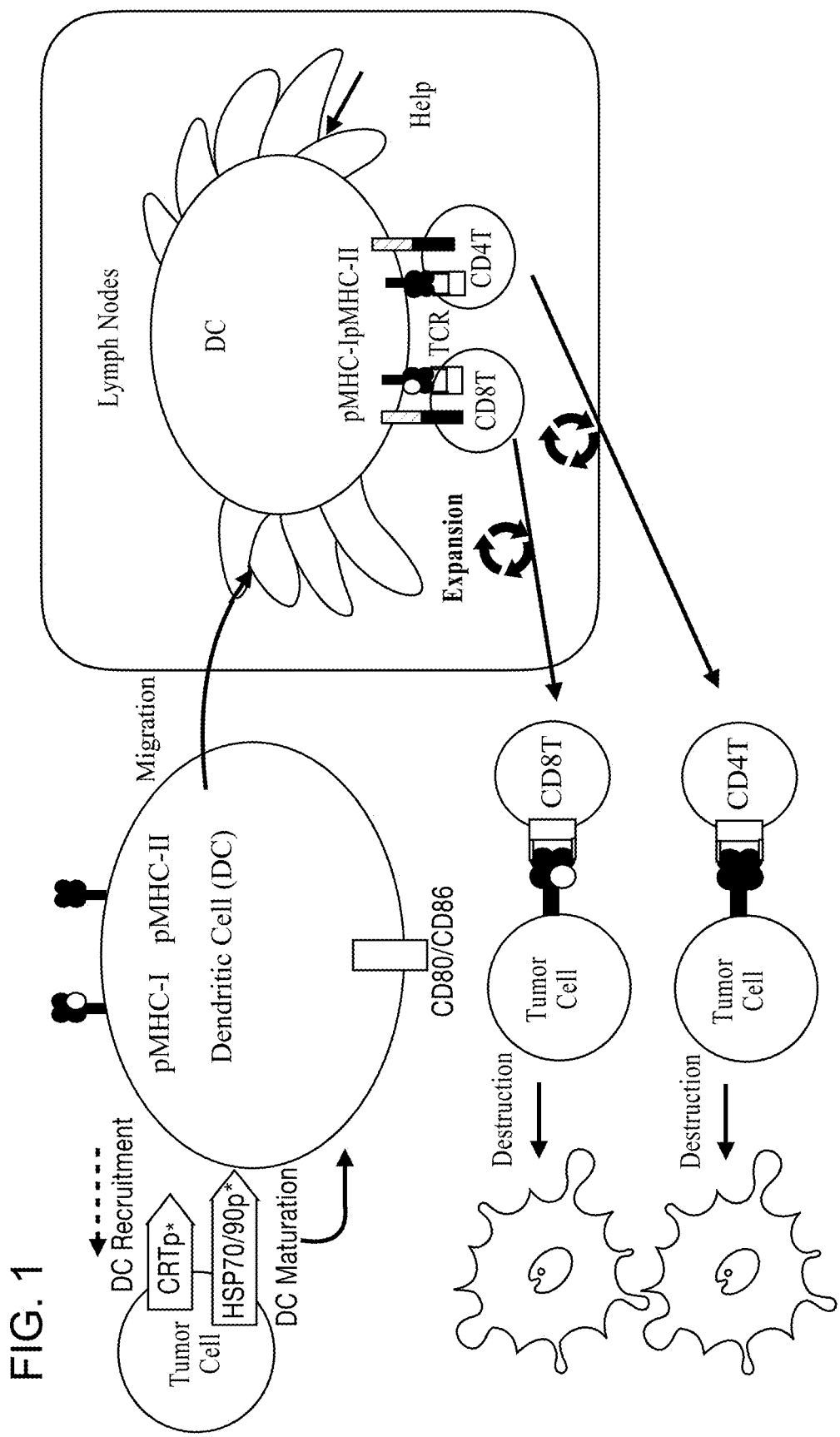
FIG. 1 is a schematic depiction of some characteristics of immunogenic cell death. Tumor cells marked for cell death have cell surface expression of pre-apoptotic Damage-Associated-Molecular-Pattern (DAMP) signals such as calreticulin (CRT), HSP70 and HSP90. Dendritic cells are activated upon the recognition of DAMP signals. Mature dendritic cells migrate to lymph nodes and can in turn prime CD4+ and CD8+ T-cells, which are important for mediating immunogenic cell death.

The present disclosure provides methods of preventing, delaying the progression of, treating or alleviating a symptom of, or otherwise ameliorating cancer in a subject by administering a recombinant polypeptide and an agent that reduces IL-10.

The present disclosure provides recombinant polypeptides that comprise, consist essentially of, or consist of, any of the amino acid sequences shown in Table 1A. The present disclosure also provides recombinant polypeptides comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

The present disclosure also provides acidic recombinant polypeptide variants that comprise, consist essentially of, or consist of, any of the amino acid sequences shown in Table 1A, wherein the recombinant polypeptide variant is acidic as determined by isoelectric point (pI). The present disclosure also provides acidic recombinant polypeptide variants comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

An "acidic variant" is a variant of a polypeptide of interest which is more acidic (e.g., as determined by calculation of pI) than the parent or original polypeptide of interest. The "pI" or "isoelectric point" of a polypeptide refers to the pH at which the polypeptide's positive charge balances its negative charge. pI can be calculated by any means known in the art, for example, from the net charge of the amino acid residues of the polypeptide or can be determined by isoelectric focusing.

In some aspects, an acidic variant is derived from the original parent sequence by making amino acid substitutions. A first mutational substitution is made by substituting any basic amino acid (K, R or H), neutral non-polar amino acid (G, A, V, L, I, M, F, W or P) or neutral polar amino acid (S, T, C, Y, N or Q) of the original parent sequence with an acidic amino acid (D or E). A second mutational substitution is made by making the inverse mutational substitution of the first mutational substitution. For example, all serine (S) residues from original parent sequence are substituted with glutamic acid (E) residues (first substitution). In addition, all glutamic acid (E) residues from the original parent sequence are substituted with serine (S) residues (second substitution). In one aspect, the inverse substitutions comprise, consist essentially of or consist of the mutation of all serine (S) residues of the original parent sequence to glutamic acid (E) and the mutation of all glutamic acid (E) residues of original parent sequence to serine (S) residues; the mutation of all serine (S) residues of the original parent sequence to aspartic acid (D) and the mutation of all aspartic acid (D) residues of the original parent sequence to serine (S) residues; the mutation of all valine (V) residues of the original parent sequence to aspartic acid (D) and the mutation of all aspartic acid (D) of the original parent sequence to valine (V) residues; or the mutation of all serine (S) residues of the original parent sequence to leucine (L) residues and the mutation of all leucine (L) residues of the original parent sequence to serine (S) residues. In a preferred aspect, the amino acid substitutions result in a recombinant polypeptide where aspartic acid (D), glutamic acid (E) and leucine (L) are each independently present in an amount greater than, or equal to, the amount of any other amino acid residue present within the recombinant polypeptide sequence. In a preferred aspect, the amino acid substitutions result in a recombinant polypeptide with leucine (L), aspartic acid (D) and glutamic acid (E) as the three most abundant amino acid residues of the acidic variant or as greater than or equal to in abundance to the next most abundant amino acid residue of the acidic variant. In some aspects, multiple inverse mutational substitutions of amino acids can be made.

The present disclosure also provides acidic recombinant polypeptide variants that comprise, consist essentially of, or consist of, any of the amino acid sequences shown in Table 1A, wherein the recombinant polypeptide variant is acidic as determined by isoelectric point (pI), wherein the pI of the recombinant peptide variant is lower than the pI of peptide sequence from which the recombinant peptide was derived, and wherein leucine (L), aspartic acid (D) and glutamic acid (E) are each independently present in an amount greater than, or equal to, the amount of any other amino acid residue present within the recombinant polypeptide sequence. The present disclosure also provides acidic recombinant polypeptide variants that comprise, consist essentially of, or consist of, any of the amino acid sequences shown in Table 1A, wherein the recombinant polypeptide variant is acidic as determined by isoelectric point (pI) and wherein leucine (L), aspartic acid (D) and glutamic acid (E) are the three most abundant amino acid residues of the acidic variant or are greater than or equal to in abundance to the next most abundant amino acid residue of the acidic variant. The present disclosure also provides acidic recombinant polypeptide variants comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

TABLE 1A

Recombinant Polypeptide Sequences

| Name | Amino Acid Sequence | SEQ ID NO: |
|---|---|---|
| *Anser cygnoides domesticus* CRYAA | MDITIQHPWFKRALGPLIPS RLFDQFFGEGLLEYDLLPLF SSTISPYYRQSLFRSVLESG ISEVRSDRDKFTIMLDVKHF SPEDLSVKIIDDFVEIHGKH SERQDDHGYISREFHRRYRL PANVDQSAITCSLSGDGMLT FSGPKVPSNMDPTHSERPIP VSREEKPTSAPSS | 1 |
| *Rhea americana* CRYAA | MDITIQHPWFKRALGPLIPS RLFDQFFGEGLLEYDLLPLF SSTISPYYRQSLFRSVLESG ISEVRSDREKFTIMLDVKHF SPEDLSVKIIDDFVEIHGKH SERQDDHGYISREFHRRYRL PSNVDQSAITCSLSSDGMLT FSGPKVQANMDPSHSERPIP VSREEKPTSAPSS | 2 |
| *Anas platyrhynchos* CRYAA | RALGPLIPSRLFDQFFGEGL LEYDLLPLFSSTISPYYRQS LFRSVLESGISEVRSDRDKF TIMLDVKHFSPEDLSVKIID DFVEIHGKHSERQDDHGYIS REFHRRYRLPANVDQSAITC SLSGDGMLTFSGPKVPSNMD PTHSERPIP | 3 |
| *Anas platyrhynchos* CRYAB | MDITIHNPLIRRPLFSWAP SRIFDQIFGEHLQESELLPA SPSLSPFLMRSPIFRMPSWL ETGLSEMRLEKDKFSVNLDV KHFSPEELKVKVLGDMVEIH GKHEERQDEHGFIAREFNRK | 4 |

TABLE 1A-continued

Recombinant Polypeptide Sequences

| Name | Amino Acid Sequence | SEQ ID NO: |
|---|---|---|
| | YRIPADVDPLTITSSLSLDG VLTVSAPRKQSDVPERSIPI TREEKPAIAGAQRK | |
| *Homo sapiens* CRYAA | MDVTIQHPWFKRTLGPFYPS RLFDQFFGEGLFEYDLLPFL SSTISPYYRQSLFRTVLDSG ISEVRSDRDKFVIFLDVKHF SPEDLTVKVQDDFVEIHGKH NERQDDHGYISREFHRRYRL PSNVDQSALSCSLSADGMLT FCGPKIQTGLDATHAERAIP VSREEKPTSAPSS | 5 |
| *Drosophila melanogaster* H5P23 | MANIPLLLSLADDLGRMSMV PFYEPYYCQRQRNPYLALVG PMEQQLRQLEKQVGASSGSS GAVSKIGKDGFQVCMDVSHF KPSELVVKVQDNSVLVEGNH EEREDDHGFITRHFVRRYAL PPGYEADKVASTLSSDGVLT IKVPKPPAIEDKGNERIVQI QQVGPAHLNVKENPKEAVEQ DNGNDK | 6 |
| *Drosophila melanogaster* H5P22 | MRSLPMFWRMAEEMARMPRL SSPFHAFFHEPPVWSVALPR NWQHIARWQEQELAPPATVN KDGYKLTLDVKDYSELKVKV LDESVVLVEAKSEQQEAEQG GYSSRHFLGRYVLPDGYEAD KVSSSLSDDGVLTISVPNPP GVQETLKEREVTIEQTGEPA KKSAEEPKDKTASQ | 7 |
| *Anser cygnoides domesticus* CRYAB | MDITIHNPLIRRPLFSWLAP SRIFDQIFGEHLQESELLPA SPSLSPFLMRSPIFRMPSWL ETGLSEMRLEKDKFSVNLDV KHFSPEELKVKVLGDMVEIH GKHEERQDEHGFIAREFNRK YRIPADVDPLTITSSLSLDG VLTVSAPRKQSDVPERSIPI TREEKPAIAGAQRK | 8 |

In a preferred aspect, the present disclosure provides recombinant polypeptides that comprise, consist essentially of, or consist of, any of the amino acid sequences shown in Table 1B. The present disclosure also provides recombinant polypeptides that have an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1B.

TABLE 1B

Recombinant Polypeptide Sequences

| Name | Amino Acid Sequence | SEQ ID NO: |
|---|---|---|
| CRYA_1B *Anser cygnoides domesticus* CRYAA | MDITIQHPWFKRALGPLIPE RLFDQFFGSGLLSYDLLPLF EETIEPYYRQELFREVLSEG IESVREDRDKFTIMLDVKHF EPSDLEVKIIDDFVSIHGKH ESRQDDHGYIERSFHRRYRL PANVDQEAITCELEGDGMLT FEGPKVPENMDPTHESRPIP VERSSKPTEAPEE | 9 |
| *Rhea americana* CRYAA | MDITIQHPWFKRALGPLIPE RLFDQFFGSGLLSYDLLPLF EETIEPYYRQELFREVLSEG IESVREDRSKFTIMLDVKHF EPSDLEVKIIDDFVSIHGKH | 10 |

TABLE 1B-continued

Recombinant Polypeptide Sequences

| Name | Amino Acid Sequence | SEQ ID NO: |
|---|---|---|
| Anas platyrhynchos CRYAA | ESRQDDHGYIERSFHRRYRL PENVDQEAITCELEEDGMLT FEGPKVQANMDPEHESRPIP VERSSKPTEAPEE RALGPLIPERLFDQFFGSGL LSYDLLPLFEETIEPYYRQE LFREVLSEGIESVREDRDKF TIMLDVKHFEPSDLEVKIID DFVSIHGKHESRQDDHGYIE RSFHRRYRLPANVDQEAITC ELEGDGMLTFEGPKVPENMD PTHESRPIP | 11 |
| Anas platyrhynchos CRYAB | MSITIHNPLIRRPLFDWLAP DRIFSQIFGEHLQEDELLPA DPDLDPFLMRDPIFRMPDWL ETGLDEMRLEKSKFDVNLSV KHFDPEELKVKVLGSMVEIH GKHEERQSEHGFIAREFNRK YRIPASVSPLTITDDLDLSG VLTVDAPRKQDSVPERDIPI TREEKPAIAGAQRK | 12 |
| Homo sapiens CRYAA | MDVTIQHPWFKRTLGPFYPE RLFDQFFGSGLFSYDLLPFL EETIEPYYRQELFRTVLDEG IESVREDRDKFVIFLDVKHF EPSDLTVKVQDDFVSIHGKH NSRQDDHGYIERSFHRRYRL PENVDQEALECELEADGMLT FCGPKIQTGLDATHASRAIP VERSSKPTEAPEE | 13 |
| Drosophila melanogaster H5P23 | MANIPLLLSLAVVLGRMSMD PFYEPYYCQRQRNPYLALDG PMEQQLRQLEKQDGASSGSS GADSKIGKVGFQDCMVDSHF KPSELDDKDQVNSDLDEGNH EEREVVHGFITRHFDRRYAL PPGYEAVKDASTLSSVGDLT IKDPKPPAIEVKGNERIDQI QQDGPAHLNDKENPKEADEQ VNGNVK | 14 |
| Drosophila melanogaster H5P22 | MRLSPMFWRMAEEMARMPRS LLPFHAFFHEPPDWLDASPR NWQHIARWQEQESAPPATDN KVGYKSTSVDKVYLESKDKD SVELDDSDEAKLEQQEAEQG GYLLRHFSGRYDSPVGYEAV KDLLLSLVVGDSTILDPNPP GDQETSKEREDTIEQTGEPA KKLAEEPKVKTALQ | 15 |
| Anser cygnoides domesticus CRYAB | MSITIHNPLIRRPLFDWLAP DRIFSQIFGEHLQEDELLPA DPDLDPFLMRDPIFRMPDWL ETGLDEMRLEKSKFDVNLSV KHFDPEELKVKVLGSMVEIH GKHEERQSEHGFIAREFNRK YRIPASVSPLTITDDLDLSG VLTVDAPRKQDSVPERDIPI TREEKPAIAGAQRK | 16 |

The present disclosure provides an alpha crystallin recombinant polypeptide sequence or amino acid sequence derived from *Anser cygnoides domesticus* alpha-A-crystallin (CRYAA) (GenBank # XP_013036875.1) comprising, consisting essentially of, or consisting of, the amino acid sequence of SEQ ID NO: 1 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 1.

The present disclosure provides an acidic alpha crystallin recombinant polypeptide variant sequence or amino acid sequence derived from *Anser cygnoides domesticus* alpha-A-crystallin (CRYAA) (GenBank # XP_013036875.1) comprising, consisting essentially of, or consisting of, the amino acid sequence of SEQ ID NO: 1, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 1, wherein the alpha crystallin recombinant polypeptide variant is acidic as determined by isoelectric point (pI). In some aspects, the pI of the recombinant polypeptide is lower than the pI of SEQ ID NO: 1. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Anser cygnoides domesticus* alpha-A-crystallin (CRYAA) (GenBank # XP_013036875.1) comprising, consisting essentially of, or consisting of, the amino acid sequence of SEQ ID NO: 9 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 9. For example, SEQ ID NO:9 has at least 80% sequence identity to the polypeptide of SEQ ID NO: 1, SEQ ID NO:9 is acidic as determined by pI, the pI of SEQ ID NO:9 is lower than the pI of SEQ ID NO: 1, and aspartic acid (D), glutamic acid (E) and leucine (L) are each independently present in an amount greater than, or equal to, the amount of any other amino acid residue present within SEQ ID NO:9 (that is, glutamic acid (E) is 23 residues, leucine (L) is 15 residues, and aspartic acid (D) is 14 residues of the 173 amino acid sequence of SEQ ID NO:9, with proline (P) (14 residues) being the next most present amino acid residue within SEQ ID NO:9).

The present disclosure provides an alpha crystallin recombinant polypeptide sequence or amino acid sequence derived from *Rhea Americana* alpha-A-crystallin (CRYAA) (GenBank #P02505.1) comprising, consisting essentially of, or consisting of, the amino acid sequence of SEQ ID NO: 2 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 2.

The present disclosure provides an acidic alpha crystallin recombinant polypeptide variant sequence or amino acid sequence derived from *Rhea Americana* alpha-A-crystallin (CRYAA) (GenBank # P02505.1) comprising, consisting essentially of, or consisting of, the amino acid sequence of SEQ ID NO: 2, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 2, wherein the alpha crystallin recombinant polypeptide variant is acidic as determined by isoelectric point (pI). In some aspects, the pI of the recombinant polypeptide is lower than the pI of SEQ ID NO: 2. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Rhea Americana* alpha-A-crystallin (CRYAA) (GenBank # P02505.1) comprising, consisting essentially of, or consisting of, the amino acid sequence of SEQ ID NO: 10 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 10. For example, SEQ ID NO: 10 has at least 75% sequence identity to the polypeptide of SEQ ID NO:2, SEQ ID NO: 10 is acidic as determined by pI, the pI of SEQ ID NO: 10 is lower than the pI of SEQ ID NO:2, and aspartic acid (D), glutamic acid (E) and leucine (L) are each independently present in an amount greater than, or equal to, the amount of any other amino acid residue present within SED ID NO: 10.

The present disclosure provides an alpha crystallin recombinant polypeptide sequence or amino acid sequence derived from *Anas platyrhynchos* alpha-A-crystallin (CRYAA) (GenBank #012984.1) comprising, consisting essentially of, consisting of, the amino acid sequence of SEQ ID NO: 3 or a recombinant polypeptide comprising, consisting essentially of, consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 3.

The present disclosure provides an acidic alpha crystallin recombinant polypeptide variant sequence or amino acid sequence derived from *Anas platyrhynchos* alpha-A-crystallin (CRYAA) (GenBank #012984.1) comprising, consisting essentially of, or consisting of, the amino acid sequence of SEQ ID NO: 3, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 3, wherein the alpha crystallin recombinant polypeptide variant is acidic as determined by isoelectric point (pI). In some aspects, the pI of the recombinant polypeptide is lower than the pI of SEQ ID NO: 3. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Anas platyrhynchos* alpha-A-crystallin (CRYAA) (GenBank #012984.1) comprising, consisting essentially of, or consisting of, the amino acid sequence of SEQ ID NO: 11 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 11. For example, SEQ ID NO: 11 has at least 80% sequence identity to the polypeptide of SEQ ID NO:3, SEQ ID NO: 11 is acidic as determined by pI, the pI of SEQ ID NO: 11 is lower than the pI of SEQ ID NO:3, and aspartic acid (D), glutamic acid (E) and leucine (L) are each independently present in an amount greater than, or equal to, the amount of any other amino acid residue present within SED ID NO: 11.

The present disclosure provides an alpha crystallin recombinant polypeptide sequence or amino acid sequence derived from *Anas platyrhynchos* alpha-B-crystallin (CRYAB) (GenBank #Q05557.1) comprising, consisting essentially of, consisting of, the amino acid sequence of SEQ ID NO: 4 or a recombinant polypeptide comprising, consisting essentially of, consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 4.

The present disclosure provides an acidic alpha crystallin recombinant polypeptide variant sequence or amino acid sequence derived from *Anas platyrhynchos* alpha-B-crystallin (CRYAB) (GenBank # Q05557.1) comprising, consisting essentially of, or consisting of, the amino acid sequence of SEQ ID NO: 4, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 4, wherein the alpha crystallin recombinant polypeptide variant is acidic as determined by isoelectric point (pI). In some aspects, the pI of the recombinant polypeptide is lower than the pI of SEQ ID NO: 4. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Anas platyrhynchos* alpha-B-crystallin (CRYAB) (GenBank # Q05557.1) comprising, consisting essentially of, or consisting of, the amino acid sequence of SEQ ID NO: 12 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 12. For example, SEQ ID NO:12 has at least 80% sequence identity to the polypeptide of SEQ ID NO:4, SEQ ID NO:12 is acidic as determined by pI, the pI of SEQ ID NO:12 is lower than the pI of SEQ ID NO:4, and aspartic acid (D), glutamic acid (E) and leucine (L) are each independently present in an amount greater than, or equal to, the amount of any other amino acid residue present within SED ID NO: 12.

The present disclosure provides an alpha crystallin recombinant polypeptide sequence or amino acid sequence derived from *Homo sapiens* alpha-A-crystallin (CRYAA) (GenBank #AAH69528.1) comprising, consisting essentially of, or consisting of, the amino acid sequence of SEQ ID NO: 5 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 5.

The present disclosure provides an acidic alpha crystallin recombinant polypeptide variant sequence or amino acid sequence derived from *Homo sapiens* alpha-A-crystallin (CRYAA) (GenBank # AAH69528. 1) comprising, consisting essentially of, or consisting of, the amino acid sequence of SEQ ID NO: 5, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 5, wherein the alpha crystallin recombinant polypeptide variant is acidic as determined by isoelectric point (pI). In some aspects, the pI of the recombinant polypeptide is lower than the pI of SEQ ID NO: 5. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Homo sapiens* alpha-A-crystallin (CRYAA) (GenBank # AAH69528.1) comprising, consisting essentially of, or consisting of, the amino acid sequence of SEQ ID NO: 13 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 13. For example, SEQ ID NO: 13 has at least 80% sequence identity to the polypeptide of SEQ ID NO:5, SEQ ID NO: 13 is acidic as determined by pI, the pI of SEQ ID NO: 13 is lower than the pI of SEQ ID NO:5, and aspartic acid (D), glutamic acid (E) and leucine (L) are each independently present in an amount greater than, or equal to, the amount of any other amino acid residue present within SED ID NO: 13.

The present disclosure provides an HSP23 recombinant polypeptide sequence or amino acid sequence derived from *Drosophila melanogaster* HSP23 (GenBank # AAA28637.1) comprising, consisting essentially of, or consisting of, the amino acid sequence of SEQ ID NO: 6 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 6.

The present disclosure provides an HSP23 recombinant polypeptide variant sequence or amino acid sequence derived from *Drosophila melanogaster* HSP23 (GenBank # AAA28637.1) comprising, consisting essentially of, or consisting of, the amino acid sequence of SEQ ID NO: 6, wherein the HSP23 recombinant polypeptide variant is acidic as determined by isoelectric point (pI), or an acidic HSP23 recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 6, wherein the HSP23 recombinant polypeptide variant is acidic as determined by isoelectric point (pI). In some aspects, the pI of the recombinant polypeptide is lower than the pI of SEQ ID NO: 6. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic HSP23 recombinant polypeptide variant or are greater than or equal to in abundance to the next most abundant amino acid residue of the acidic HSP23 recombinant polypeptide variant.

In a preferred aspect, the recombinant polypeptide is an acidic variant derived from *Drosophila melanogaster* HSP23 (GenBank # AAA28637.1) comprising, consisting essentially of, or consisting of, the amino acid sequence of SEQ ID NO: 14 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 14. For example, SEQ ID NO: 14 has at least 80% sequence identity to the polypeptide of SEQ ID NO:6, SEQ ID NO: 14 is acidic as determined by pI, the pI of SEQ ID NO: 14 is lower than the pI of SEQ ID NO:6, and aspartic acid (D), glutamic acid (E) and leucine (L) are each independently present in an amount greater than, or equal to, the amount of any other amino acid residue present within SED ID NO: 14.

The present disclosure provides an HSP22 recombinant polypeptide sequence or amino acid sequence derived from *Drosophila melanogaster* HSP22 (GenBank # AAA28635.1) comprising, consisting essentially of, or consisting of, the amino acid sequence of SEQ ID NO: 7 or a recombinant polypeptide having an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 7.

The present disclosure provides an acidic HSP22 recombinant polypeptide variant sequence or amino acid sequence derived from *Drosophila melanogaster* HSP22 (GenBank #AAA28635.1) comprising, consisting essentially of, or consisting of, the amino acid sequence of SEQ ID NO: 7, wherein the HSP22 recombinant polypeptide variant is acidic as determined by isoelectric point (pI), or an acidic HSP22 recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 7, wherein the HSP22 recombinant polypeptide variant is acidic as determined by isoelectric point (pI). In some aspects, the pI of the recombinant polypeptide is lower than the pI of SEQ ID NO: 7. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic HSP22 recombinant polypeptide variant or are greater than or equal to in abundance to the next most abundant amino acid residue of the acidic HSP22 recombinant polypeptide variant.

In a preferred aspect, the recombinant polypeptide is an acidic variant derived from *Drosophila melanogaster* HSP22 (GenBank # AAA28635.1) comprising, consisting essentially of, or consisting of, the amino acid sequence of SEQ ID NO: 15 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 15. For example, SEQ ID NO: 15 has at least 65% sequence identity to the polypeptide of SEQ ID NO:7, SEQ ID NO: 15 is acidic as determined by pI, the pI of SEQ ID NO: 15 is lower than the pI of SEQ ID NO:7, and aspartic acid (D), glutamic acid (E) and leucine (L) are each independently present in an amount greater than, or equal to, the amount of any other amino acid residue present within SED ID NO: 15.

The present disclosure provides an alpha crystallin recombinant polypeptide sequence or amino acid sequence derived from *Anser cygnoides domesticus* alpha-B-crystallin (CRYAB) (GenBank # XP_013042703.1) comprising, consisting essentially of, or consisting of, the amino acid sequence of SEQ ID NO: 8 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 8.

The present disclosure provides an acidic alpha crystallin recombinant polypeptide variant sequence or amino acid sequence derived from *Anser cygnoides domesticus* alpha-B-crystallin (CRYAB) (GenBank # XP_013042703.1) comprising, consisting essentially of, or consisting of, the amino acid sequence of SEQ ID NO: 8, wherein the alpha crystallin recombinant polypeptide variant is acidic as determined by isoelectric point (pI), or an acidic alpha crystallin recombinant polypeptide variant comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 8, wherein the alpha crystallin recombinant polypeptide variant is acidic as determined by isoelectric point (pI). In some aspects, the pI of the recombinant polypeptide is lower than the pI of SEQ ID NO: 8. In some aspects, leucine (L), aspartic acid (D) and glutamic acid (E) are each independently present in an amount greater than, or equal to, the amount of any other amino acid residue present within the recombinant polypeptide sequence. In some aspects, leucine (L), aspartic acid (D) and glutamic acid (E) are the three most abundant amino acid residues in the acidic alpha crystallin recombinant polypeptide variant or are greater than or equal to in abundance to the next most abundant amino acid residue of the acidic alpha crystallin recombinant polypeptide variant.

In a preferred aspect, the recombinant polypeptide is an acidic variant derived from *Anser cygnoides domesticus* alpha-B-crystallin (CRYAB) (GenBank # XP_013042703.1) comprising, consisting essentially of, or consisting of, the amino acid sequence of SEQ ID NO: 16 or a recombinant polypeptide comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to the amino acid sequence of SEQ ID NO: 16. For example, SEQ ID NO:16 has at least 80% sequence identity to the polypeptide of SEQ ID NO:8, SEQ ID NO: 16 is acidic as determined by pI, the pI of SEQ ID NO: 16 is lower than the pI of SEQ ID NO:8, and aspartic acid (D), glutamic acid (E) and leucine (L) are each independently present in an amount greater than, or equal to, the amount of any other amino acid residue present within SED ID NO:16.

The present disclosure provides an isolated nucleic acid molecule encoding a recombinant polypeptide that comprises, consists essentially of, or consists of, any of the amino acid sequences shown in Table 1A. The present disclosure also provides isolated nucleic acid molecules encoding recombinant polypeptides comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

The present disclosure also provides an isolated nucleic acid molecule encoding a recombinant polypeptide variant that comprises, consists essentially of, or consists of, any of the amino acid sequences shown in Table 1A, wherein the recombinant polypeptide variant is acidic as determined by isoelectric point (pI). The present disclosure also provides isolated nucleic acid molecules encoding a recombinant polypeptide variants comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

The present disclosure also provides isolated nucleic acid molecules encoding acidic recombinant polypeptide variants that comprise, consist essentially of, or consist of, any of the amino acid sequences shown in Table 1A, wherein the recombinant polypeptide variant is acidic as determined by isoelectric point (pI), wherein the pI of the recombinant peptide variant is lower than the pI of peptide sequence from which the recombinant peptide was derived, and wherein leucine (L), aspartic acid (D) and glutamic acid (E) are each independently present in an amount greater than, or equal to, the amount of any other amino acid residue present within the recombinant polypeptide sequence. The present disclosure also provides isolated nucleic acid molecules encoding acidic recombinant polypeptide variants that comprise, consist essentially of, or consist of, any of the amino acid sequences shown in Table 1A, wherein the recombinant polypeptide variant is acidic as determined by isoelectric point (pI) and wherein leucine (L), aspartic acid (D) and glutamic acid (E) are the three most abundant amino acid sequences of the acidic variant or are greater than or equal to in abundance to the next most abundant amino acid residue of the acidic alpha crystallin recombinant polypeptide variant. The present disclosure also provides isolated nucleic acid molecules encoding acid recombinant polypeptide variants comprising, consisting essentially of, or consisting of, an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences shown in Table 1A.

The present disclosure also provides isolated nucleic acid molecules that comprise, consist essentially of, or consist of, any of the nucleic acid sequences shown in Table 2A. The present disclosure also provides nucleic acid molecules comprising, consisting essentially of, or consisting of, a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequences shown in Table 2A.

TABLE 2A

Nucleic Acid Sequences

| Name | Nucleic Acid Sequence | SEQ ID NO: |
|---|---|---|
| *Anser cygnoides domesticus* CRYAA | ATGGATATTACCATTCAGCA TCCGTGGTTTAAACGCGCGC TGGGCCCGCTGATTCCGAGC CGCCTGTTTGATCAGTTTTT TGGCGAAGGCCTGCTGGAAT ATGATCTGCTGCCGCTGTTT AGCAGCACCATTAGCCCGTA TTATCGCCAGAGCCTGTTTC GCAGCGTGCTGGAAAGCGGC ATTAGCGAAGTGCGCAGCGA TCGCGATAAATTTACCATTA TGCTGGATGTGAAACATTTT AGCCCGGAAGATCTGAGCGT GAAAATTATTGATGATTTTG TGGAAATTCATGGCAAACAT AGCGAACGCCAGGATGATCA TGGCTATATTAGCCGCGAAT TTCATCGCCGCTATCGCCTG CCGGCGAACGTGGATCAGAG CGCGATTACCTGCAGCCTGA GCGGCGATGGCATGCTGACC TTTAGCGGCCCGAAAGTGCC GAGCAACATGGATCCGACCC ATAGCGAACGCCCGATTCCG GTGAGCCGCGAAGAAAAACC GACCAGCGCGCCGAGCAGC | 17 |
| *Rhea americana* CRYAA | ATGGATATTACCATTCAGCA TCCGTGGTTTAAACGCGCGC TGGGCCCGCTGATTCCGAGC CGCCTGTTTGATCAGTTTTT TGGCGAAGGCCTGCTGGAAT ATGATCTGCTGCCGCTGTTT AGCAGCACCATTAGCCCGTA TTATCGCCAGAGCCTGTTTC GCAGCGTGCTGGAAAGCGGC ATTAGCGAAGTGCGCAGCGA TCGCGAAAAATTTACCATTA TGCTGGATGTGAAACATTTT AGCCCGGAAGATCTGAGCGT GAAAATTATTGATGATTTTG TGGAAATTCATGGCAAACAT AGCGAACGCCAGGATGATCA TGGCTATATTAGCCGCGAAT TTCATCGCCGCTATCGCCTG CCGAGCAACGTGGATCAGAG CGCGATTACCTGCAGCCTGA GCAGCGATGGCATGCTGACC TTTAGCGGCCCGAAAGTGCA GGCGAACATGGATCCGAGCC ATAGCGAACGCCCGATTCCG GTGAGCCGCGAAGAAAAACC GACCAGCGCGCCGAGCAGC | 18 |
| *Anas platyrhynchos* CRYAA | CGCGCGCTGGGCCCGCTGAT TCCGAGCCGCCTGTTTGATC AGTTTTTTGGCGAAGGCCTG CTGGAATATGATCTGCTGCC GCTGTTTAGCAGCACCATTA GCCCGTATTATCGCCAGAGC CTGTTTCGCAGCGTGCTGGA AAGCGGCATTAGCGAAGTGC GCAGCGATCGCGATAAATTT ACCATTATGCTGGATGTGAA ACATTTTAGCCCGGAAGATC TGAGCGTGAAAATTATTGAT GATTTTGTGGAAATTCATGG CAAACATAGCGAACGCCAGG ATGATCATGGCTATATTAGC CGCGAATTTCATCGCCGCTA TCGCCTGCCGGCGAACGTGG ATCAGAGCGCGATTACCTGC AGCCTGAGCGGCGATGGCAT GCTGACCTTTAGCGGCCCGA AAGTGCCGAGCAACATGGAT CCGACCCATAGCGAACGCCC GATTCCG | 19 |

TABLE 2A-continued

Nucleic Acid Sequences

| Name | Nucleic Acid Sequence | SEQ ID NO: |
|---|---|---|
| Anas platyrhynchos CRYAB | ATGGATATTACCATTCATAACCCGCTGATTCGCCGCCCGCTGTTTAGCTGGCTGGCGCCGAGCCGCATTTTTGATCAGATTTTTGGCGAACATCTGCAGGAAAGCGAACTGCTGCCGGCGAGCCCGAGCCTGAGCCCGTTTCTGATGCGCAGCCCGATTTTTCGCATGCCGAGCTGGCTGGAAACCGGCCTGAGCGAAATGCGCCTGGAAAAAGATAAATTTAGCGTGAACCTGGATGTGAAACATTTTAGCCCGGAAGAACTGAAAGTGAAAGTGCTGGGCGATATGGTGGAAATTCATGGCAAACATGAAGAACGCCAGGATGAACATGGCTTTATTGCGCGCGAATTTAACCGCAAATATCGCATTCCGGCGGATGTGGATCCGCTGACCATTACCAGCAGCCTGAGCCTGGATGGCGTGCTGACCGTGAGCGCGCCGCGCAAACAGAGCGATGTGCCGGAACGCAGCATTCCGATTACCCGCGAAGAAAAACCGGCGATTGCGGGCGCGCAGCGCAAA | 20 |
| Homo sapiens CRYAA | ATGGATGTGACCATTCAGCATCCGTGGTTTAAACGCACCCTGGGCCCGTTTTATCCGAGCCGCCTGTTTGATCAGTTTTTTGGCGAAGGCCTGTTTGAATATGATCTGCTGCCGTTTCTGAGCAGCACCATTAGCCCGTATTATCGCCAGAGCCTGTTTCGCACCGTGCTGGATAGCGGCATTAGCGAAGTGCGCAGCGATCGCGATAAATTTGTGATTTTCTGGATGTGAAACATTTTAGCCCGGAAGATCTGACCGTGAAAGTGCAGGATGATTTGTGGAAATTCATGGCAAACATAACGAACGCCAGGATGATCATGGCTATATTAGCCGCGAATTTCATCGCCGCTATCGCCTGCCGAGCAACGTGGATCAGAGCGCGCTGAGCTGCAGCCTGAGCGCGGATGGCATGCTGACCTTTTGCGGCCCGAAAATTCAGACCGGCCTGGATGCGACCCATGCGGAACGCGCGATTCCGGTGAGCCGCAAGAAAAACCGACCAGCGCGCCGAGCAGC | 21 |
| Drosophila melanogaster HSP23 | ATGGCGAACATTCCGCTGCTGCTGAGCCTGGCGGATGATCTGGGCCGCATGAGCATGGTGCCGTTTTATGAACCGTATTATTGCCAGCGCCAGCGCAACCCGTATCTGGCGCTGGTGGGCCCGATGGAACAGCAGCTGCGCCAGCTGGAAAAACAGGTGGGCGCGAGCAGCGGCAGCAGCGGCGCGGTGAGCAAAATTGGCAAAGATGGCTTTCAGGTGTGCATGGATGTGAGCCATTTTAAACCGAGCGAACTGGTGGTGAAAGTGCAGGATAACAGCGTGCTGGTGGAAGGCAACCATGAAGAACGCAAGATGATCATGGCTTTATTACCCGCCATTTTGTGCGCCGCTATGCGCTGCCGCCGGGCTATGAAGCGGATAAAGTGGCGAGCACCCTGAGCAGCGATGGCGTGCTGACCATTAAAGTGCCGAAACCGCCGGCGATTGAAGATAAAGGCA | 22 |
| Drosophila melanogaster HSP22 | ACGAACGCATTGTGCAGATTCAGCAGGTGGGCCCGGCGCATCTGAACGTGAAAGAAAACCCGAAAGAAGCGGTGGAACAGGATAACGGCAACGATAAAATGCGCAGCCTGCCGATGTTTTGGCGCATGGCGGAAGAAATGGCGCGCATGCCGCGCCTGAGCAGCCCGTTTCATGCGTTTTTTCATGAACCGCCGGTGTGGAGCGTGGCGCTGCCGCGCAACTGGCAGCATATTGCGCGCTGGCAGGAACAGGAACTGGCGCCGCCGGCGACCGTGAACAAAGATGGCTATAAACTGACCCTGGATGTGAAAGATTATAGCGAACTGAAAGTGAAAGTGCTGGATGAAAGCGTGGTGCTGGTGGAAGCGAAAAGCGAACAGCAGGAAGCGGAACAGGGCGGCTATAGCAGCCGCCATTTTCTGGGCCGCTATGTGCTGCCGGATGGCTATGAAGCGGATAAAGTGAGCAGCAGCCTGAGCGATGATGGCGTGCTGACCATTAGCGTGCCGAACCCGCCGGGCGTGCAGGAAACCCTGAAAGAACGCGAAGTGACCATTGAACAGACCGGCGAACCGGCGAAAAAAAGCGCGGAAGAACCGAAAGATAAAACCGCGAGCCAG | 23 |
| Anser cygnoides domesticus CRYAB | ATGGATATTACCATTCATAACCCGCTGATTCGCCGCCCGCTGTTTAGCTGGCTGGCGCCGAGCCGCATTTTTGATCAGATTTTTGGCGAACATCTGCAGGAAAGCGAACTGCTGCCGGCGAGCCCGAGCCTGAGCCCGTTTCTGATGCGCAGCCCGATTTTTCGCATGCCGAGCTGGCTGGAAACCGGCCTGAGCGAAATGCGCCTGGAAAAAGATAAATTTAGCGTGAACCTGGATGTGAAACATTTTAGCCCGGAAGAACTGAAAGTGAAAGTGCTGGGCGATATGGTGGAAATTCATGGCAAACATGAAGAACGCCAGGATGAACATGGCTTTATTGCGCGCGAATTTAACCGCAAATATCGCATTCCGGCGGATGTGGATCCGCTGACCATTACCAGCAGCCTGAGCCTGGATGGCGTGCTGACCGTGAGCGCGCCGCGCAAACAGAGCGATGTGCCGGAACGCAGCATTCCGATTACCCGCGAAGAAAAACCGGCGATTGCGGGCGCGCAGCGCAA | 24 |

In a preferred aspect, the present disclosure provides isolated nucleic acid molecules that comprise, consist essentially of, or consist of, any of the nucleic acid sequences shown in Table 2B. The present disclosure also provides nucleic acid molecules comprising, consisting essentially of, or consisting of, a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequences shown in Table 2B.

TABLE 2B

Nucleic Acid Sequences

| Name | Nucleic Acid Sequence | SEQ ID NO: |
|---|---|---|
| CRYA_1B Anser cygnoides domesticus CRYAA | ATGGATATTACCATTCAGCA TCCGTGGTTTAAACGCGCGC TGGGCCCGCTGATTCCGGAA CGCCTGTTTGATCAGTTTTT TGGCAGCGGCCTGCTGAGCT ATGATCTGCTGCCGCTGTTT GAAGAAACCATTGAACCGTA TTATCGCCAGGAACTGTTTC GCGAAGTGCTGAGCGAAGGC ATTGAAAGCGTGCGCGAAGA TCGCGATAAATTTACCATTA TGCTGGATGTGAAACATTTT GAACCGAGCGATCTGGAAGT GAAAATTATTGATGATTTTG TGAGCATTCATGGCAAACAT GAAAGCCGCCAGGATGATCA TGGCTATATTGAACGCAGCT TTCATCGCCGCTATCGCCTG CCGGCGAACGTGGATCAGGA AGCGATTACCTGCGAACTGG AAGGCGATGGCATGCTGACC TTTGAAGGCCCGAAAGTGCC GGAAAACATGGATCCGACCC ATGAAAGCCGCCCGATTCCG GTGGAACGCAGCAGCAAACC GACCGAAGCGCCGGAAGAA | 25 |
| Rhea americana CRYAA | ATGGATATTACCATTCAGCA TCCGTGGTTTAAACGCGCGC TGGGCCCGCTGATTCCGGAA CGCCTGTTTGATCAGTTTTT TGGCAGCGGCCTGCTGAGCT ATGATCTGCTGCCGCTGTTT GAAGAAACCATTGAACCGTA TTATCGCCAGGAACTGTTTC GCGAAGTGCTGAGCGAAGGC ATTGAAAGCGTGCGCGAAGA TCGCAGCAAATTTACCATTA TGCTGGATGTGAAACATTTT GAACCGAGCGATCTGGAAGT GAAAATTATTGATGATTTTG TGAGCATTCATGGCAAACAT GAAAGCCGCCAGGATGATCA TGGCTATATTGAACGCAGCT TTCATCGCCGCTATCGCCTG CCGGAAAACGTGGATCAGGA AGCGATTACCTGCGAACTGG AAGAAGATGGCATGCTGACC TTTGAAGGCCCGAAAGTGCA GGCGAACATGGATCCGGAAC ATGAAAGCCGCCCGATTCCG GTGGAACGCAGCAGCAAACC GACCGAAGCGCCGGAAGAA | 26 |
| Anas platyrhynchos CRYAA | CGCGCGCTGGGCCCGCTGAT TCCGGAACGCCTGTTTGATC AGTTTTTTGGCAGCGGCCTG CTGAGCTATGATCTGCTGCC GCTGTTTGAAGAAACCATTG AACCGTATTATCGCCAGGAA CTGTTTCGCGAAGTGCTGAG CGAAGGCATTGAAAGCGTGC GCGAAGATCGCGATAAATTT ACCATTATGCTGGATGTGAA ACATTTTGAACCGAGCGATC TGGAAGTGAAAATTATTGAT GATTTTGTGAGCATTCATGG CAAACATGAAAGCCGCCAGG ATGATCATGGCTATATTGAA CGCAGCTTTCATCGCCGCTA TCGCCTGCCGGCGAACGTGG ATCAGGAAGCGATTACCTGC GAACTGGAAGGCGATGGCAT GCTGACCTTTGAAGGCCCGA AAGTGCCGGAAAACATGGAT CCGACCCATGAAAGCCGCCC GATTCCG | 27 |
| Anas platyrhynchos CRYAB | ATGAGCATTACCATTCATAA CCCGCTGATTCGCCGCCCGC TGTTTGATTGGCTGGCGCCG GATCGCATTTTTAGCCAGAT TTTTGGCGAACATCTGCAGG AAGATGAACTGCTGCCGGCG GATCCGGATCTGGATCCGTT TCTGATGCGCGATCCGATTT TTCGCATGCCGGATTGGCTG GAAACCGGCCTGGATGAAAT GCGCCTGGAAAAAAGCAAAT TTGATGTGAACCTGAGCGTG AAACATTTTGATCCGGAAGA ACTGAAAGTGAAAGTGCTGG GCAGCATGGTGGAAATTCAT GGCAAACATGAAGAACGCCA GAGCGAACATGGCTTTATTG CGCGCGAATTTAACCGCAAA TATCGCATTCCGGCGAGCGT GAGCCCGCTGACCATTACCG ATGATCTGGATCTGAGCGGC GTGCTGACCGTGGATGCGCC GCGCAAACAGGATAGCGTGC CGGAACGCGATATTCCGATT ACCCGCGAAGAAAAACCGGC GATTGCGGGCGCGCAGCGCA AA | 28 |
| Homo sapiens CRYAA | ATGGATGTGACCATTCAGCA TCCGTGGTTTAAACGCGCGC TGGGCCCGTTTTATCCGGAA CGCCTGTTTGATCAGTTTTT TGGCAGCGGCCTGTTTAGCT ATGATCTGCTGCCGTTTCTG GAAGAAACCATTGAACCGTA TTATCGCCAGGAACTGTTTC GCACCGTGCTGGATGAAGGC ATTGAAAGCGTGCGCGAAGA TCGCGATAAATTTGTGATTT TTCTGGATGTGAAACATTTT GAACCGAGCGATCTGACCGT GAAAGTGCAGGATGATTTTG TGAGCATTCATGGCAAACAT AACAGCCGCCAGGATGATCA TGGCTATATTGAACGCAGCT TTCATCGCCGCTATCGCCTG CCGGAAAACGTGGATCAGGA AGCGCTGGAATGCGAACTGG AAGCGGATGGCATGCTGACC TTTTGCGGCCCGAAAATTCA GACCGGCCTGGATGCGACCC ATGCGAGCCGCGCGATTCCG GTGGAACGCAGCAGCAAACC GACCGAAGCGCCGGAAGAA | 29 |
| Drosophila melanogaster HSP23 | ATGGCGAACATTCCGCTGCT GCTGAGCCTGGCGGTGGTGC TGGGCCGCATGAGCATGGAT CCGTTTTATGAACCGTATTA TTGCCAGCGCCAGCGCAACC CGTATCTGGCGCTGGATGGC CCGATGGAACAGCAGCTGCG CCAGCTGGAAAAACAGGATG GCGCGAGCAGCGGCAGCAGC GGCGCGGATAGCAAAATTGG CAAAGTGGGCTTTCAGGATT GCATGGTGGATAGCCATTTT AAACCGAGCGAACTGGATGA TAAAGATCAGGTGAACAGCG ATCTGGATGAAGGCAACCAT GAAGAACGCGAAGTGGTGCA TGGCTTTATTACCCGCCATT TTGATCGCCGCTATGCGCTG CCGCCGGGCTATGAAGCGGT GAAAGATGCGAGCACCCTGA GCAGCGTGGGCGATCTGACC ATTAAAGATCCGAAACCGCC GGCGATTGAAGTGAAAGGCA | 30 |

TABLE 2B-continued

Nucleic Acid Sequences

| Name | Nucleic Acid Sequence | SEQ ID NO: |
|---|---|---|
| Drosophila melanogaster HSP22 | ACGAACGCATTGATCAGATT CAGCAGGATGGCCCGGCGCA TCTGAACGATAAAGAAAACC CGAAAGAAGCGGATGAACAG GTGAACGGCAACGTGAAA ATGCGCCTGAGCCCGATGTT TTGGCGCATGGCGGAAGAAA TGGCGCGCATGCCGCGCAGC CTGCTGCCGTTTCATGCGTT TTTTCATGAACCGCCGGATT GGCTGGATGCGAGCCCGCGC AACTGGCAGCATATTGCGCG CTGGCAGGAACAGGAAAGCG CGCCGCCGGCGACCGATAAC AAAGTGGGCTATAAAAGCAC CAGCGTGGATAAAGTGTATC TGGAAAGCAAAGATAAAGAT AGCGTGGAACTGGATGATAG CGATGAAGCGAAACTGGAAC AGCAGGAAGCGGAACAGGGC GGCTATCTGCTGCGCCATTT TAGCGGCCGCTATGATAGCC CGGTGGGCTATGAAGCGGTG AAAGATCTGCTGCTGAGCCT GGTGGTGGGCGATAGCACCA TTCTGGATCCGAACCCGCCG GGCGATCAGGAAACCAGCAA AGAACGCGAAGATACCATTG AACAGACCGGCGAACCGGCG AAAAAACTGGCGGAAGAACC GAAAGTGAAAACCGCGCTGCAG | 31 |
| Anser cygnoides domesticus CRYAB | ATGAGCATTACCATTCATAA CCCGCTGATTCGCCGCCCGC TGTTTGATTGGCTGGCGCCG GATCGCATTTTTAGCCAGAT TTTTGGCGAACATCTGCAGG AAGATGAACTGCTGCCGGCG GATCCGGATCTGGATCCGTT TCTGATGCGCGATCCGATTT TTCGCATGCCGGATTGGCTG GAAACCGGCCTGGATGAAAT GCGCCTGGAAAAAAGCAAAT TTGATGTGAACCTGAGCGTG AAACATTTTGATCCGGAAGA ACTGAAAGTGAAAGTGCTGG GCAGCATGGTGGAAATTCAT GGCAAACATGAAGAACGCCA GAGCGAACATGGCTTTATTG CGCGCGAATTTAACCGCAAA TATCGCATTCCGGCGAGCGT GAGCCCGCTGACCATTACCG ATGATCTGGATCTGAGCGGC GTGCTGACCGTGGATGCGCC GCGCAAACAGGATAGCGTGC CGGAACGCGATATTCCGATT ACCCGCGAAGAAAACCGGC GATTGCGGGCGCGCAGCGCAAA | 32 |

The present disclosure also provides pharmaceutical compositions comprising the recombinant polypeptides or nucleic acids disclosed herein.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

In one aspect, the pharmaceutical composition can comprise, consist essentially of, or consist of any one of the recombinant polypeptides disclosed herein in a pharmaceutically acceptable carrier. In some aspects, the pharmaceutical composition is formulated as an aqueous formulation. The aqueous formulation can comprise, consist essentially of, or consist of a salt buffer that may be selected from, but is not limited to, NaCl, KCl, and NaOAc. In one aspect, the salt buffer comprises NaCl. In one aspect, the NaCl is at a concentration from about 0.4M to about 1.0M. In one aspect, the pH of the buffer solution is between about 7.5 and about 9.0. In one aspect, the pH of the buffer solution is about 7.4.

A compound or pharmaceutical composition of the invention can be administered to a subject in many of the well-known methods currently used for chemotherapeutic treatment. For example, for the treatment of cancer, a compound of the invention may be injected directly into tumors, injected into the blood stream or body cavities, taken orally or applied through the skin with patches.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In one aspect, the disease or condition to be treated is a cell proliferative disorder. In a preferred aspect, the disease or condition to be treated is cancer.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze drying that yields a powder of the active ingredient plus any additional desired ingredient from a previously sterile filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The pharmaceutical compositions can include co-formulations of any of the recombinant polypeptides and nucleic acids described herein.

The pharmaceutical compositions can be included in a container, pack, or dispenser together with instructions for administration.

The present disclosure also provides plasmids, expression vectors and host cells comprising the recombinant polypeptides disclosed herein and the nucleic acid molecules encoding the recombinant polypeptides disclosed herein. In one aspect, the disclosure provides a plasmid or an expression vector comprising a nucleic acid molecule, the molecule comprising a nucleotide sequence of any one of SEQ ID NO: 17-32, or a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequence of SEQ ID NO: 17-32, or a fragment thereof. In one aspect, the disclosure provides a host cell comprising a recombinant polypeptide comprising an amino acid sequence of any one of SEQ ID NO: 1-16, or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-16, or a fragment thereof, or a host cell comprising a nucleic acid molecule comprising a nucleic acid sequence of any one of SEQ ID NO: 17-32, or a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the nucleic acid sequence of SEQ ID NO: 17-32, or a fragment thereof.

As used herein, the term "transformation," "transfection," and "transduction" refer to the transfer of nucleic acid (i.e., a nucleotide polymer) into a cell. As used herein, the term "genetic transformation" refers to the transfer and incorporation of DNA, especially recombinant DNA, into a cell. The transferred nucleic acid can be introduced into a cell via an expression vector.

Polynucleotide molecules comprising a desired polynucleotide sequence are propagated by placing the molecule in a vector. Viral and non-viral vectors can be used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the disclosure is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which can be inducible or constitutive, where the coding region is operably linked under the transcriptional control of the transcriptional initiation region, and a transcriptional and translational termination region.

An expression cassette ("expression unit") can be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors can provide for extrachromosomal maintenance, particularly as plasmids or viruses, or for integration into the host chromosome. Where extrachromosomal maintenance is desired, an origin sequence is provided for the replication of the plasmid, which can be low or high copy-number. A wide variety of markers are available for selection, particularly those which protect against toxins, more particularly against antibiotics. The particular marker that is chosen is selected in accordance with the nature of the host, where, in some cases, complementation can be employed with auxotrophic hosts. Introduction of the DNA construct can use any convenient method, including, e.g., conjugation, bacterial transformation, calcium-precipitated DNA, electroporation, fusion, transfection, infection with viral vectors, biolistics, and the like.

Accordingly, polypeptides for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, N.Y., 2001), and Ausubel et al., *Short Protocols in Molecular Biology* (4th ed., John Wiley & Sons, 1999). For example, the recombinant polypeptides of the disclosure can be expressed from bacterial *Escherichia coli* cells.

To direct a recombinant polypeptide into the secretory pathway of a host cell, a secretory signal sequence (also known as a leader sequence) can be provided in the expression vector. The secretory signal sequence can be that of the native form of the recombinant protein, or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., Welch et al., U.S. Pat. No. 5,037,743; Holland et al., U.S. Pat. No. 5,143,830).

Cultured mammalian cells can be suitable hosts for production of recombinant polypeptides for use within the present disclosure. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, Utah); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like;

the gpt gene for xanthine-guanine phosphoribosyl transferase, which permits host cell growth in the presence of mycophenolic acid/xanthine; and markers that provide resistance to zeocin, bleomycin, blastocidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York 1994); and *Baculovirus Expression Protocols. Methods in Molecular Biology* (Richardson ed., Humana Press, Totowa, N.J., 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, a recombinant virus can be used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See generally Glick and Pasternak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2-5 \times 10^5$ cells to a density of $1-2 \times 10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present disclosure. Yeast species of in this regard include, e.g., *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., J. Gen. Microbiol. 132:3459-3465, 1986; Cregg, U.S. Pat. No. 4,882,279; and Raymond et al., Yeast 14:11-23, 1998. *Aspergillus* cells can be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus*, and other genera are also useful host cells within the present disclosure. Techniques for transforming these hosts and expressing foreign DNA sequences cloned therein are well-known in the art (see, e.g., Sambrook and Russell, supra). When expressing a recombinant protein in bacteria such as *E. coli*, the protein can be retained in the cytoplasm, typically as insoluble granules, or can be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein can be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The recombinant polypeptides can be purified by conventional protein purification methods, typically by a combination of chromatographic techniques. See generally *Affinity Chromatography: Principles & Methods* (Pharmacia LKB Biotechnology, Uppsala, Sweden, 1988); Scopes, *Protein Purification: Principles and Practice* (Springer-Verlag, New York 1994). Additional purification steps, such as gel filtration, can be used to obtain the desired level of purity or to provide for desalting, buffer exchange, and the like.

The present disclosure provides methods of preventing, delaying the progression of, treating or alleviating a symptom of, or otherwise ameliorating cancer in a subject by administering a recombinant polypeptide and an agent that reduces IL-10.

The subject in need thereof can be a subject with a cell proliferation disorder. Cancers that can be treated according to the methods of the disclosure include a primary, progressive, metastatic or recurrent tumor. Preferably, the tumor is a solid tumor. Cancers include for example, tumors of the central nervous system, a glioma tumor, renal cancer tumor, an ovarian cancer tumor, a head and neck cancer tumor, a liver cancer tumor, a pancreatic cancer tumor, a gastric cancer tumor, an esophageal cancer tumor, a bladder cancer tumor, a ureter cancer tumor, a renal pelvis cancer tumor, a urothelial cell cancer tumor, a urogenital cancer tumor, a cervical cancer tumor, a endometrial cancer tumor, a penile cancer tumor, a thyroid cancer tumor, or a prostate cancer tumor, a breast cancer tumor, a melanoma tumor, a glioma tumor, a colon cancer tumor, a lung cancer tumor, a sarcoma cancer tumor, or a squamous cell tumor, or a prostate cancer tumor. In one aspect the subject has lung cancer, colon cancer or breast cancer.

In one aspect, the methods for enhancing or inducing an immune response in a subject in need thereof comprise administering at least one recombinant polypeptide of the present disclosure, or a nucleic acid encoding a recombinant polypeptide of the present disclosure. In one aspect, the at least one recombinant polypeptide of the present disclosure comprises a recombinant polypeptide of SEQ ID NO: 1-8 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-8 or an acidic variant thereof as described herein. In one aspect, the at least one recombinant polypeptide of the present disclosure comprises a recombinant polypeptide of SEQ ID NO: 9-16 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 9-16. In a preferred aspect, the at least one recombinant polypeptide of the present disclosure comprises a recombinant polypeptide of SEQ ID NO: 9.

In one aspect, enhancing or inducing an "immune response" can be, for example, a cytokine release response or a humoral (antigen-specific) immune response. The immune response to be enhanced for example, can be an innate immune response, a local immune response, a mucosal immune response or a systemic immune response. As used herein, the terms "enhance" or "enhancing" refer to strengthening (augmenting) of an existing immune response. The term "inducing" refers to the initiation of an immune response.

In one aspect, "immune response" refers to "immunogenic cell death" or "immunogenic apoptosis", which is characterized by a robust immune response against antigens expressed by dying cells (FIG. 1). Dying cells, such as cancer cells, can have an increased expression of pre-apoptotic Damage-Associated-Molecular-Pattern (DAMP) signals comprising calreticulin (CRT), HSP70, HSP90, or a combination thereof. In a preferred aspect, the cells have increased expression of each of CRT, HSP70 and HSP90. Techniques known to one skilled in the art can be used to assess the expression of these cell surface markers. For example, the expression of the cell surface markers can be assessed using standard techniques such as flow cytometry, immunocytochemistry (e.g., staining with tissue specific or cell-marker specific antibodies), fluorescence activated cell sorting (FACS), magnetic activated cell sorting (MACS) or other similar methods known in the art. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one aspect, cell surface marker-specific antibodies or ligands are labeled with distinct fluorescent labels. Cells are processed through the flow cytometer, allowing separation of cells based on their ability to bind to the antibodies used. In one aspect, the method of the present disclosure induces the expression of pre-apoptotic HSP70, HSP90 or calreticulin on a cell surface, such as a cancer cell surface.

In one aspect, "immunogenic cell death" or "immunogenic apoptosis" involves the interaction of dendritic cells with a cell, such as a cancer cell, leading to a more rapid rate of endogenous dendritic cell activation, dendritic cell maturation and phagocytosis. The recognition of pre-apoptotic DAMP signals comprising calreticulin (CRT), HSP70, HSP90, or a combination thereof, by the dendritic cells triggers "endogenous dendritic cell activation". This leads to "dendritic cell maturation", which comprises a redistribution of major histocompatibility complex (MHC) molecules from intracellular endocytic compartments to the dendritic cell surface, down-regulation of antigen internalization, an increase of surface expression of co-stimulatory molecules (including CD80 and CD86), cytoskeleton re-organization, secretion of chemokines, cytokines and proteases, surface expression of adhesion molecules and surface expression of chemokine receptors. Mature dendritic cells that have been exposed to cancer cells dying by immunogenic cell death can migrate to lymph nodes and induce high numbers of tumor-specific T lymphocytes (including CD4+ and CD8+ T cells). This triggers a targeted T-cell mediated response towards the cancer cell. The process of "immunogenic cell death" or "immunogenic apoptosis" is shown in FIG. 1. A person skilled in the art will appreciate that not all techniques known to induce cell death will necessarily induce immunogenic cell death. Only agents inducing immunogenic cell death will elicit efficient endogenous dendritic cell activation. In one aspect an "immune response" refers to endogenous dendritic cell activation, dendritic cell maturation or T-cell mediated response or a combination thereof.

In one aspect, "apoptosis" is the term used to describe the cell signaling cascade known as programmed cell death. Various therapeutic indications exist for molecules that induce apoptosis (e.g. cancer). Apoptosis can be monitored by any of a number of available techniques known and available in the art including, for example, assays that measure fragmentation of DNA, alterations in membrane asymmetry, activation of apoptotic caspases and/or release of cytochrome C and AIF. In one aspect, apoptosis is measured by the activation and expression of Caspase 3/7.

The present disclosure also provides methods for treating, preventing or alleviating at least one symptom of a cell proliferative disorder in a subject in need thereof. In one aspect, the method is alleviating at least one symptom of a cell proliferative disorder in a subject in need thereof. In one aspect the cell proliferative disorder is cancer. In a preferred aspect, the cancer is lung cancer, colon cancer or breast cancer.

In one aspect, the methods for treating, preventing or alleviating at least one symptom of a cell proliferative disorder in a subject in need thereof comprise administering at least one recombinant polypeptide of the present disclosure, or a nucleic acid encoding a recombinant polypeptide of the present disclosure. In one aspect, the at least one recombinant polypeptide of the present disclosure comprises a recombinant polypeptide of SEQ ID NO: 1-8 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 1-8 or an acidic variant thereof as described herein. In one aspect, the at least one recombinant polypeptide of the present disclosure comprises a recombinant polypeptide of SEQ ID NO: 9-16. In a preferred aspect, the at least one recombinant polypeptide of the present disclosure comprises a recombinant polypeptide of SEQ ID NO: 9 or an amino acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98% or about 99% identical to any of the amino acid sequences of SEQ ID NO: 9-16.

As used herein, a "subject" can be any mammal, e.g., a human, a primate, mouse, rat, dog, cat, cow, horse, pig, sheep, goat, camel. In a preferred aspect, the subject is a human. In one aspect, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, "treating" describes the management and care of a patient for the purpose of combating a disease, condition, or disorder and includes decreasing or alleviating the symptoms or complications, or eliminating the disease, condition or disorder. As used herein, "preventing" describes stopping the onset of the symptoms or complications of the disease, condition or disorder. As used herein, "alleviating" describes reducing the symptoms or complications of disease, condition or disorder.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the disclosure encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi's sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "lung cancer" is a cell proliferative disorder involving cells of the lung. In one aspect, lung cancer include all forms of cell proliferative disorders affecting lung cells. In one aspect, lung cancer include lung cancer, a precancer or precancerous condition of the lung, benign growths or lesions of the lung, and malignant growths or lesions of the lung, and metastatic lesions in tissue and organs in the body other than the lung. In a preferred aspect, the method of the present disclosure may be used to treat lung cancer or cell proliferative disorders of the lung. In one aspect, lung cancer includes all forms of cancer of the lung. In another aspect, lung cancer includes malignant lung neoplasms, carcinoma in situ, typical carcinoid tumors, and atypical carcinoid tumors. In another aspect, lung cancer includes small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. In another aspect, lung cancer includes "scar carcinoma," bronchioalveolar carcinoma, giant cell carcinoma, spindle cell carcinoma, and large cell neuroendocrine carcinoma. In one aspect lung cancer includes stage 0, IA, IB, IIA, IIB, IIIA, IIIB and IV lung cancer. In another aspect, lung cancer includes lung neoplasms having histologic and ultrastructual heterogeneity (e.g., mixed cell types).

In one aspect, lung cancer include all forms of cell proliferative disorders affecting lung cells. In one aspect, cell proliferative disorders of the lung include lung cancer, precancerous conditions of the lung. In one aspect, cell proliferative disorders of the lung include hyperplasia, metaplasia, and dysplasia of the lung. In another aspect, lung cancer include asbestos-induced hyperplasia, squamous metaplasia, and benign reactive mesothelial metaplasia. In another aspect, cell proliferative disorders of the lung include replacement of columnar epithelium with stratified squamous epithelium, and mucosal dysplasia. In another aspect, individuals exposed to inhaled injurious environmental agents such as cigarette smoke and asbestos may be at increased risk for developing cell proliferative disorders of the lung. In another aspect, prior lung diseases that may predispose individuals to development of cell proliferative disorders of the lung include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "colon cancer" is a cell proliferative disorder involving cells of the colon. In a preferred aspect, the method of the present disclosure may be used to treat colon cancer or cell proliferative disorders of the colon. In one aspect, colon cancer includes all forms of cancer of the colon. In another aspect, colon cancer includes sporadic and hereditary colon cancers. In another aspect, colon cancer includes malignant colon neoplasms, carcinoma in situ, typical carcinoid tumors, and atypical carcinoid tumors. In another aspect, colon cancer includes adenocarcinoma, squamous cell carcinoma, and adenosquamous cell carcinoma. In another aspect, colon cancer is associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. In another aspect, colon cancer is caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

In one aspect, colon cancer include all forms of cell proliferative disorders affecting colon cells. In one aspect, colon cancer include colon cancer, precancerous conditions of the colon, adenomatous polyps of the colon and metachronous lesions of the colon. In one aspect colon cancer includes stage 0, I, IIA, IIB, IIC, IIIA, IIIB, IIIC, IVA, IVB and IVC colon cancer. In one aspect, a colon cancer includes adenoma. In one aspect, colon cancer is characterized by hyperplasia, metaplasia or dysplasia of the colon. In another aspect, prior colon diseases that may predispose individuals to development of cell proliferative disorders of the colon include prior colon cancer. In another aspect, current disease that may predispose individuals to development of cell proliferative disorders of the colon include Crohn's disease and ulcerative colitis. In one aspect, a cell proliferative disorder of the colon is associated with a mutation in a gene selected from the group consisting of p53, ras, FAP and DCC. In another aspect, an individual has an elevated risk of developing a cell proliferative disorder of the colon due to the presence of a mutation in a gene selected from the group consisting of p53, ras, FAP and DCC.

A "breast cancer" is a cell proliferative disorder involving cells of the breast. In a preferred aspect, breast cancer include all forms of cell proliferative disorders affecting breast cells. In one aspect, breast cancer include breast cancer, a precancer or precancerous condition of the breast, benign growths or lesions of the breast, and malignant growths or lesions of the breast, and metastatic lesions in tissue and organs in the body other than the breast. In another aspect, breast cancer include hyperplasia, metaplasia, and dysplasia of the breast.

In one aspect, breast cancer is a precancerous condition of the breast. In one aspect, the method of the present disclosure may be used to treat a precancerous condition of the breast. In one aspect, a precancerous condition of the breast includes atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). In another aspect, a precancerous condition of the breast has been staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

In one aspect, the method of the present disclosure may be used to treat breast cancer. In one aspect, breast cancer includes all forms of cancer of the breast. In one aspect, breast cancer includes primary epithelial breast cancers. In another aspect, breast cancer includes cancers in which the breast is involved by other tumors such as lymphoma, sarcoma or melanoma. In another aspect, breast cancer includes carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. In one aspect, breast cancer includes Stage I, II, IIIA, IIIB, IIIC and IV breast cancer. In one aspect, ductal carcinoma of the breast includes invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. In one aspect, lobular carcinoma of the breast includes invasive lobular carcinoma with predominant in situ component, invasive lobular carcinoma, and infiltrating lobular carcinoma. In one aspect, breast cancer includes Paget's disease, Paget's disease with intraductal carcinoma, and Paget's disease with invasive ductal carcinoma. In another aspect, breast cancer includes breast neoplasms having histologic and ultrastructual heterogeneity (e.g., mixed cell types).

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving a therapy that is not a recombinant polypeptide of the present disclosure. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results in a decrease in the mortality rate of a population of treated subjects in comparison to a population receiving monotherapy with a drug that is not a recombinant polypeptide of the present disclosure. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating, preventing, or alleviating a cancer results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating, preventing, or alleviating a cancer results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating, preventing, or alleviating a cancer results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating, preventing, or alleviating a cancer results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

In one aspect, treating cancer or a cell proliferative disorder results in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. In one aspect, number of cells in a population is measured by fluorescence activated cell sorting (FACS). In another aspect, number of cells in a population is measured by immunofluorescence microscopy. In another aspect, number of cells in a population is measured by light microscopy. In another aspect, methods of measuring cell death are as shown in Li et al., (2003) Proc Natl Acad Sci USA. 100(5): 2674-8. In a preferred aspect, cell death occurs by immunogenic cell death.

The term "subject," or "individual" or "patient" as used herein in reference to individuals having a disease or disorder or are suspected of having a disease or disorder, and the like. Subject, individual or patent may be used interchangeably in the disclosure and encompass mammals and non-mammals. The subject is a pediatric patient or an adult patient.

Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some aspects of the methods and compositions provided herein, the mammal is a human.

The therapeutic methods of the disclosure involve in vivo administration of recombinant polypeptide to a subject. The recombinant polypeptide may be administered to the subject administered by any suitable method, either systemically (e.g., orally, intravenously) or locally (e.g., intraperitoneally, intrathecally, intraventricularly, direct injection into the tissue or organ where the disease or disorder is occurring). Preferably, the recombinant polypeptide is administered intravenously.

The recombinant polypeptide is administered in a single dose or multiple doses, e.g. 2, 3, 4, 5, 6, 7, 8 or more dose administrations.

An effective amount of the first dose of recombinant polypeptide is about 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 20.1, 20.2, 20.3, 20.4, 20.5, 20.6, 20.7, 20.8, 20.9, 21, 21.1, 21.2, 21.3, 21.4, 21.5, 21.6, 21.7, 21.8, 21.9 or 22 mg/kg. Preferably the first dose of the recombinant polypeptide is about 20 mg/kg. An effective amount of a second dose of the recombinant polypeptide is about 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9 or 16 mg/kg. Preferably, the effective amount of the second dose of recombinant polypeptide is about 13.5 mg/kg.

An effective amount of the third dose of recombinant polypeptide is determined by a) determining the constants a and b in the following system of equations:

$$CRP_1 = a \times Amount_1 + b$$

$$CRP_2 - \frac{CRP_1}{8} = a \times Amount_2 + b$$

wherein $CRP_1$ is the amount of CRP in blood from the subject about 20 hours after the administration of the first amount of the recombinant polypeptide, $CRP_2$ is the amount of CRP in blood from the subject about 20 hours after the administration of the second amount of the recombinant polypeptide, $Amount_1$ is the first amount of the recombinant polypeptide and $Amount_2$ is the second amount of the recombinant polypeptide; and b) determining the third amount of the recombinant polypeptide, $Amount_3$, wherein $$Amount_3 = \frac{CRP^{Optimal1} - b}{a},$$

wherein $CRP^{OPtimal1}$ is the intended optimal amount of CRP present in the blood of the subject after administration of the third amount of the recombinant polypeptide;

wherein the $CRP_1$ and $CRP_2$ is measured in mg/L.

An effective amount of the fourth dose of recombinant polypeptide is determined by a) determining the constants a and b in the following system of equations:

$$CRP_1 = a \times Amount_1 + b$$

$$CRP_2 - \frac{CRP_1}{8} = a \times Amount_2 + b$$

wherein $CRP_1$ is the amount of CRP in blood from the subject about 20 hours after the administration of the first amount of the recombinant polypeptide, $CRP_2$ is the amount of CRP in blood from the subject about 20 hours after the administration of the second amount of the recombinant polypeptide, $Amount_1$ is the first amount of the recombinant polypeptide and $Amount_2$ is the second amount of the recombinant polypeptide;

b) determining the fourth amount, Amount$_4$, wherein $$\text{Amount}_4 = \frac{(CRP^{Optimal2} - CRP^{Optimal1}/8) - b}{a};$$

wherein CRP$_1$ and CRP$_2$ is measured in mg/L.

The CRP$^{Optimal1}$ is between about 170 mg/L to about 220 mg/L. Preferably the CRP$^{Optimal1}$ is about 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220 mg/L.

The CRP$^{Optimal2}$ is between about 130 mg/mL to about 180 mg/L. Preferably, the CRP$^{Optimal2}$ is about 150, 151, 152, 153, 154, 155, 156, 157, 158, 159, 160, 161, 162, 163, 164, 165, 166, 167, 168, 169, 170, 171, 172, 173, 174, 175, 176, 177, 178, 179 or 180 mg/L.

An effective amount of the fifth and seventh dose is equivalent to the third dose of recombinant polypeptide. An effective amount of the sixth and eight dose is equivalent to the fourth dose of the recombinant polypeptide.

The therapeutic methods of the disclosure involve in vivo administration of an agent that reduces IL-10 in a subject. The agent may be administered to the subject by any suitable method, either systemically (e.g., orally, intravenously) or locally (e.g., intraperitoneally, intrathecally, intraventricularly, direct injection into the tissue or organ where the disease or disorder is occurring). Preferably, the recombinant polypeptide is administered intravenously or intraperitoneally.

The agent that reduces IL-10 may be an interferon gamma (IFNg), an IFNg mimetic, an IFNg agonist or a combination thereof. Preferably, the agent that reduces IL-10 is interferon gamma (IFNg).

The agent is administered at a dose of about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775 or 800 or more µg/m$^2$.

The agent is administered once every day, once every two days, once every three days, once every four days, once every five days, once every six days or once every seven days. Preferably, it is administered once every four days.

In one aspect, the amount of agent is selected based on the ratio IgG$_{subject}$:IgG$_{healthy}$, wherein IgG$_{subject}$ is the amount of IgG in serum from the subject after the administration of the fifth amount of recombinant polypeptide and IgG$_{healthy}$ is the amount of IgG in serum from a healthy subject.

In one aspect, the amount of agent is selected based on the ratio: L-10$_{subject}$:IL-10$_{healthy}$, wherein IL-10$_{subject}$ is the amount of IL-10 in serum from the subject after administration of the fifth amount of recombinant polypeptide and IL-10$_{healthy}$ is the amount of IL-10 in serum from a healthy subject.

For example, the agent is administered at a dose of about 25 µg/m$^2$ when the ratio is about 1.00, 1.01, 1.02, 1.03, 1.04, 1.05, 1.06, 1.07, 1.08, 1.09, 1.10, 1.11, 1.12, 1.13, 1.14, or 1.15. Preferably, the agent is administered at a dose of about 25 µg/m$^2$ when the ratio is about 1.11.

For example, the agent is administered at a dose of about 50 µg/m$^2$ when the ratio is about 1.20, 1.21, 1.22, 1.23, 1.24, 1.25, 1.26, 1.27, 1.28, 1.29 or 1.30. Preferably, the agent is administered at a dose of about 50 µg/m$^2$ when the ratio is about 1.25.

For example, the agent is administered at a dose of about 75 µg/m$^2$ when the ratio is about 1.28, 1.29, 1.30, 1.31, 1.32, 1.33, 1.34, 1.35, 1.36, 1.37 or 1.38. Preferably, the agent is administered at a dose of about 75 µg/m$^2$ when the ratio is about 1.33.

For example, the agent is administered at a dose of about 100 µg/m$^2$ when the ratio is about 1.38, 1.39, 1.40, 1.41, 1.42, 1.43, 1.44, 1.45, 1.46, 1.47 or 1.48. Preferably, the agent is administered at a dose of about 100 µg/m$^2$ when the ratio is about 1.43.

For example, the agent is administered at a dose of about 150 µg/m$^2$ when the ratio is about 1.77, 1.78, 1.79, 1.80, 1.81, 1.82, 1.83, 1.84, 1.85, 1.86 or 1.87. Preferably, the agent is administered at a dose of about 150 µg/m$^2$ when the ratio is about 1.82.

For example, the agent is administered at a dose of about 300 µg/m$^2$ when the ratio is about 2.81, 2.82, 2.83, 2.84, 2.85, 2.86, 2.87, 2.88, 2.89 or 2.90. Preferably, the agent is administered at a dose of about 300 µg/m$^2$ when the ratio is about 2.86.

For example, the agent is administered at a dose of about 600 µg/m$^2$ when the ratio is about 7.10, 7.11, 7.12, 7.13, 7.14, 7.15, 7.16, 7.17, 7.18, 7.19 or 7.20. Preferably, the agent is administered at a dose of about 600 µg/m$^2$ when the ratio is about 7.14.

Cytokine Storm and Cytokine Release Syndrome

In one embodiment, a method of treating a cancer subject as disclosed herein includes administering an inrmmunotherapy agent. In one embodiment, an immunotherapy agent are immune cells, such as NK cells or T-cells comprising engineered chimeric antigen receptors (CARs) or T-cell receptors (TCRs). In one embodiment, the immunotherapy agent is a recombinant polypeptide or a nucleic acid encoding a recombinant polypeptide. In one embodiment, the immunotherapy agent is an antibody, a checkpoint inhibitor, an interferon, an interleukin, an oncolytic virus, a cancer vaccine or a combination thereof. In one embodiment, the administration of the immunotherapy agent does not cause toxic cytokine release or "cytokine release syndrome" (CRS) or "severe cytokine release syndrome" (sCRS) or "cytokine storm" drat may occur in the subject. In one embodiment, the administration of the immunotherapy agent causes toxic cytokine release or "cytokine release syndrome" (CRS) or "severe cytokine release syndrome" (sCRS) or "cytokine storm" that may occur in the subject. In one embodiment, the CRS, sCRS or cytokine storm occurs as a result of administration of a immunotherapy agent. In one embodiment, a "cytokine cascade", or "hypercytokinemia" is a more severe form of cytokine release syndrome. In one embodiment "hypercytokinemia" is a sustained 3-day cytokine storm.

In one embodiment severe cytokine release syndrome (sCRS) is characterized by elevated levels of several inflammatory cytokines, multiple organ dysfunction and fever. In one embodiment the cytokine measured in the cytokine release syndrome is IL-6. In one embodiment, the fever is transient. In one embodiment, the fever is sustained for a duration of at least one or more days. In one embodiment the fever is sustained for a duration of three days. In one embodiment the fever is at least about 38° C. In one embodiment the temperature of the fever is at least about 38° C., 39° C., 40° C., 41° C. or 42° C. In one embodiment the C-Reactive Protein (CRP) level in the blood from the subject with sCRS is at least about 170, 171, 172, 173, 174, 175, 176, 177, 178, 179, 180, 181, 182, 183, 184, 185, 186, 187, 188, 189 or 190 mg/L. In a preferred embodiment the CRP level is at least about 180 mg/mL. In one embodiment, a single-day event may not result in sCRS. In one embodiment, a two-day cytokine storm develops into sCRS on the third day.

In one embodiment, hypercytokinemia is characterized by elevated levels of several inflammatory cytokines and fever. In one embodiment the cytokine measured in the cytokine release syndrome is IL-6. In one embodiment, the fever is transient. In one embodiment, the fever occurs for a duration of at least one or more days. In one embodiment the fever is at least about 40° C. In one embodiment the temperature of the fever is at least about 38° C., 39° C., 40° C., 41° C. or 42° C. In one embodiment the C-Reactive Protein (CRP)

level in the blood from a subject with hypercytokinemia is at least about 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229 or 230 mg/L. In a preferred embodiment the CRP level is about 200 to about 220 mg/mL.

In one embodiment, a life threatening multiple organ dysfunction and adverse event is characterized by a severe cytokine storm. In one embodiment the cytokine measured in the cytokine release syndrome is IL-6. In one embodiment the fever is at least about 40° C. In one embodiment the temperature of the fever is at least about 38° C., 39° C., 40° C., 41° C. or 42° C. In one embodiment, the fever is sustained for a duration of at least one or more days. In one embodiment the fever is sustained for a duration of three days. In one embodiment the C-Reactive Protein (CRP) level in the blood from a subject with a life threatening adverse event characterized by a severe cytokine storm is at least about 220 mg/mL. In one embodiment the C-Reactive Protein (CRP) level in the blood from a subject with a life threatening multiple organ dysfunction characterized by a severe cytokine storm is at least about 220 mg/mL.

In one embodiment, the method of treating a cancer subject may include an additional agent for decreasing cytokine release. In one embodiment, the additional agent for decreasing harmful cytokine release is a corticosteroid. In one embodiment, the additional agent for decreasing harmful cytokine release comprises apoptotic cells or a composition comprising said apoptotic cells. In another embodiment, the additional agent for decreasing harmful cytokine release comprises a CTLA-4 blocking agent. In another embodiment, the additional agent for decreasing harmful cytokine release comprises immunotherapy agent, and a CTLA-4 blocking agent. In another embodiment, the additional agent for decreasing harmful cytokine release comprises an alpha-1 antitrypsin or fragment thereof or analogue thereof. In another embodiment, the additional agent for decreasing harmful cytokine release comprises immunotherapy agent, and an alpha-1 anti-trypsin or fragment thereof or analogue thereof. In another embodiment, the additional agent for decreasing harmful cytokine release comprises a tellurium-based compound. In another embodiment, the additional agent for decreasing harmful cytokine release comprises immunotherapy agent, and a tellurium-based compound. In another embodiment, the additional agent for decreasing harmful cytokine release comprises an immune modulating agent. In another embodiment, the additional agent for decreasing harmful cytokine release comprises immunotherapy agent, and an immune modulating agent.

A skilled artisan would appreciate that decreasing toxic cytokine release or toxic cytokine levels comprises decreasing or inhibiting production of toxic cytokine levels in a subject, or inhibiting or reducing the incidence of cytokine release syndrome or a cytokine storm in a subject. In another embodiment, toxic cytokine levels are reduced during CRS or a cytokine storm. In another embodiment, decreasing or inhibiting the production of toxic cytokine levels comprises treating CRS or a cytokine storm. In another embodiment, decreasing or inhibiting the production of toxic cytokine levels comprises preventing CRS or a cytokine storm. In another embodiment, decreasing or inhibiting the production of toxic cytokine levels comprises alleviating CRS or a cytokine storm. In another embodiment, decreasing or inhibiting the production of toxic cytokine levels comprises ameliorating CRS or a cytokine storm. In another embodiment, the toxic cytokines comprise pro-inflammatory cytokines. In another embodiment, pro-inflammatory cytokines comprise IL-6. In another embodiment, proinflammatory cytokines comprise IL-1β. In another embodiment, pro-inflammatory cytokines comprise TNF-a. In another embodiment, pro-inflammatory cytokine comprise IL-6, IL-1β, or TNF-a, or any combination thereof.

In one embodiment, the dosing schedule of the immunotherapy agent and the amount of immunotherapy agent administrated to the subject is adjusted in order prevent life-threatening adverse effects, CRS, cytokine storm, sCRS and/or hypercytokinemia. In one embodiment, the C-Reactive Protein (CRP) levels in the subject are used to determine the amount of immunotherapy agent to be provided. In one embodiment, the first amount of the immunotherapy agent does not induce a life threatening adverse event within the subject. In one embodiment, the first amount of the immunotherapy agent is provided in an amount effective to obtain the C-Reactive Protein (CRP) levels in the blood from the subject to be at least about 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229 or 230 mg/L. In a preferred embodiment the CRP level is about 200 to about 220 mg/mL. In one embodiment, the first amount of the immunotherapy agent induces a transient fever at about 38° C., 39° C., 40° C., 41° C. or 42° C. In one embodiment the immunotherapy agent induces a transient fever that is for the duration of 1-2 hours. In one embodiment the immunotherapy agent induces a transient fever that is for the duration of 1-5 hours.

In one embodiment, the second amount of the immunotherapy agent does not induce hypercytokinemia. In one embodiment, the second amount of the immunotherapy agent does not induce a life threatening adverse event within the subject. In one embodiment, a second amount of the immunotherapy agent is provided in an amount effective to obtain the C-Reactive Protein (CRP) levels in the blood from the subject to be at least about 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179 or 180 mg/mL. In a preferred embodiment the CRP level is about 159 mg/mL to about 169 mg/mL. In one embodiment, the second amount of the immunotherapy agent does not induce hypercytokinemia nor a life threatening multiple organ dysfunction and adverse event characterized by cytokine storm.

In one embodiment, cytokine release syndrome is characterized by elevated levels of several inflammatory cytokines and adverse physical reactions in a subject such as low blood pressure, high fever and shivering. In one embodiment the In one embodiment, inflammatory cytokines comprise IL-6, IL-Iβ and TNF-a. In another embodiment, CRS is characterized by elevated levels of IL-6, IL-1β, or TNF-a, or any combination thereof. In another embodiment, CRS is characterized by elevated levels of IL-8, or IL-13, or any combination thereof. In another embodiment, a cytokine storm is characterized by increases in TNF-alpha, IFN-gamma, IL-1 beta, IL-2, IL-6, IL-8, IL-10, IL-13, GM-CSF, IL-5, fracktalkine, or a combination thereof or a subset thereof. In yet another embodiment, IL-6 comprises a marker of CRS or cytokine storm. In another embodiment, IFN-γ comprises a marker of CRS or cytokine storm. In another embodiment, patients with larger tumor burdens have higher incidence and severity of cytokine release syndrome.

In another embodiment, cytokines increased in CRS or a cytokine storm in 30 humans and mice may comprise any combination of cytokines listed in Tables 1 and 2 below.

TABLE 1

Panel of Cytokines Increased in CRS or Cytokine Storm in Humans and/or Mice

| Cytokine | Human | CAR-T (H) origin | Mouse origin | Not specified | Cells secreting this | Notes/ |
|---|---|---|---|---|---|---|
| Flt-3L | * | | | | DC (?) | |
| Fractalkine | * | | | | APC, Endothelial cells (?) | = CX3CL1 Neurotactin (Mouse) |
| M-CSF | | | | | | = CSF1 |
| GM-CSF | * | | | * (in vitro) | T cell, M0 | |
| IFN-a | * | | | | T cell, M0, Monocyte | |
| IFN-β | ? | | | ? | T cell, M0, Monocyte | |
| IFN-γ | * | * | | * (in vitro) | cytotoxic, T cells, helper T cells, NK cells, M0, Monocyte, DC | |
| IL-1a | * | | | | Monocyte, M0, Epithel | |
| IL-1β | * | | | * | Macrophages, DCs, fibroblasts, endothelial cells, hepatocytes | |
| IL-1Ra | * | | | | | |
| IL-2 | * | * | | * (in vitro) | T cells | |
| IL-2Ra | * | | | | lymphocytes | |
| IL-4 | * | * | | * (in vitro) | Th2 cells | |
| IL-5 | * | * | | * | T cells | |
| IL-6 | * | | * | * | monocytes/macrophages dendritic cells, T cells, fibroblasts, keratinocytes, endothelial cells, adipocytes, myocytes, mesangial cells, and osteoblasts | |
| IL-7 | * | | | * | in vitro by BM stromal cells | |
| IL-8 | * | | | | Macrophages, monocytes | |
| IL-9 | * | * | | | T cells, T helper | |
| IL-10 | * | * | | * (in vitro) | monocytes/macrophages mast cells, B cells, regulatory T cells and helper T cells | |
| IL-12 | * | | | * | M0, Monocyte, DC, activated lymphocytes, neutrophils | = p70 (p40 + p35) |
| IL-13 | * | * | | | T cells | |

In one embodiment, cytokines Flt-3L, Fractalkine, GM-CSF, IFN-γ, IL-1β, IL-2, IL-2Ra, IL-4, IL-5, IL-6, IL-7, IL-8, IL-9, IL-10, IL-12, and IL-13 of Table 15 are considered to be significant in CRS or cytokine storm. In another embodiment, IFN-a, 5 IFN-β, IL-1, and IL-1Ra of Table 1 appear to be important in CRS or cytokine storm. In another embodiment, M-CSF has unknown importance. In another embodiment, any cytokine listed in Table 1, or combination thereof, may be used as a marker of CRS or cytokine storm.

TABLE 2

Panel of Cytokines increased in CRS or Cytokine Storm in Humans and/or Mice

| Cytokine (Analyte) | Human model (clinical trials) | CAR-T (H) origin | Mouse origin | Not specified | Cells secreting this cytokine | Notes/ other |
|---|---|---|---|---|---|---|
| IL-15 | * | | | * | Fibroblasts, monocytes (?) | 22 |
| IL-17 | * | | | * | T cells | |
| IL-18 | | | | | Macrophages | |
| IL-21 | * | | | | T helper cells, NK cells | |
| IL-22 | * | | | | activated DC and T cells | |
| IL-23 | | | | | | |
| IL-25 | | | | | | Protective? |
| IL-27 | * | | | | APC | |
| IP-10 | * | | | | Monocytes (?) | |
| MCP-1 | * | | | | Endothel, fibroblast | = CXCL10 |
| MCP-3 | * | | | | PBMCs, M0 (?) | = CCL2 |

TABLE 2-continued

Panel of Cytokines increased in CRS or Cytokine Storm in Humans and/or Mice

| Cytokine (Analyte) | Human model (clinical trials) | Mouse model (pre-clinical) CAR-T (H) origin | Mouse origin | Not specified | Cells secreting this cytokine | Notes/ other |
|---|---|---|---|---|---|---|
| MIP-1α | * | | | * (in vitro) | T cells | = CXCL9 |
| MIP-1β | * | | | | T cells | = CCL3 |
| PAF | ? | | | | platelets, endotherlial cells, neutrophils, monocytes, and macrophages, mesangial cells | = CCL4 |
| PGE2 | * | | | * | Gastrointestinal mucosa and other | |
| RANTES | * | | | | Monocytes | |
| TGF-β | * | | | * | MØ, lymphocytes, endothel, platelets . . . | = CCL5 |
| TNF-α | * | * | * | * (in vitro) | Macrophages, NK cells, T cells | |
| TNF-αR1 | * | | | | | |
| HGF | | | | | | |
| MIG | * | | | | T cell chemoattractant, induces by IFN-γ | |

In one embodiment, IL-15, IL-17, IL-18, IL-21, IL-22, IP-10, MCP-1, MIP-1a, 5 MIP-1β, and TNF-a of Table 2 are considered to be significant in CRS or cytokine storm. In another embodiment, IL-27, MCP-3, PGE2, RANTES, TGF-β, TNF-aR1, and MIG of Table 2 appear to be important in CRS or cytokine storm. In another embodiment, IL-23 and IL-25 have unknown importance. In another embodiment, any cytokine listed in Table 2, or combination thereof, may be used as a marker of CRS or 10 cytokine storm.

A skilled artisan would appreciate that the term "cytokine" may encompass cytokines (e.g., interferon gamma, granulocyte macrophage colony stimulating factor, tumor necrosis factor alpha), chemokines (e.g., MIP 1 alpha, MIP 1 beta, RANTES), and other soluble mediators of inflammation, such as reactive oxygen species and nitric oxide.

In one embodiment, increased release of a particular cytokine, whether significant, important or having unknown importance, does not a prion mean that the particular cytokine is part of a cytokine storm. In one embodiment, an increase of at least one cytokine is not the result of a cytokine storm or CRS. In another embodiment, CAR T-cells may be the source of increased levels of a particular cytokine or group of cytokines.

In another embodiment, cytokine release syndrome is characterized by any or all of the following symptoms: Fever with or without rigors, malaise, fatigue, anorexia, myalgias, arthalgias, nausea, vomiting, headache Skin Rash, Nausea, vomiting, diarrhea, Tachypnea, hypoxemia Cardiovascular Tachycardia, widened pulse pressure, hypotension, increased cardiac output (early), potentially diminished cardiac output (late), Elevated D-dimer, hypofibrinogenemia with or without bleeding, Azotemia Hepatic Transaminitis, hyperbilirubinemia, Headache, mental status changes, confusion, delirium, word finding difficulty or frank aphasia, hallucinations, tremor, dymetria, altered gait, seizures. In another embodiment, a cytokine storm is characterized by IL-2 release and lymphoproliferation. In one embodiment, the cytokine storm is characterized by increases in cytokines released from a immunotherapy agent. In another embodiment, a cytokine storm is characterized by increases in cytokines released by CAR T-cells. In another embodiment, a cytokine storm is characterized by increases in cytokines released by cells other than CAR T-cells.

In another embodiment, cytokine storm leads to potentially life-threatening complications including cardiac dysfunction, adult respiratory distress syndrome, neurologic toxicity, renal and/or hepatic failure, and disseminated intravascular coagulation.

A skilled artisan would appreciate that the characteristics of a cytokine release syndrome (CRS) or cytokine storm are estimated to occur a few days to several weeks following the trigger for the CRS or cytokine storm. In one embodiment, an immunotherapy agent is a trigger for CRS or a cytokine storm. In one embodiment, CAR T-cells are a trigger for CRS or a cytokine storm. In another embodiment, a trigger for CRS or a cytokine storm is not CAR T-cells.

In one embodiment, measurement of cytokine levels or concentration, as an indicator of cytokine storm, may be expressed as –fold increase, percent (%) increase, net increase or rate of change in cytokine levels or concentration. In another embodiment, absolute cytokine levels or concentrations above a certain level or concentration may be an indication of a subject undergoing or about to experience a cytokine storm. In another embodiment, absolute cytokine levels or concentration at a certain level or concentration, for example a level or concentration normally found in a control subject not undergoing CAR-T cell therapy, may be an indication of a method for inhibiting or reducing the incidence of a cytokine storm in a subject undergoing CAR T-cell.

A skilled artisan would appreciate that the term "cytokine level" may encompass a measure of concentration, a measure of fold change, a measure of percent (%) change, or a measure of rate change. Further, the methods for measuring cytokines in blood, saliva, serum, urine, and plasma are well known in the art.

In one embodiment, despite the recognition that cytokine storm is associated with elevation of several inflammatory cytokines, IL-6 levels may be used as a common measure of cytokine storm and/or as a common measure of the effectiveness of a treatment for cytokine storms. A skilled artisan would appreciate that other cytokines may be used as markers of a cytokine storm, for example any of TNF-a, IB-1a, IL-6, IL-8, IL-13, or INF-γ, or any combination above may be used as a marker of CRS or a cytokine storm. Further, that assay methods for measuring cytokines are well known in the art. A skilled artisan would appreciate that methods affecting a cytokine storm may similarly affect cytokine release syndrome (CRS).

In one embodiment, cytokine release syndrome is graded. In another embodiment, Grade I describes cytokine release syndrome in which symptoms are not life threatening and require symptomatic treatment only, e.g., fever, nausea, fatigue, headache, myalgias, malaise. In another embodiment, Grade 2 symptoms require and respond to moderate intervention, such as oxygen, fluids or vasopressor for hypotension. In another embodiment, Grade 3 symptoms require and respond to aggressive intervention. In another embodiment, Grade 4 symptoms are life-threatening symptoms and require ventilator and patients display organ toxicity.

In another embodiment, a cytokine storm is characterized by IL-6 and interferon gamma release. In another embodiment, a cytokine storm is characterized by IL-6 release. In another embodiment, a cytokine storm is characterized by interferon gamma release. In another embodiment, a cytokine storm is characterized by release of any cytokine or combination thereof, listed in Tables 1 and 2. In another embodiment, a cytokine storm is characterized by release of any cytokine or combination thereof, known in the art.

In one embodiment, symptoms onset begins minutes to hours after the infusion of an immunotherapy agent begins. In another embodiment, symptoms coincide with peak cytokine levels.

In one embodiment, the method of treating a cancer comprises administering an immunotherapy agent. In one embodiment, the immunotherapy agent is a CAR T-cell. In one embodiment, a method of inhibiting or reducing the incidence of a cytokine release syndrome (CRS) or a cytokine storm in a subject undergoing CAR T-cell cancer therapy comprises administering an additional agent. In another embodiment, the additional agent may aid the CAR T-cell therapy. In another embodiment, the additional agent may aid in the inhibition or reducing the incidence of the CRS or cytokine storm. In another embodiment, the additional agent may aid in treating the CRS or cytokine storm. In another embodiment, the additional agent may aid in preventing the CRS or cytokine storm. In another embodiment, the additional agent may aid in ameliorating the CRS or cytokine storm. In another embodiment, the additional agent may aid in alleviating the CRS or cytokine storm.

In one embodiment, the additional agent for decreasing harmful cytokine release comprises apoptotic cells or a composition comprising said apoptotic cells. In another embodiment, the additional agent for decreasing harmful cytokine release comprises an apoptotic cell supernatant or a composition comprising said supernatant. In another embodiment, the additional agent for decreasing harmful cytokine release comprises a CTLA-4 blocking agent. In another embodiment, the additional agent for decreasing harmful cytokine release comprises immunotherapy agent, and a CTLA-4 blocking agent. In another embodiment, the additional agent for decreasing harmful cytokine release comprises an alpha-1 antitrypsin or fragment thereof or analogue thereof. In another embodiment, the additional agent for decreasing harmful cytokine release comprises immunotherapy agent, and an alpha-1 anti-trypsin or fragment thereof or analogue thereof. In another embodiment, the additional agent for decreasing harmful cytokine release comprises a tellurium-based compound. In another embodiment, the additional agent for decreasing harmful cytokine release comprises immunotherapy agent, and a tellurium-based compound. In another embodiment, the additional agent for decreasing harmful cytokine release comprises an immune modulating agent. In another embodiment, the additional agent for decreasing harmful cytokine release comprises immunotherapy agent, and an immune modulating agent. In another embodiment, the additional agent for decreasing harmful cytokine release comprises Treg cells. In another embodiment, the additional agent for decreasing harmful cytokine release comprises immunotherapy agent, and Treg cells.

In another embodiment, methods as disclosed herein utilize combination therapy of CAR T-cells with one or more CTLA-4-blocking agents such as Ipilimumab. In another embodiment, CTLA-4 is a potent inhibitor of T-cell activation that helps to maintain self-tolerance. In another embodiment, administration of an anti-CTLA-4 blocking agent, which in another embodiment, is an antibody, produces a net effect of T-cell activation. In another embodiment, compositions and methods as disclosed herein utilize combined therapy comprising apoptotic cells, CAR T-cells, and one or more CTLA-4-blocking agents.

In another embodiment, other toxicities resulting from CAR T-cell or NK cell administration that may be treated, prevented, inhibited, ameliorated, reduced in incidence or alleviated by the compositions and methods as disclosed herein comprise B cell aplasia or tumor lysis syndrome (TLS).

In one embodiment, a method of inhibiting or reducing the incidence of a cytokine release syndrome (CRS) or a cytokine storm in a subject undergoing CAR T-cell cancer therapy does not affect the efficacy of the CAR T-cell therapy. In another embodiment, a method of inhibiting or reducing the incidence of CRS or a cytokine storm in a subject undergoing CAR T-cell cancer therapy, does reduce the efficacy of the CAR T-cells therapy by more than about 5%. In another embodiment, a method of inhibiting or reducing the incidence of CRS or a cytokine storm in a subject undergoing CAR T-cell cancer therapy, does reduce the efficacy of the CAR T-cells therapy by more than about 10%. In another embodiment, a method of inhibiting or reducing the incidence of CRS or a cytokine storm in a subject undergoing CAR T-cell cancer therapy, does reduce the efficacy of the CAR T-cells therapy by more than about 15%. In another embodiment, a method of inhibiting or reducing the incidence of CRS or a cytokine storm in a subject undergoing CAR T-cell cancer therapy, does reduce the efficacy of the CAR T-cells therapy by more than about 20%.

Any appropriate method of quantifying cytotoxicity can be used to determine whether activity in an immune cell modified to express a CAR remains substantially unchanged. For example, cytotoxicity can be quantified using a cell culture-based assay such as the cytotoxic assays described in the Examples. Cytotoxicity assays can employ dyes that preferentially stain the DNA of dead cells. In other cases, fluorescent and luminescent assays that measure the relative number of live and dead cells in a cell population can be used. For such assays, protease activities serve as markers for cell viability and cell toxicity, and a labeled cell permeable peptide generates fluorescent signals that are proportional to the number of viable cells in the sample. Kits for various cytotoxicity assays are commercially available from manufacturers such as Promega and Life Technologies. In another embodiment, a measure of cytotoxicity may be qualitative. In another embodiment, a measure of cytotoxicity may be quantitative. In a further embodiment a measure of cytotoxicity may be related to the change in expression of a cytotoxic cytokine.

In one embodiment, the methods as disclosed herein comprise an additional step that is useful in overcoming rejection of allogeneic donor cells. In one embodiment, the methods comprise the step of full or partial lymphodepletion prior to administration of the CAR T-cells, which in one embodiment, are allogeneic CAR T-cells. In another embodiment, the lymphodepletion is adjusted so that it delays the host versus graft reaction for a period sufficient to allow said allogeneic T-cells to attack the tumor to which they are directed, but to an extent insufficient to require rescue of the host immune system by bone marrow transplantation. In another embodiment, agents that delay egression of the allogeneic T-cells from lymph nodes, such as 2-amino-2-2-[2-(4-octylphenyl)ethyl]propane-1,3-diol (FT-Y720), 5-[4-phenyl-5-(trifluoromethyl)thiophen-2-yl]-3-[3-(trifluoromethyl)phenyl-1]1,2,4-oxadiazole (SEW2871), 3-(2-(-hexylphenylamino)-2-oxoethylamino)propanoic acid (W123), 2-ammonio-4-(2-chloro-4-(3-phenoxyphenylthio)phenyl)-2-(hydroxymethyl)but-yl hydrogen phosphate (KRP-203 phosphate) or other agents known in the art, may be used as part of the compositions and methods as disclosed herein to allow the use of allogeneic CAR T-cells having efficacy and lacking initiation of graft vs host disease. In one embodiment, MHC expression by the allogeneic T-cells is silenced to reduce the rejection of the allogeneic cells. In another embodiment, the apoptotic cells prevent rejection of the allogeneic cells.

In one embodiment, a method of treating a cancer subject as disclosed herein includes administering an immunotherapy agent. In one embodiment the immunotherapy agent is a CAR-T cell, in one embodiment, CAR T-cells are heterologous to the subject. In one embodiment, CAR T-cells are derived from one or more donors. In one embodiment, CAR T-cells are derived from one or more bone marrow donors. In another embodiment, CAR T-cells are derived from one or more blood bank donations. In one embodiment, the donors are matched donors. In one embodiment, CAR T-cells are universal allogeneic CAR T-cells. In another embodiment, CAR T-cells are syngeneic CAR T-cells. In another embodiment, CAR T-cells are from unmatched third party donors in another embodiment, CAR T-cells are from pooled third party donor T-cells. In one embodiment, the donor is a bone marrow donor. In another embodiment, the donor is a blood bank donor. In one embodiment, CAR T-cells of the compositions and methods as disclosed herein comprise one or more MHC unrestricted tumor-directed chimeric receptors. In one embodiment, non-autologous T-cells may be engineered or administered according to protocols known in the art to prevent or minimize autoimmune reactions, such as described in U.S. Patent Application No. 2013015679, which is incorporated herein by references in its entirety.

In another embodiment, CAR. T-cells are autologous to the subject. In one embodiment, the patient's own cells are used. In this embodiment, if the patient's own cells are used, then the CAR T-cell therapy is administered after the immunotherapy agent.

According to some embodiments, the CAR-T cell is administered to the subject systemically. In another embodiment, administration is via the intravenous route. Alternately, the CAR-T cell may be administered to the subject according to various other routes, including, but not limited to, the parenteral, intraperitoneal, intra-articular, intramuscular and subcutaneous routes. Each possibility represents a separate embodiment as disclosed herein.

According to some embodiments, the CAR-T cell and an additional agent that decreases cytokine storm is administered to the subject systemically. In another embodiment, administration is via the intravenous route. Alternately, the CAR-T cell and an additional agent that decreases cytokine storm may be administered to the subject according to various other routes, including, but not limited to, the parenteral, intraperitoneal, intra-articular, intramuscular and subcutaneous routes. Each possibility represents a separate embodiment as disclosed herein.

In one embodiment, the preparation is administered in a local rather than systemic manner, for example, via injection of the preparation directly into a specific region of a patient's body. In another embodiment, a specific region comprises a tumor or cancer.

In another embodiment, the immunotherapy agent is administered to the subject suspended in a suitable physiological buffer, such as, but not limited to, saline solution, PBS, HBSS, and the like. In addition the suspension medium may further comprise supplements conducive to maintaining the viability of the cells. In another embodiment, the additional agent is administered to the subject suspended in a suitable physiological buffer, such as, but not limited to, saline solution, PBS, HBSS, and the like.

According to some embodiments the pharmaceutical composition is administered intravenously. According to another embodiment, the pharmaceutical composition is administered in a single dose. According to alternative embodiments the pharmaceutical composition is administered in multiple doses. According to another embodiment, the pharmaceutical composition is administered in two doses. According to another embodiment, the pharmaceutical composition is administered in three doses. According to another embodiment, the pharmaceutical composition is administered in four doses. According to another embodiment, the pharmaceutical composition is administered in five or more doses. According to some embodiments, the pharmaceutical composition is formulated for intravenous injection.

In one embodiment, any appropriate method of providing modified CAR-expressing immune cells to a subject can be used for methods described herein. In one embodiment, methods for providing cells to a subject comprise hematopoietic cell transplantation (HCT), infusion of donor-derived NK cells into cancer patients or a combination thereof.

The disclosure provides dosing regimens for treating a subject having cancer with a recombinant polypeptide (e.g., recombinant polypeptide CRYA_1B), and an agent that reduces IL-10 in a subject (e.g. IFNg). The dosage amounts of the recombinant polypeptide and the IFN gamma are described herein supra.

In one aspect, first dose of the agent and the first dose recombinant polypeptide is administered concurrently or sequentially. In one aspect, the first dose of recombinant polypeptide is administered at a period of time after the first dose of the agent. In one aspect, the first recombinant polypeptide is administered at about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 hours after the administration of the first dose of the agent. In a preferred aspect, the first dose of the recombinant polypeptide is administered at about 3 or 4 hours after the administration of the first dose of the agent. In one aspect, a second dose of the recombinant polypeptide is administered at about 15, 16, 17, 18, 19, 20, 21, 22, 23, 24, 25, 26, 27, 28, 29 or 30 hours after the administration of the first dose of the recombinant polypeptide. In a preferred aspect, the second dose of the recombinant polypeptide is administered at about 24 hours after the administration of the first recombinant polypeptide.

In one aspect, a second dose of the agent is administered at about 1, 2, 3, 4, 5, 6 or 7 days after the first dose of the agent. In a preferred aspect, the second dose of the agent is administered at about 4 days after the first dose of the agent. In one aspect, the third dose of recombinant polypeptide is administered at a period of time after the second dose of the agent. In one aspect, the third recombinant polypeptide is administered at about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 hours after the administration of the second dose of the agent. In a preferred aspect, the third dose of the recombinant polypeptide is administered at about 3 or 4 hours after the administration of the second dose of the agent. In one aspect, a fourth dose of the recombinant polypeptide is administered at about 15, 16, 17, 18, 19, 20, 21, 22, 23, 24, 25, 26, 27, 28, 29 or 30 hours after the administration of the third dose of the recombinant polypeptide. In a preferred aspect, the fourth dose of the recombinant polypeptide is administered at about 24 hours after the administration of the third recombinant polypeptide.

In one aspect, a third dose of the agent is administered at about 1, 2, 3, 4, 5, 6 or 7 days after the second dose of the agent. In a preferred aspect, the third dose of the agent is administered at about 4 days after the second dose of the agent. In one aspect, the fifth dose of recombinant polypeptide is administered at a period of time after the third dose of the agent. In one aspect, the fifth recombinant polypeptide is administered at about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 hours after the administration of the third dose of the agent. In a preferred aspect, the fifth dose of the recombinant polypeptide is administered at about 3 or 4 hours after the administration of the third dose of the agent. In one aspect, a sixth dose of the recombinant polypeptide is administered at about 15, 16, 17, 18, 19, 20, 21, 22, 23, 24, 25, 26, 27, 28, 29 or 30 hours after the administration of the fifth dose of the recombinant polypeptide. In a preferred aspect, the sixth dose of the recombinant polypeptide is administered at about 24 hours after the administration of the fifth recombinant polypeptide.

In one aspect, a fourth dose of the agent is administered at about 1, 2, 3, 4, 5, 6 or 7 days after the third dose of the agent. In a preferred aspect, the fourth dose of the agent is administered at about 4 days after the third dose of the agent. In one aspect, the seventh dose of recombinant polypeptide is administered at a period of time after the fourth dose of the agent. In one aspect, the seventh recombinant polypeptide is administered at about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 hours after the administration of the fourth dose of the agent. In a preferred aspect, the seventh dose of the recombinant polypeptide is administered at about 3 or 4 hours after the administration of the fourth dose of the agent. In one aspect, an eighth dose of the recombinant polypeptide is administered at about 15, 16, 17, 18, 19, 20, 21, 22, 23, 24, 25, 26, 27, 28, 29 or 30 hours after the administration of the seventh dose of the recombinant polypeptide. In a preferred aspect, the eighth dose of the recombinant polypeptide is administered at about 24 hours after the administration of the seventh recombinant polypeptide.

In one aspect of the present disclosure, the second dose of the recombinant polypeptide is administered at about 15, 16, 17, 18, 19, 20, 21, 22, 23, 24, 25, 26, 27, 28, 29 or 30 hours after the administration of the first dose of the recombinant polypeptide. In a preferred aspect, the second dose of the recombinant polypeptide is administered at about 24 hours after the administration of the first dose of the recombinant polypeptide.

In one aspect a third dose of the recombinant polypeptide is administered at about 1, 2, 3, 4, 5, 6 or 7 days after the second dose of the recombinant polypeptide. In a preferred aspect, the third dose of the recombinant polypeptide is administered at about 3 days after the second dose of the recombinant polypeptide. In one aspect, the fourth dose of the recombinant polypeptide is administered at about 15, 16, 17, 18, 19, 20, 21, 22, 23, 24, 25, 26, 27, 28, 29 or 30 hours after the administration of the third dose of the recombinant polypeptide. In a preferred aspect, the fourth dose of the recombinant polypeptide is administered at about 24 hours after the administration of the third dose of the recombinant polypeptide.

In one aspect a fifth dose of the recombinant polypeptide is administered at about 1, 2, 3, 4, 5, 6 or 7 days after the fourth dose of the recombinant polypeptide. In a preferred aspect, the fifth dose of the recombinant polypeptide is administered at about 3 days after the fourth dose of the recombinant polypeptide. In one aspect, the sixth dose of the recombinant polypeptide is administered at about 15, 16, 17, 18, 19, 20, 21, 22, 23, 24, 25, 26, 27, 28, 29 or 30 hours after the administration of the fifth dose of the recombinant polypeptide. In a preferred aspect, the sixth dose of the recombinant polypeptide is administered at about 24 hours after the administration of the fifth dose of the recombinant polypeptide.

In one aspect a seventh dose of the recombinant polypeptide is administered at about 1, 2, 3, 4, 5, 6 or 7 days after the sixth dose of the recombinant polypeptide. In a preferred aspect, the seventh dose of the recombinant polypeptide is administered at about 3 days after the sixth dose of the recombinant polypeptide. In one aspect, the eighth dose of the recombinant polypeptide is administered at about 15, 16, 17, 18, 19, 20, 21, 22, 23, 24, 25, 26, 27, 28, 29 or 30 hours after the administration of the seventh dose of the recombinant polypeptide. In a preferred aspect, the eighth dose of the recombinant polypeptide is administered at about 24 hours after the administration of the seventh dose of the recombinant polypeptide.

Any of the above aspects can be combined with any other aspect as disclosed herein.

EXAMPLES

Example 1: Methods of Producing Recombinant Polypeptides

Materials and Methods

The methods of producing the recombinant polypeptides of the present disclosure utilized the PCR primers disclosed in Table 3.

TABLE 3

Primer Sequences

| Primer | Nucleotide Sequence (5' to 3') | SEQ ID NO: |
|---|---|---|
| A1 | GGGGGGCATATGGACATTACCATCCAGCACCCCTGGTTCAAGCGCGCTCT | 33 |
| A2 | GGGGGGAAGCTTTTACTCCTCAGGCGCCTCGGTGGGCTT | 34 |
| ioE1 | CCTCTGTTCGAGGAGACTATCGAGCCCTACTA | 35 |
| ioE2 | TAGTAGGGCTCGATAGTCTCCTCGAACAGAGG | 36 |
| ioE3 | ACCGGCAGGAGCTGTTCCGCGAGGTGCTGTCGGAGGGCATTGAGTCGGTGAGGGAGGACCGGGA | 37 |
| ioE4 | TCCCGGTCCTCCCTCACCGACTCAATGCCCTCCGACAGCACCTCGCGGAACAGCTCCTGCCGGT | 38 |
| ioE5 | ACTATGCTGGACGTAAAACACTTTGAGCCTTCGGACCTGGAGGTGAAGATTA | 39 |
| ioE6 | TAATCTTCACCTCCAGGTCCGAAGGCTCAAAGTGTTTTACGTCCAGCATGAT | 40 |
| ioE7 | AAGATTATCGACGACTTTGTGTCGATCCATGGC | 41 |
| ioE8 | GCCATGGATCGACACAAAGTCGTCGATAATCTT | 42 |
| ioE9 | GGCAAGCACGAGTCGAGACAGGACGACCACGGCTACATCGAGCGGTCGTTTCACCGC | 43 |
| ioE10 | GCGGTGAAACGACCGCTCGATGTAGCCGTGGTCGTCCTGTCTCGACTCGTGCTTGCC | 44 |
| ioE11 | GCGGACCAGGAGGCCATCACCTGCGAGCTGGAGGGCGACGG | 45 |
| ioE12 | CCGTCGCCCTCCAGCTCGCAGGTGATGGCCTCCTGGTCCAC | 46 |
| ioE13 | TTCGACCAGTTTTTCGGATCGGGTCTGCTGTCGTATGACCTGCTGCCTCTGTTC | 47 |
| ioE14 | GGGGACCTTGGGGCCCTCGAAGGTCAGCATGCCGTCGCC | 48 |
| ioE15 | TTCAAGCGCGCTCTGGGACCCCTGATTCCAGAGCGTCTGTTCGACCAGTTTTTCGGA | 49 |
| ioE16 | CACGGGGATGGGCCTCGACTCGTGGGTGGGGTCCATGTTCTCGGGGACCTTGGGG | 50 |
| ioE17 | ATGGACATTACCATCCAG | 51 |
| ioE18 | AAGCTTTTACTCCTCAGGCGCCTCGGTGGGCTTCGACGACCGCTCCACGGGGATGGGCCT | 52 |

Preparation of Template DNA

The full length CRYAA sequence from *Anser cygnoides domesticus* (SEQ ID NO: 17) was amplified in a PCR reaction using Pfu polymerase. A1 primer (SEQ ID NO: 33) and A2 primer (SEQ ID NO: 34) were used in the PCR reaction. The gene was cloned into NdeI and HindIII sites in a pET24a vector (Novagen) using the manufacturer's protocol. The ligation mixture was transformed into *Escherichia coli* DH5alpha cells and transformants were selected on LB ampicillin plates. Plasmid DNA was isolated from several transformants and screened by restriction digestion of NdeI and HindIII sites. A sequence verified clone containing *Anser cygnoides domesticus* CRYAA (SEQ ID NO: 17) was identified and used as template.

Cloning of Plasmid Containing the CRYA_1B Recombinant Polypeptide Sequence

The recombinant plasmid containing CRYA_1B (SEQ ID NO: 25) was prepared in the following manner. PCR was performed using the template DNA described above, forward primer IoE1 (SEQ ID NO: 35) and reverse primer IoE2 (SEQ ID NO: 36). PCR temperature and time were programmed as follows: denaturing at 95° C. for 5 minutes; followed by 30 cycles of PCR reactions with denaturation at 95° C. for 30 sec, annealing at 60° C. for 30 sec, and elongation at 72° C. for 1 minute; final elongation at 72° C. for 10 minutes. All PCR amplifications were performed with Pfu Ultra polymerase (Stratagene). PCR products were separated electrophoretically using 1.0% agarose gel, and stained with ethidium bromide. The DNA fragment was extracted from the gel using GFX™ PCR DNA and Gel Band Purification Kit (GE Healthcare) and ligated into a pET24a (Novagen) vector. The ligation mixture was transformed into the DH5alpha *Escherichia coli* strain and transformants were selected on LB plates containing ampicillin. Plasmid DNA was isolated from transformants. A sequence verified clone, Plasmid_1, was used as a template for a subsequent round of PCR amplification.

PCR amplification was performed using Plasmid_1, forward primer IoE3 (SEQ ID NO: 37) and reverse primer IoE4 (SEQ ID NO: 38). PCR amplification and cloning were performed using the procedure described above and the following PCR conditions: 95° C. for 5 minutes, 32 cycles of (95° C. for 30 seconds, 65° C. for 30 seconds, 72° C. for 1 minute), followed by 5 minutes at 72° C. The PCR product was purified and cloned into a pET24a plasmid using NdeI and HindIII restriction sites. A sequence verified clone, Plasmid_2, was used as a template for a subsequent round of PCR amplification.

PCR amplification was performed using Plasmid_2, forward primer IoE5 (SEQ ID NO: 39) and reverse primer IoE6 (SEQ ID NO: 40). PCR amplification and cloning were performed using the procedure described above and the following PCR conditions: 95° C. for 5 minutes, followed by 95° C. for 30 seconds, 58° C. for 30 seconds, 72° C. for 1 minute in 35 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_3, was used as a template for a subsequent round of PCR amplification.

PCR amplification was performed using Plasmid_3, forward primer IoE7 (SEQ ID NO: 41) and reverse primer IoE8 (SEQ ID NO: 42). PCR amplification and cloning were performed using the procedure described above and the following PCR conditions: 95° C. for 5 minutes, followed by 95° C. for 30 seconds, 55° C. for 30 seconds, 72° C. for 1 minute in 28 cycles, with a final 5 minute extension at 72°

C. PCR products were separated electrophoretically using 1.0% agarose gel, and stained with ethidium bromide. The DNA fragment was excised from the gel, extracted and cloned into a pET24a plasmid. A sequence verified clone, Plasmid_4, was used as a template for a subsequent round of PCR amplification.

PCR amplification was performed using Plasmid_4, forward primer IoE9 (SEQ ID NO: 43) and reverse primer IoE10 (SEQ ID NO: 44). PCR amplification and cloning were performed using the procedure described above and the following PCR conditions: 95° C. for 5 minutes, followed by 95° C. for 30 seconds, 53° C. for 30 seconds, 72° C. for 1 minute in 33 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_5, was used as a template for a subsequent round of PCR amplification.

PCR amplification was performed using Plasmid_5, forward primer IoE11 (SEQ ID NO: 45) and reverse primer IoE12 (SEQ ID NO: 46). PCR amplification and cloning were performed using the procedure described above and the following PCR conditions: 95° C. for 5 minutes, followed by 95° C. for 30 seconds, 57° C. for 30 seconds, 72° C. for 1 minute in 30 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_6, was used as a template for a subsequent round of PCR amplification.

PCR amplification was performed using Plasmid_6, forward primer IoE13 (SEQ ID NO: 47) and reverse primer IoE14 (SEQ ID NO: 48). PCR amplification and cloning were performed using the procedure described above and the following PCR conditions: 95° C. for 5 minutes, followed by 95° C. for 30 seconds, 51° C. for 30 seconds, 72° C. for 1 minute in 32 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_7, was used as a template for a subsequent round of PCR amplification.

PCR amplification was performed using Plasmid_7, forward primer IoE15 (SEQ ID NO: 49) and reverse primer IoE16 (SEQ ID NO: 50). PCR amplification and cloning were performed using the procedure described above and the following PCR conditions: 95° C. for 5 minutes, followed by 95° C. for 30 seconds, 54° C. for 30 seconds, 72° C. for 1 minute in 32 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. A sequence verified clone, Plasmid_8, was used as a template for a subsequent round of PCR amplification.

PCR amplification was performed using Plasmid_8, forward primer IoE17 (SEQ ID NO: 51) and reverse primer IoE18 (SEQ ID NO: 52). PCR amplification and cloning were performed using the procedure described above and the following PCR conditions: 95° C. for 5 minutes, followed by 95° C. for 30 seconds, 52° C. for 30 seconds, 72° C. for 1 minute in 32 cycles, with a final 5 minute extension at 72° C. PCR products were separated electrophoretically using 1.0% agarose gel, and stained with ethidium bromide. The DNA fragment was excised from the gel, extracted and cloned into a pET24a plasmid. The ligation mixture was transformed into DH5alpha strain of *Escherichia coli* cells and transformants were selected on LB plates containing ampicillin. A sequence verified clone, Plasmid_9 contains the CRYA_1B (SEQ ID NO: 25) in the correct reading frame.

Expression of Recombinant Polypeptide CRYA_1B

Figure 2:
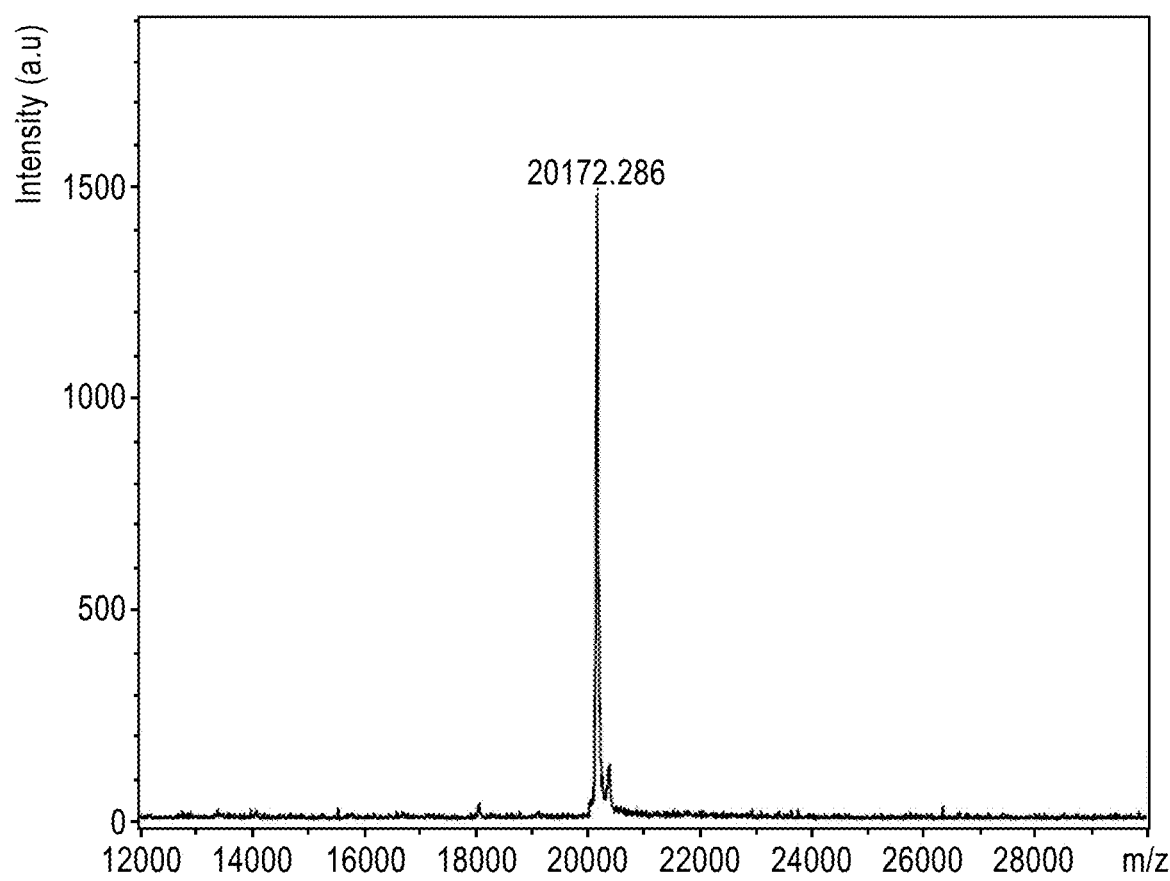
FIG. 2 shows a graph depicting the molecular weight of CRYA_1B recombinant polypeptide (SEQ ID NO: 9) of about 20 kDa as determined by mass spectrometry.
Figure 3A:
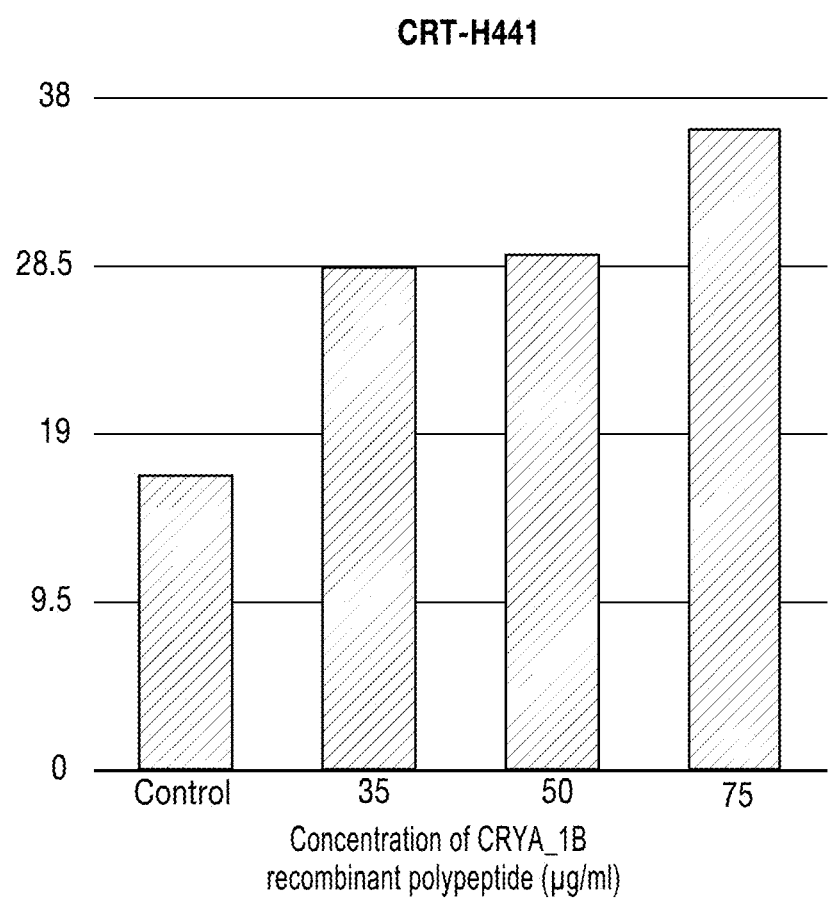
FIG. 3A shows a bar graph quantifying the percentage of cells that express CRT (Calreticulin) following treatment of H441 human lung cancer cell lines (HTB-174, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the H441 cells were incubated for 1 hour at 37° C. The CRT-expressing H441 cells were determined by FACSCalibur (BD Biosciences) flow cytometry using CRT mAb (Abcam).
Figure 3B:
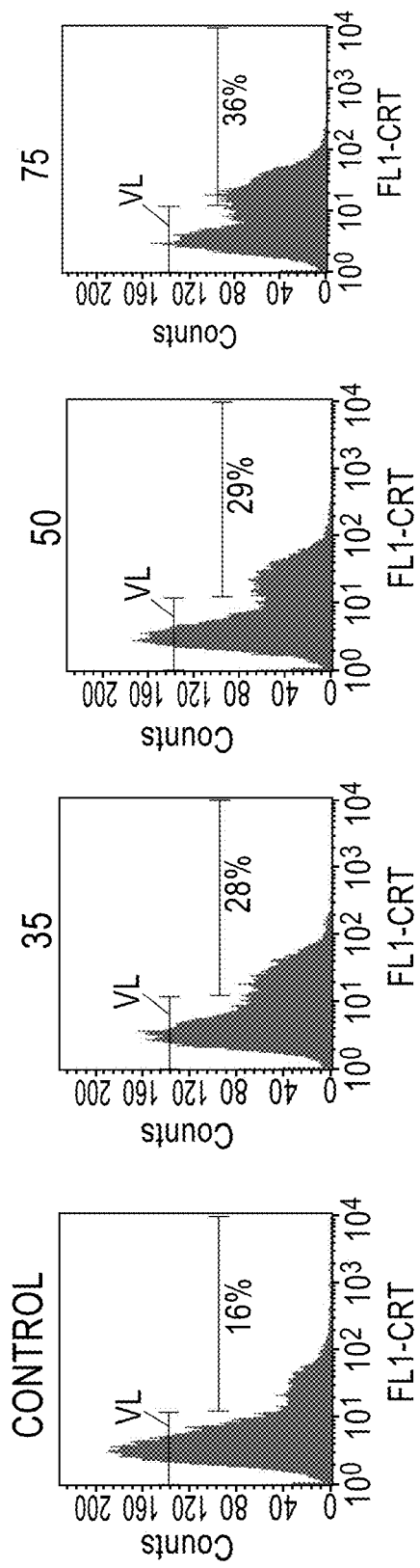
FIG. 3B shows the flow cytometry profiles used for quantification.
Figure 5A:
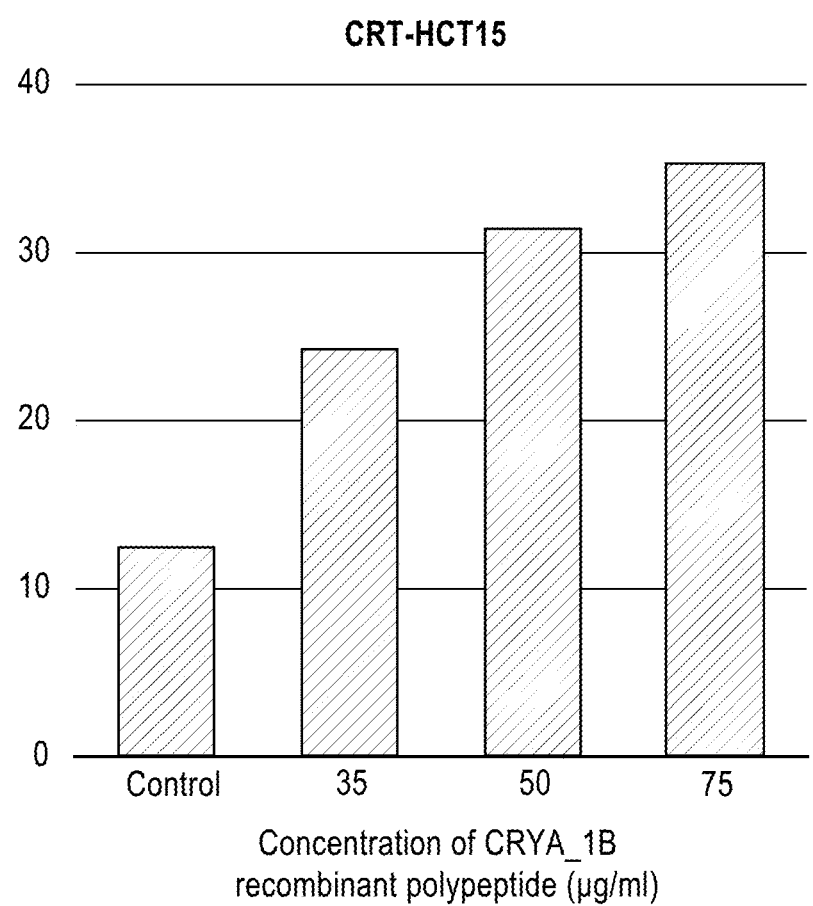
FIG. 5A shows a bar graph quantifying the percentage of cells that express CRT following treatment of HCT15 human colon cancer cell lines (CCL-225, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 g/ml and the HCT15 cells were incubated for 55 minutes at 37° C. The CRT-expressing HCT15 cells were determined by FACSCalibur (BD Biosciences) flow cytometry using CRT mAb (Abcam).
Figure 6A:
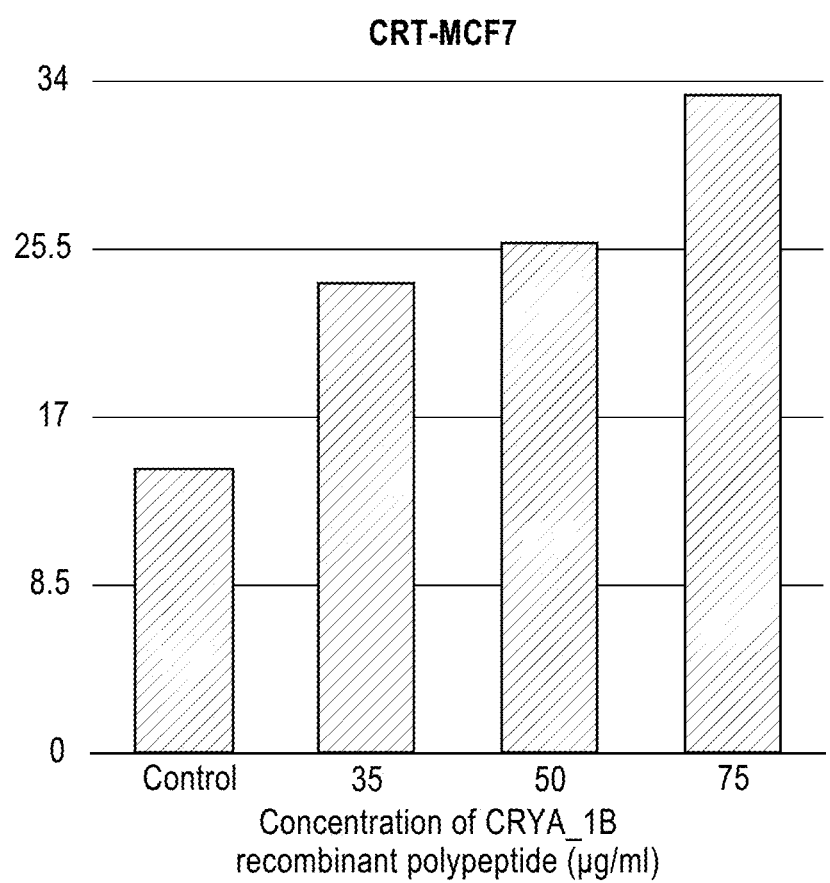
FIG. 6A shows a bar graph quantifying the percentage of cells that express CRT following treatment of MCF7 human breast cancer cell lines (HTB-22, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 g/ml and the MCF7 cells were incubated for 1 hour and 10 minutes at 37° C. The CRT-expressing MCF7 cells were determined by FACSCalibur (BD Biosciences) flow cytometry using CRT mAb (Abcam).
Figure 6B:
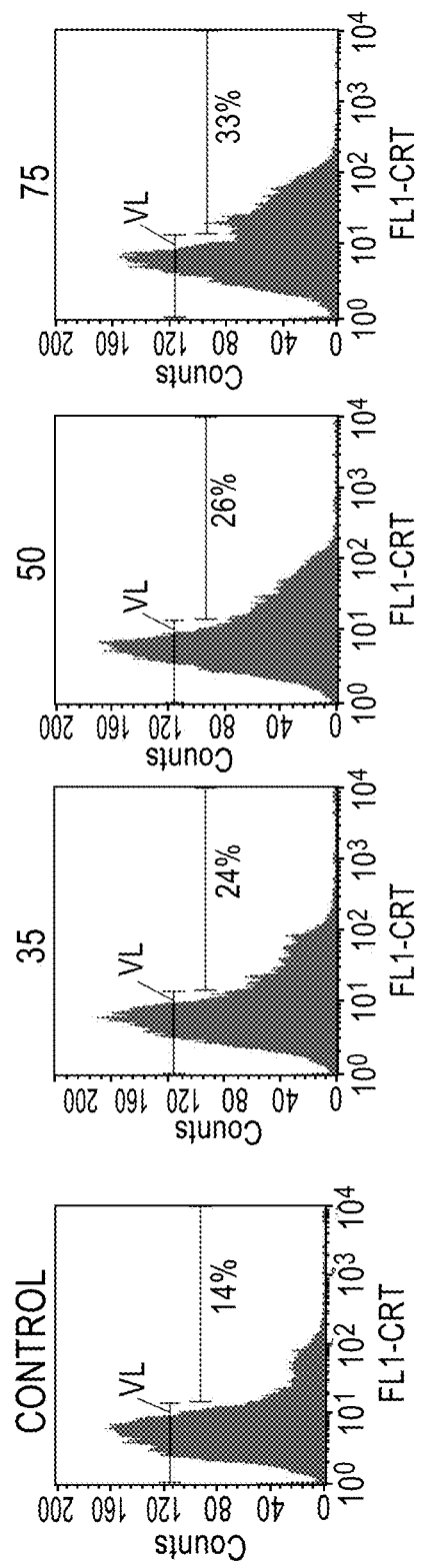
FIG. 6B shows the flow cytometry profiles used for quantification.
Figure 7A:
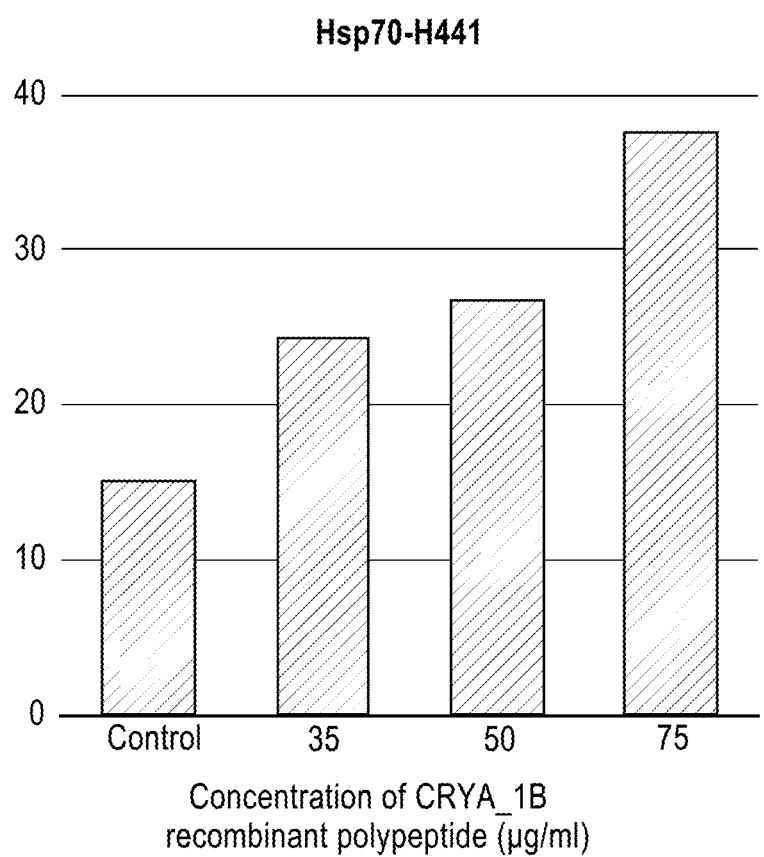
FIG. 7A shows a bar graph quantifying the percentage of cells that express HSP70 (70 kDa heat shock protein) following treatment of H441 human lung cancer cell lines (HTB-174, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the H441 cells were incubated for 1 hour and 50 minutes at 37° C. The Hsp70-expressing H441 cells were determined by FACSCalibur (BD Biosciences) flow cytometry using Hsp70 mAb (Enzo Life Sciences).
Figure 7B:
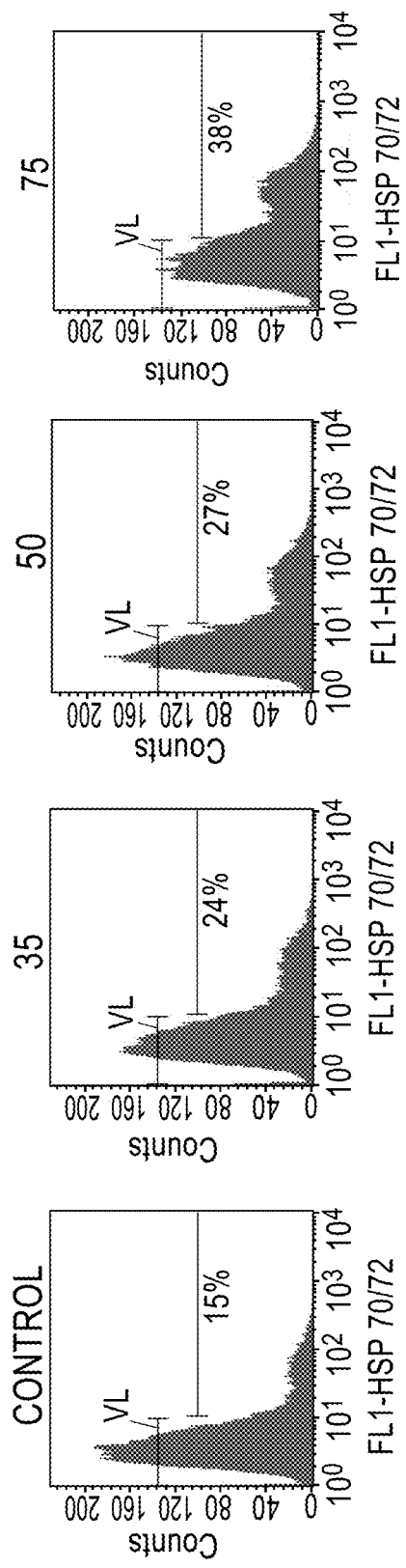
FIG. 7B shows the flow cytometry profiles used for quantification.
Figure 8A:
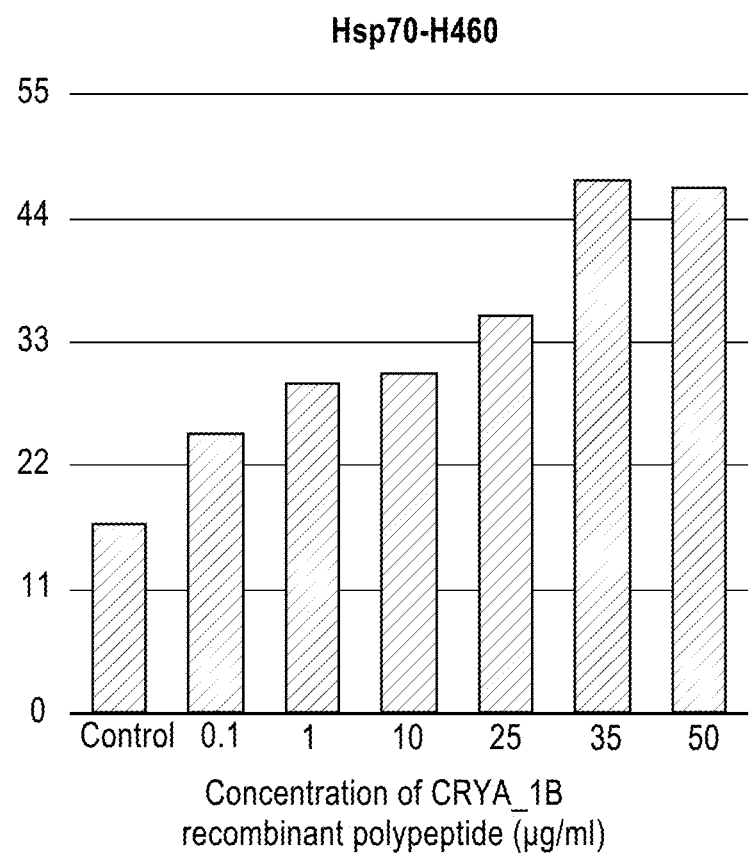
FIG. 8A shows a bar graph quantifying the percentage of cells that express HSP70 following treatment of H460 human lung cancer cell lines (HTB-177, ATCC) with various concentrations of CRYA_1B recombinant polypeptide (SEQ ID NO: 9). The stock CRYA_1B recombinant polypeptide (SEQ ID NO: 9) was diluted to the final concentration of 0.1, 1, 10, 25, 35, 50 µg/ml and the H460 cells were incubated for 1 hour and 15 minutes at 37° C. The Hsp70-expressing H460 cells were determined by FACSCalibur (BD Biosciences) flow cytometry using Hsp70 mAb (Enzo Life Sciences).
Figure 8B:
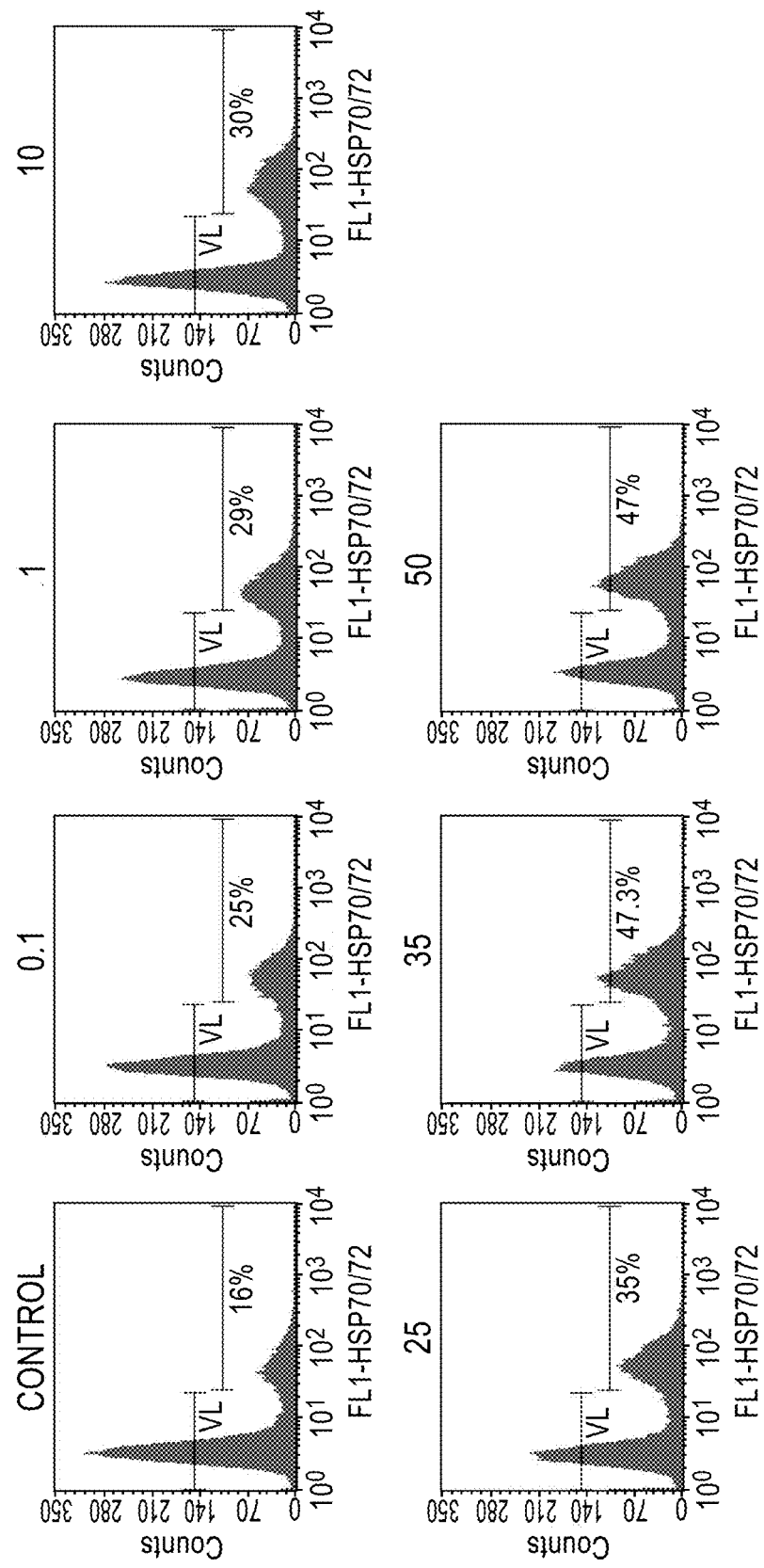
FIG. 8B shows the flow cytometry profiles used for quantification.
Figure 9A:
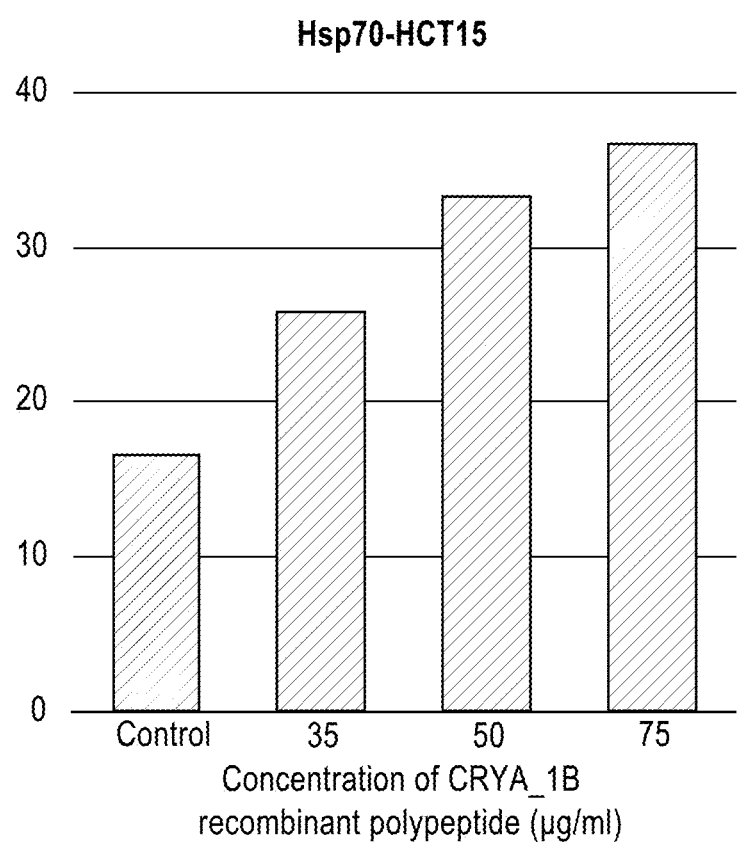
FIG. 9A shows a bar graph quantifying the percentage of cells that express HSP70 following treatment of HCT15 human colon cancer cell lines (CCL-225, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 g/ml and the HCT15 cells were incubated for 1 hour and 50 minutes at 37° C. The Hsp70-expressing HCT15 cells were determined by FACSCalibur (BD Biosciences) flow cytometry using Hsp70 mAb (Enzo Life Sciences).
Figure 9B:
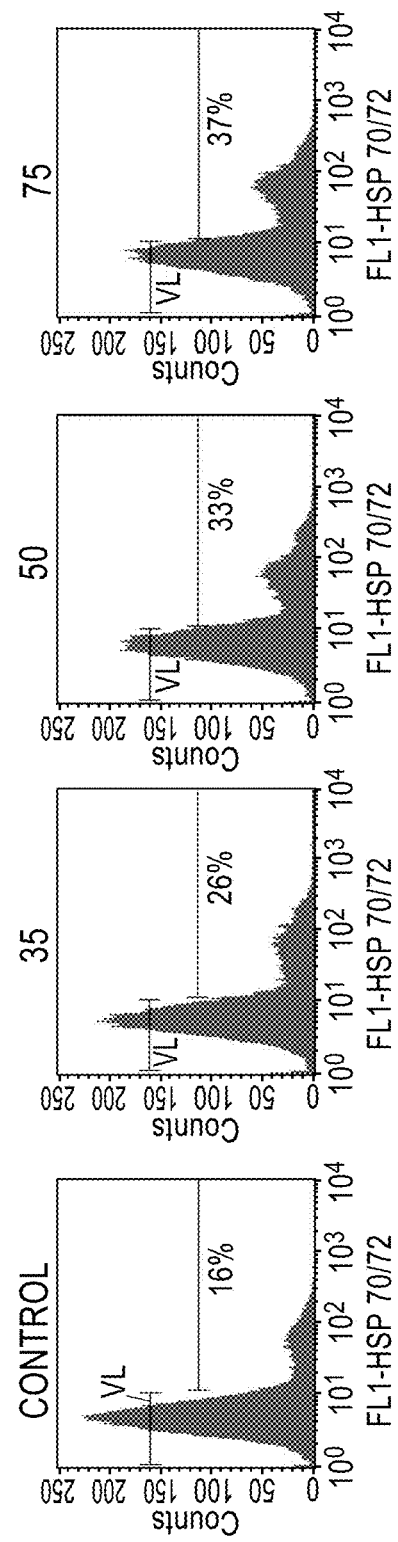
FIG. 9B shows the flow cytometry profiles used for quantification.
Figure 10A:
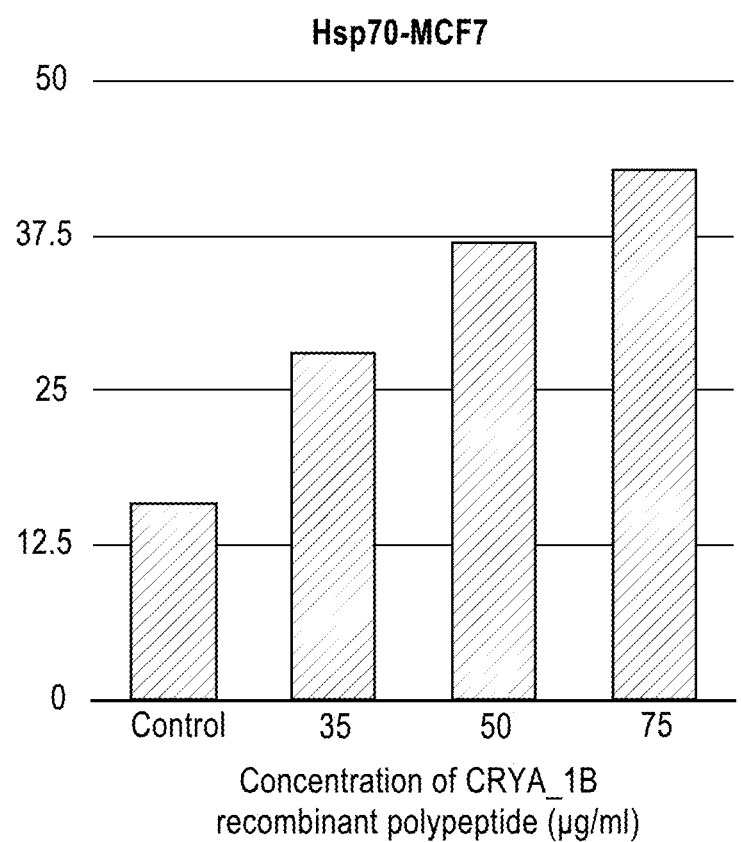
FIG. 10A shows a bar graph quantifying the percentage of cells that express HSP70 following treatment of MCF7 human breast cancer cell lines (HTB-22, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 g/ml and the MCF7 cells were incubated for 1 hour and 40 minutes at 37° C. The Hsp70-expressing MCF7 cells were determined by FACSCalibur (BD Biosciences) flow cytometry using Hsp70 mAb (Enzo Life Sciences).
Figure 10B:
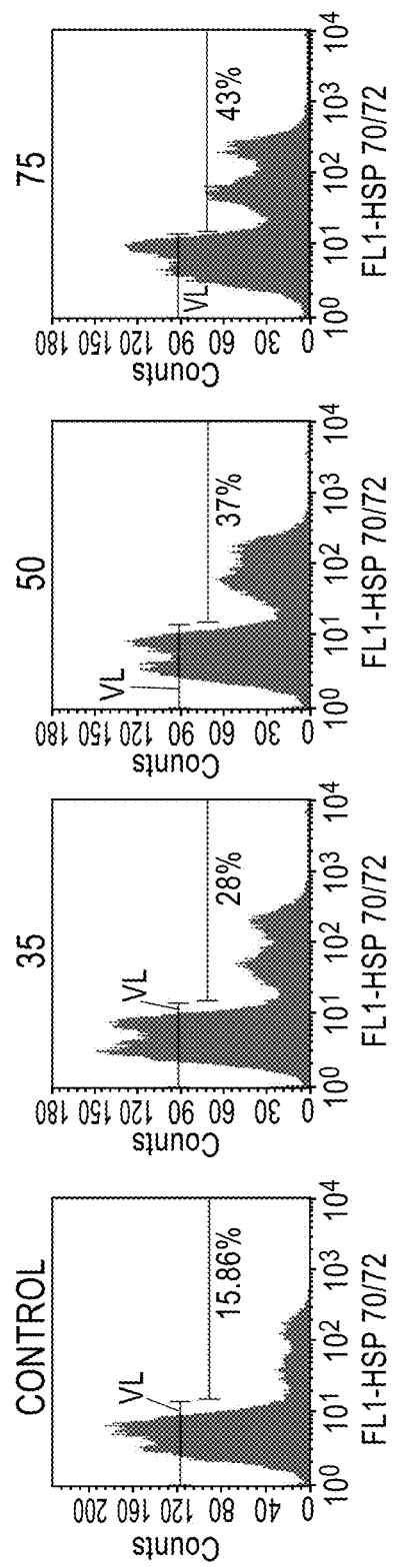
FIG. 10B shows the flow cytometry profiles used for quantification.
Figure 11A:
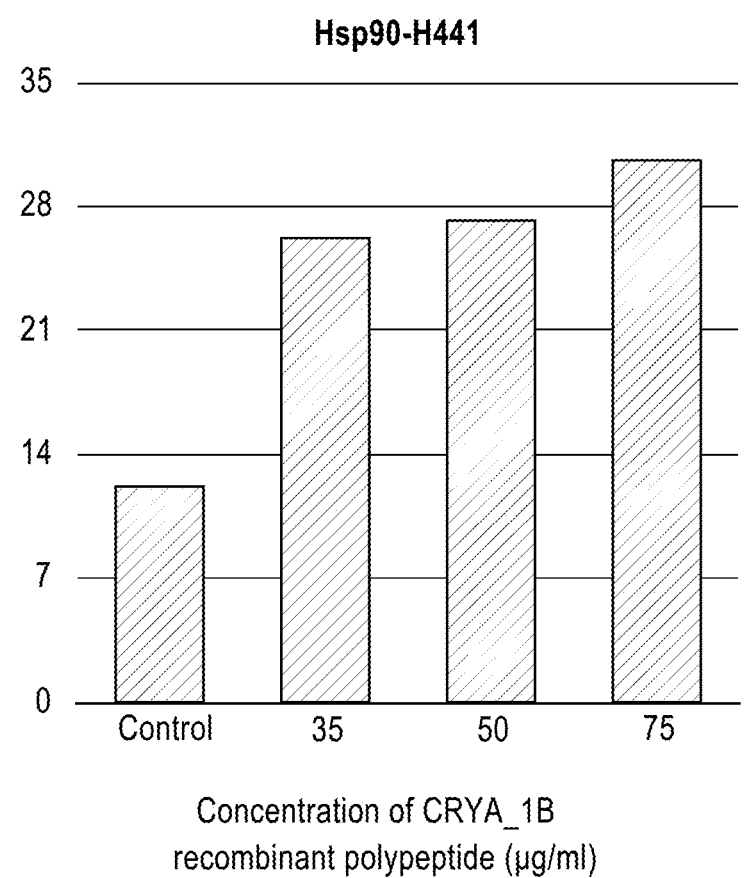
FIG. 11A shows a bar graph quantifying the percentage of cells that express HSP90 (90 kDa heat shock protein) following treatment of H441 human lung cancer cell lines (HTB-174, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the H441 cells were incubated for 1 hour and 40 minutes at 37° C. The Hsp90-expressing H441 cells were determined by FACSCalibur (BD Biosciences) flow cytometry using Hsp90 mAb (Enzo Life Sciences).
Figure 11B:
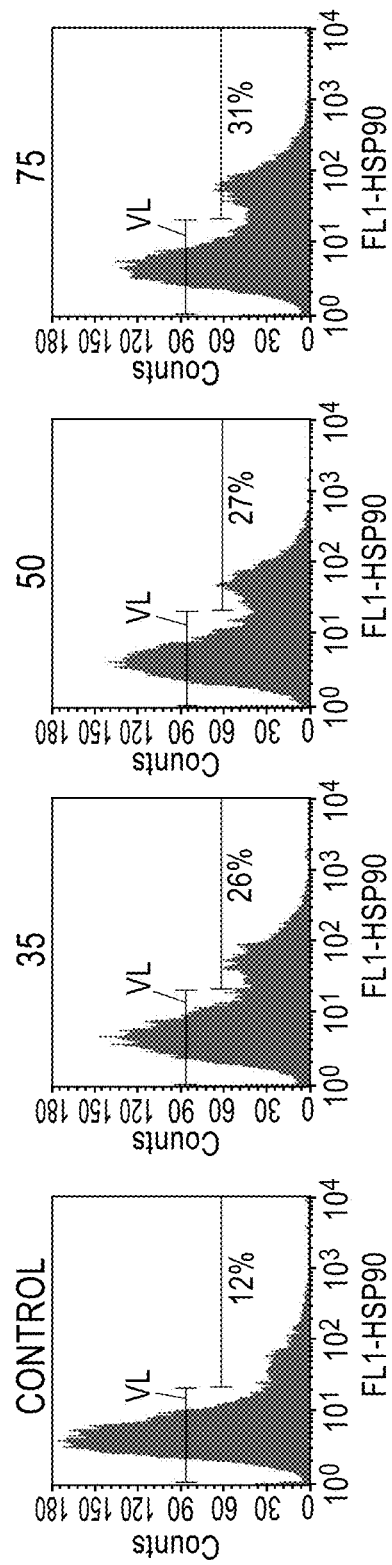
FIG. 11B shows the flow cytometry profiles used for quantification.
Figure 12A:
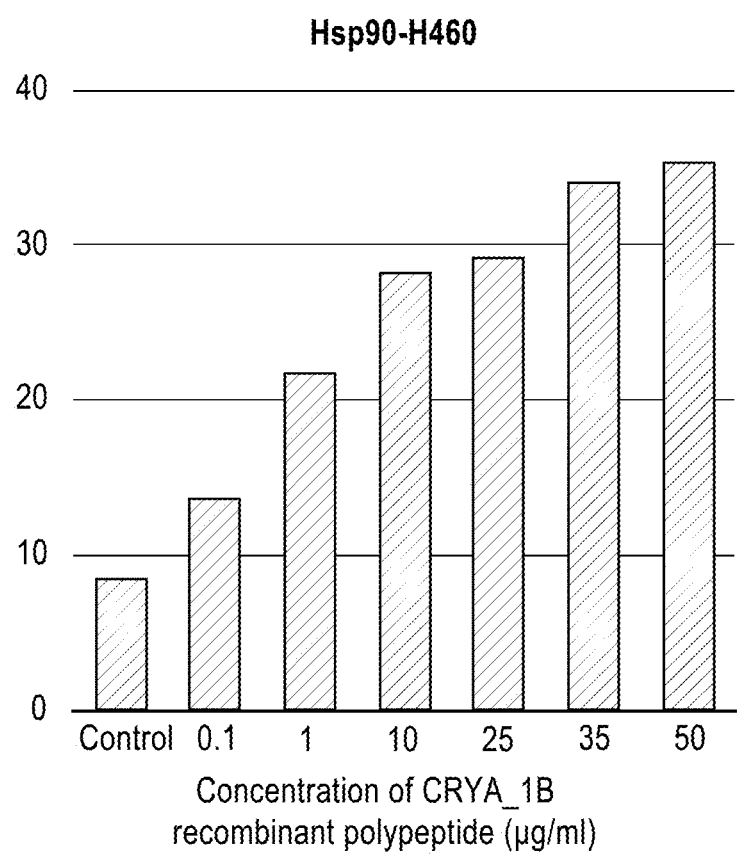
FIG. 12A shows a bar graph quantifying the percentage of cells that express HSP90 following treatment of H460 human lung cancer cell lines (HTB-177, ATCC) with various concentrations of CRYA_1B recombinant polypeptide (SEQ ID NO: 9). The stock CRYA_1B recombinant polypeptide (SEQ ID NO: 9) was diluted to the final concentration of 0.1, 1, 10, 25, 35, 50 µg/ml and the H460 cells were incubated for 1 hour and 5 minutes at 37° C. The Hsp90-expressing H460 cells were determined by FACSCalibur (BD Biosciences) flow cytometry using Hsp90 mAb (Enzo Life Sciences).
Figure 12B:
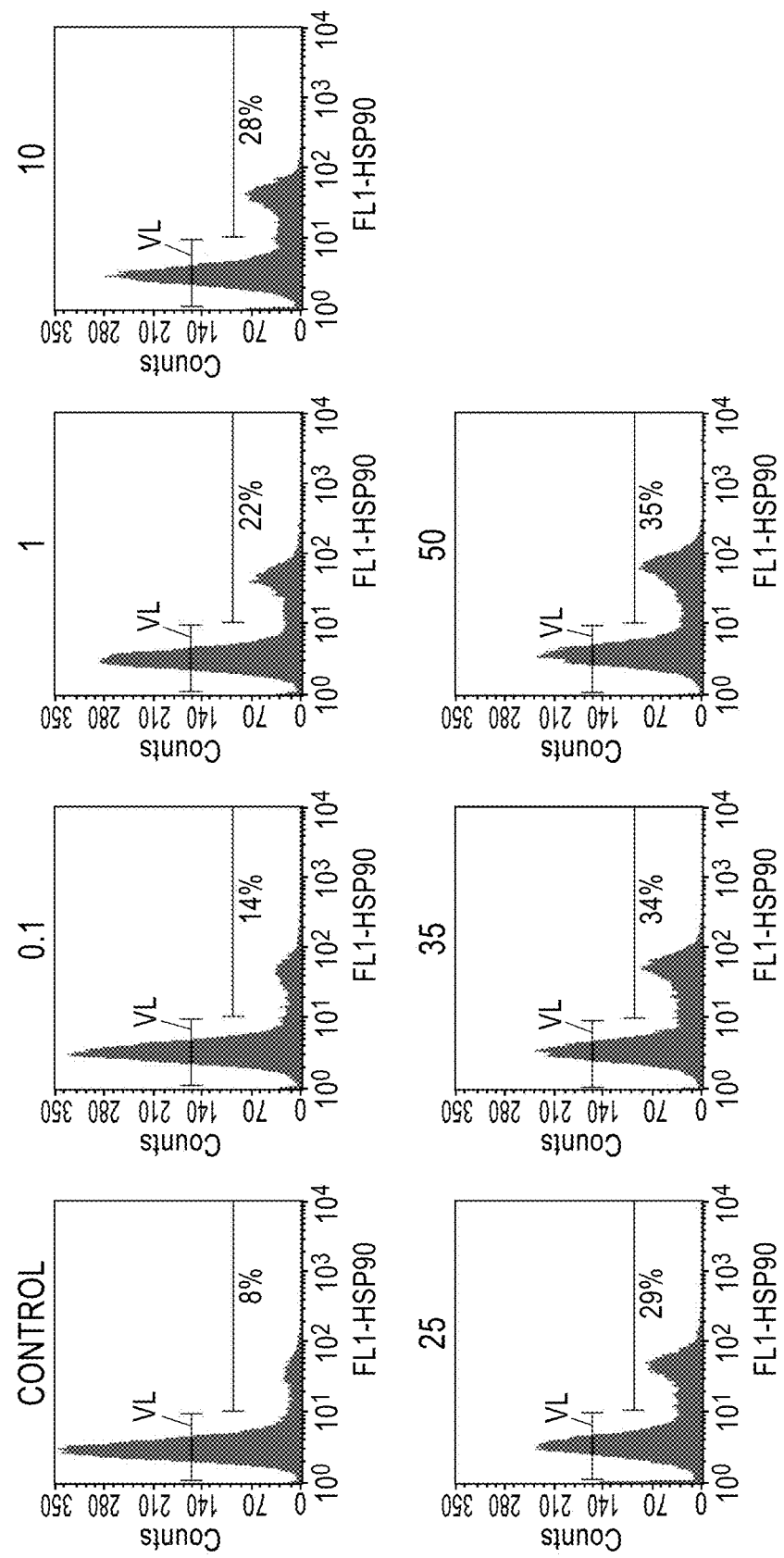
FIG. 12B shows the flow cytometry profiles used for quantification.
Figure 13A:
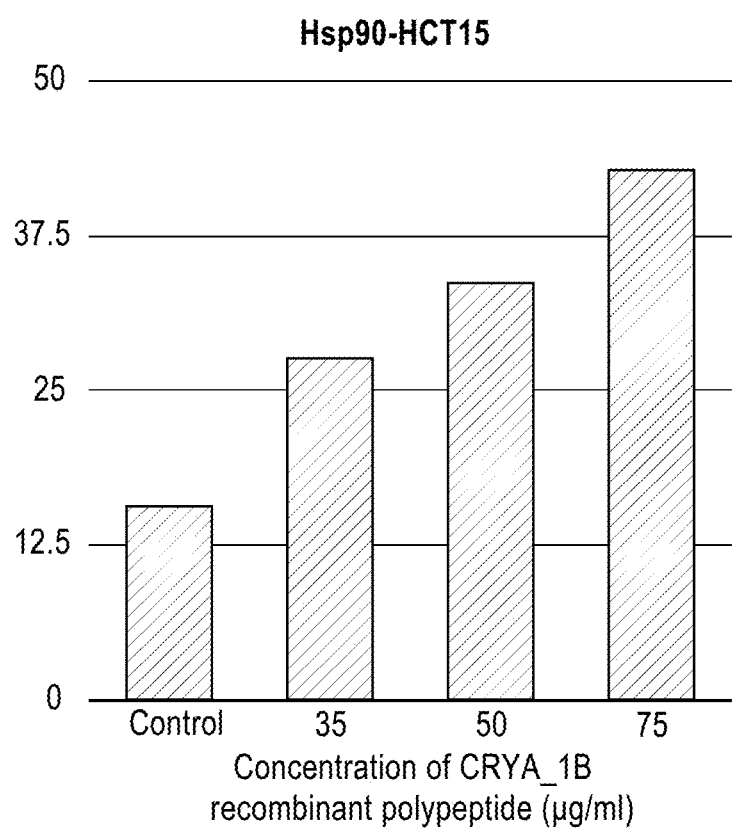
FIG. 13A shows a bar graph quantifying the percentage of cells that express HSP90 following treatment of HCT15 human colon cancer cell lines (CCL-225, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 g/ml and the HCT15 cells were incubated for 1 hour and 30 minutes at 37° C. The Hsp90-expressing HCT15 cells were determined by FACSCalibur (BD Biosciences) flow cytometry using Hsp90 mAb (Enzo Life Sciences).
Figure 13B:
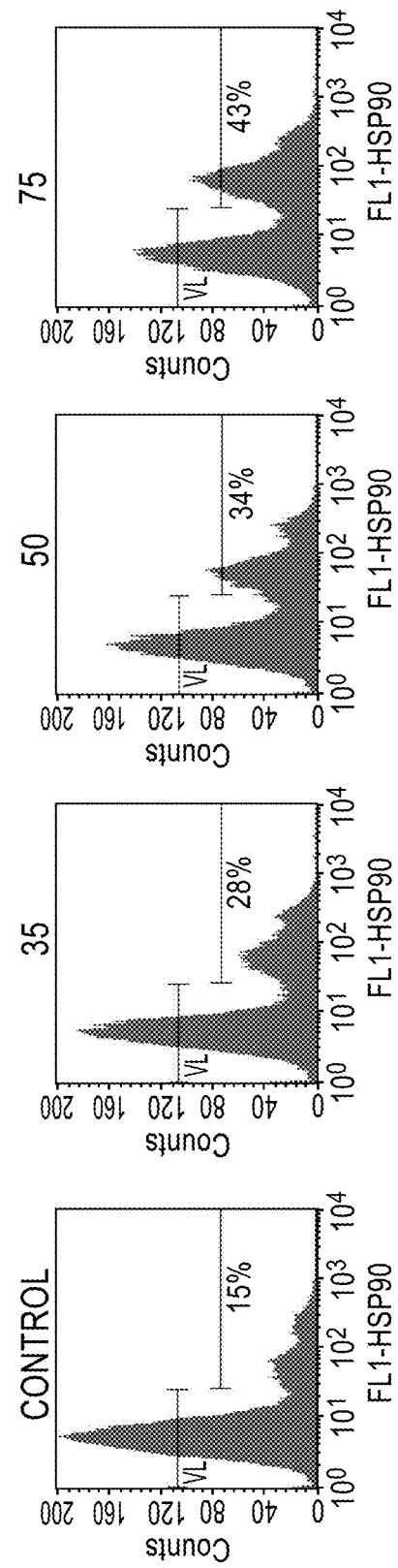
FIG. 13B shows the flow cytometry profiles used for quantification.
Figure 14A:
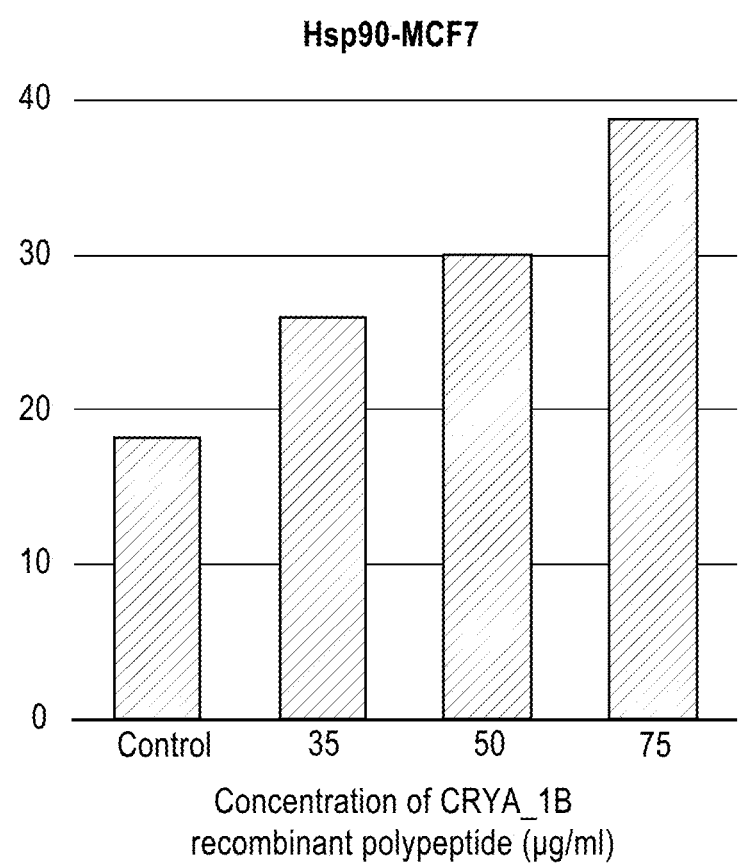
FIG. 14A shows a bar graph quantifying the percentage of cells that express HSP90 following treatment of MCF7 human breast cancer cell lines (HTB-22, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 g/ml and the MCF7 cells were incubated for 1 hour and 45 minutes at 37° C. The Hsp90-expressing MCF7 cells were determined by FACSCalibur (BD Biosciences) flow cytometry using Hsp90 mAb (Enzo Life Sciences).
Figure 14B:
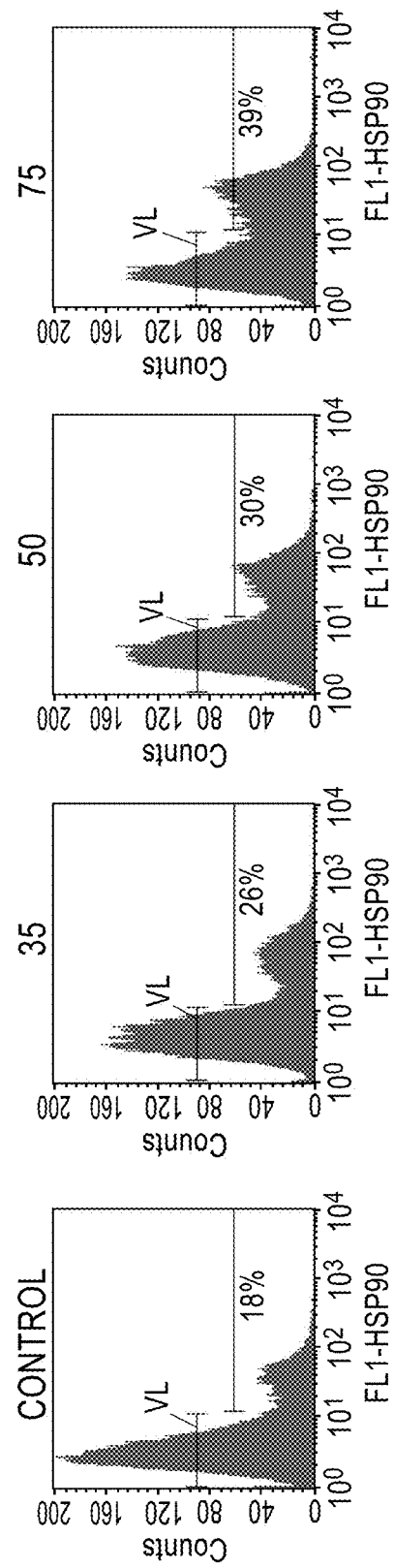
FIG. 14B shows the flow cytometry profiles used for quantification.
Figure 15A:
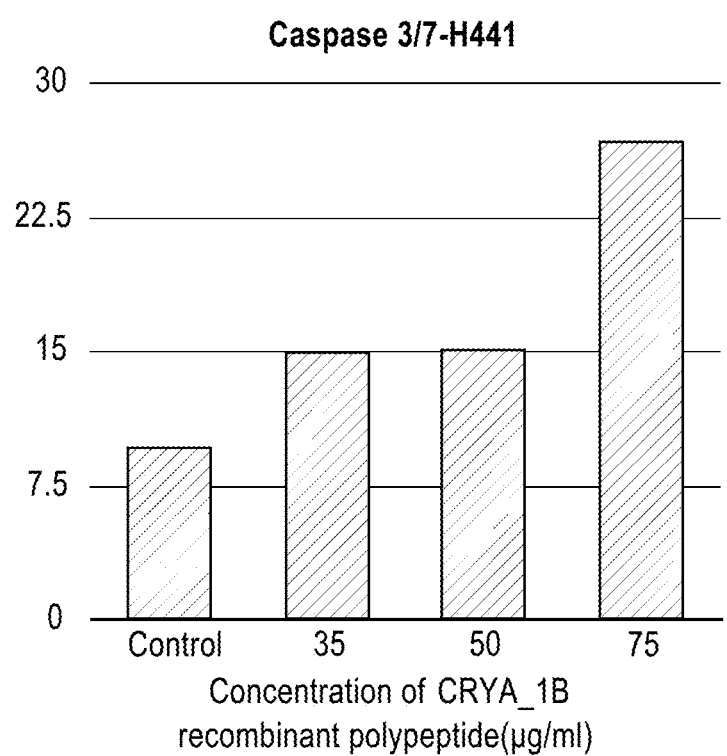
FIG. 15A shows a bar graph quantifying the percentage of cells that express Caspase 3/7 following treatment of H441 human lung cancer cell lines (HTB-174, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50 and 75 g/ml and the H441 cells were incubated for 2 hours and 45 minutes at 37° C. The H441 cells were determined by FACSCalibur (BD Biosciences) flow cytometry using Caspase 3/7 (Invitrogen) assay.
Figure 16A:
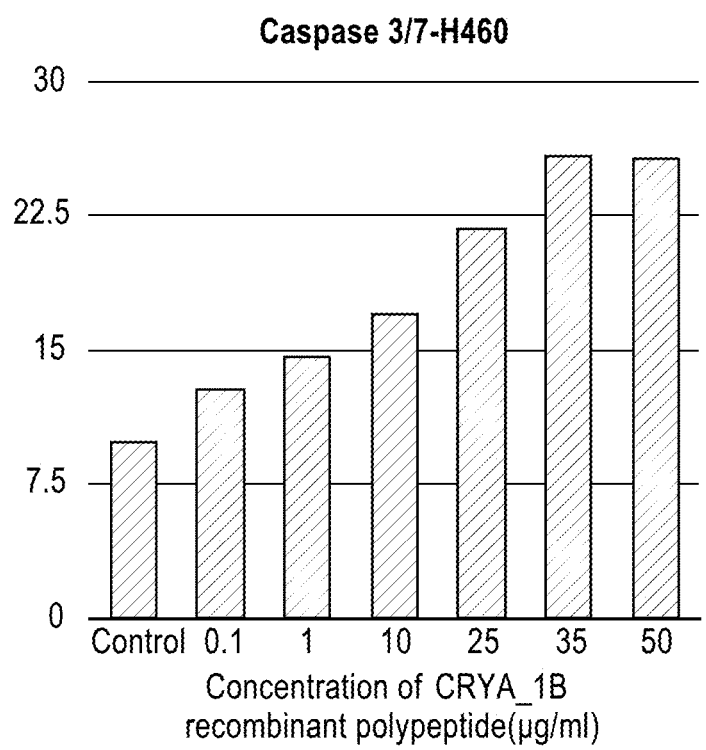
FIG. 16A shows a bar graph quantifying the percentage of cells that express Caspase 3/7 following treatment of H460 human lung cancer cell lines (HTB-177, ATCC) with various concentrations of CRYA_1B recombinant polypeptide (SEQ ID NO: 9). The stock CRYA_1B recombinant polypeptide (SEQ ID NO: 9) was diluted to the final concentration of 0.1, 1, 10, 25, 35 and 50 µg/ml and the H460 cells were incubated for 2 hours and 45 minutes at 37° C. The H460 cells were determined by FACSCalibur (BD Biosciences) flow cytometry using Caspase 3/7 (Invitrogen) assay.
Figure 17A:
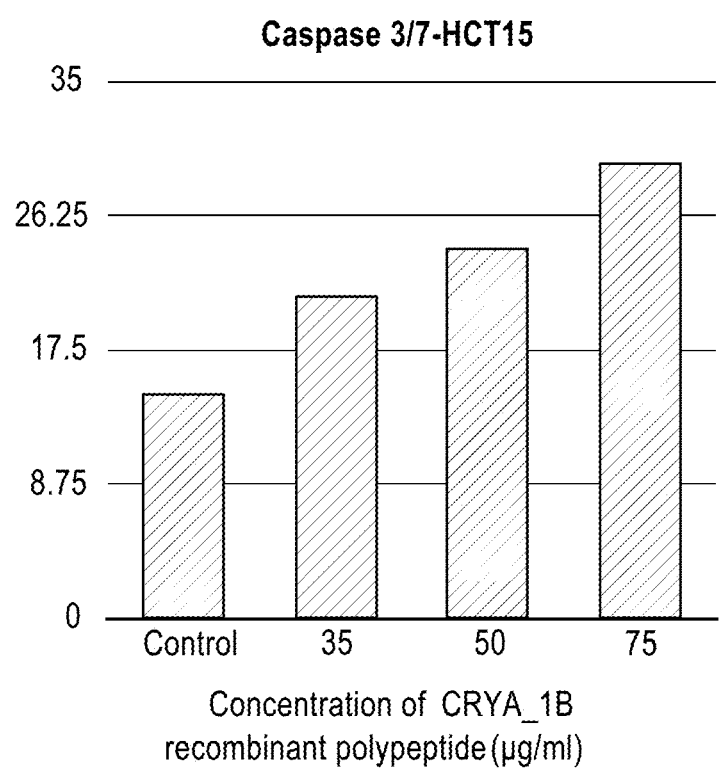
FIG. 17A shows a bar graph quantifying the percentage of cells that express Caspase 3/7 following treatment of HCT15 human colon cancer cell lines (CCL-225, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 µg/ml and the HCT15 cells were incubated for 2 hours and 30 minutes at 37° C. The HCT15 cells were determined by FACSCalibur (BD Biosciences) flow cytometry using Caspase 3/7 (Invitrogen) assay.
Figure 17B:
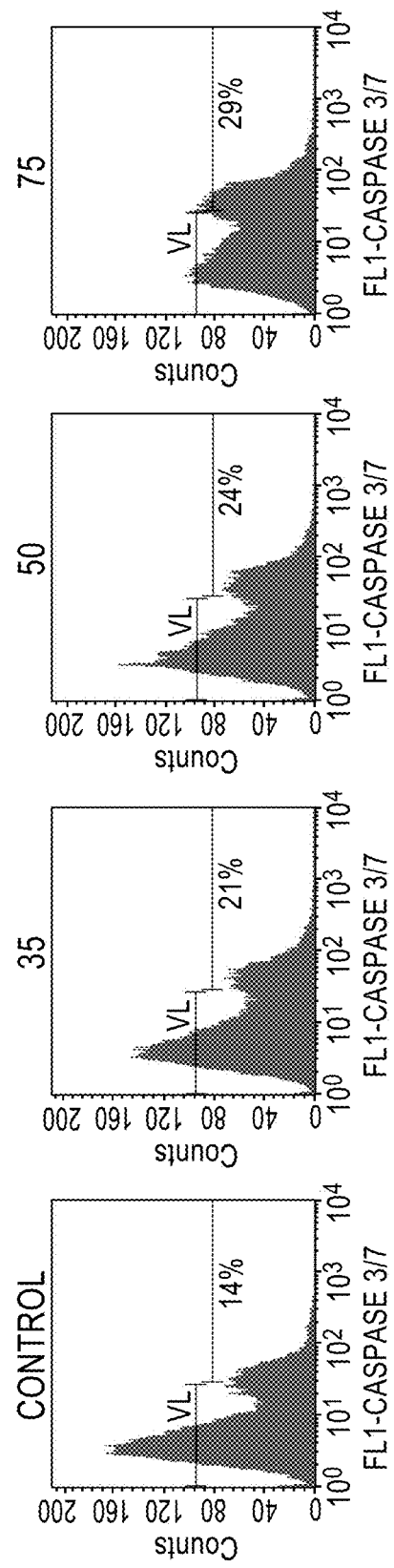
FIG. 17B shows the flow cytometry profiles used for quantification.
Figure 18A:
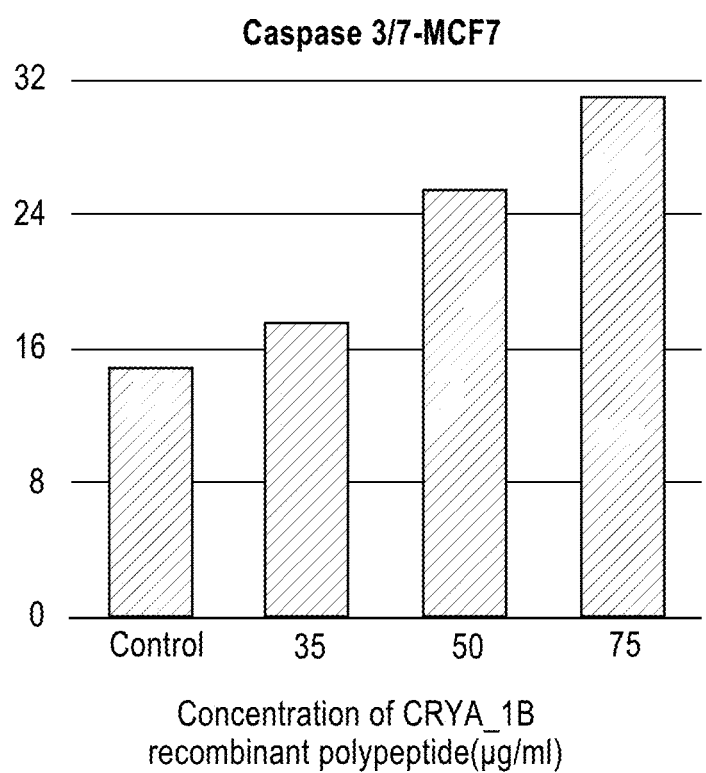
FIG. 18A shows a bar graph quantifying the percentage of cells that express Caspase 3/7 following treatment of MCF7 human breast cancer cell lines (HTB-22, ATCC) with various concentrations of CRYA_1B recombinant polypeptide (SEQ ID NO: 9). The stock CRYA_1B recombinant polypeptide (SEQ ID NO: 9) was diluted to the final concentration of 35, 50, 75 g/ml and the MCF7 cells were incubated for 2 hours and 45 minutes at 37° C. The MCF7 cells were determined by FACSCalibur (BD Biosciences) flow cytometry using Caspase 3/7 (Invitrogen) assay.
Figure 18B:
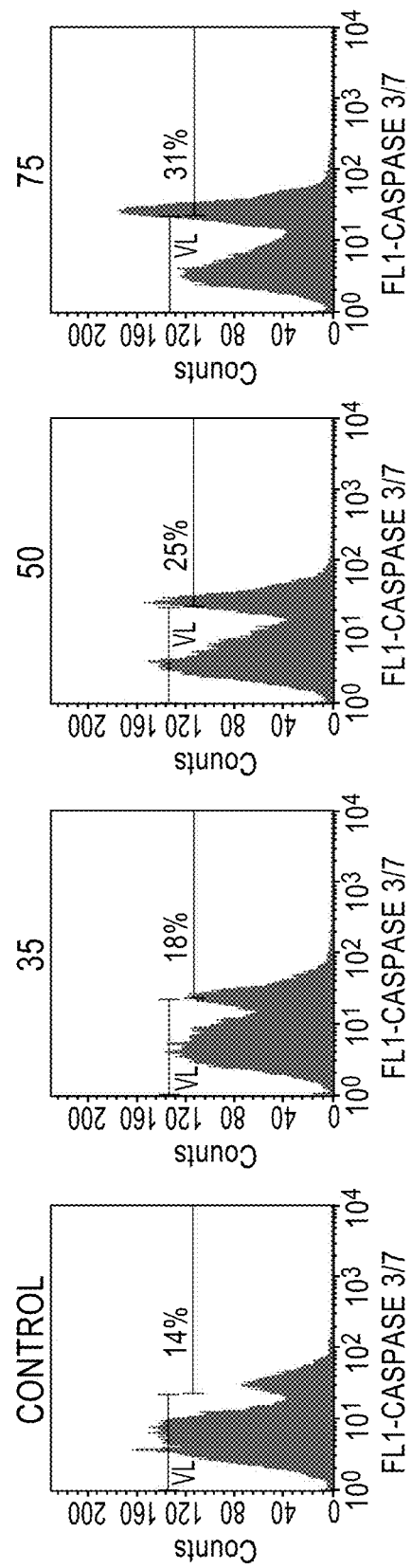
FIG. 18B shows the flow cytometry profiles used for quantification.

Plasmid_9 was transformed into the expression *Escherichia coli* strain BL21, and the ampicillin-resistant colonies were selected. The expected molecular weight for CRYA_1B recombinant polypeptide was 20 kDa (FIG. 2). A single colony from Luria-Betani (LB)-agar plate supplemented with 100 µg/ml ampicillin was selected. In this preparation, a 50 ml conical tube containing 3 ml of LB medium (10 g tryptone, 10 g NaCl and 5 g yeast extract per L) and 100 µg/ml of ampicillin was inoculated with a single colony and grown overnight in a shaking incubator set at 37° C. and 200 RPM. The culture was further expanded by adding 3 ml of the culture into a sterile 500 ml Erlenmeyer flask containing 100 ml of 2YT medium (16 g tryptone, 15 g yeast extract and 8 g NaCl per L) and 100 µg/ml of ampicillin and grown overnight in a shaking incubator set at 37° C. and 200 RPM. This resulted in a seed culture.

A 6 L bioreactor was used to further expand the seed culture. 4 L of 2YT medium containing 100 µg/ml of ampicillin was inoculated with 100 ml of seed culture grown overnight in a shaking incubator set at 37° C. and 200 RPM. In the bioreactor, cultures were incubated at 37° C., airflow and agitation of 2 SLPM (standard liners per minute) and 200 RPM. When the OD600 reached 0.65 to 0.75, protein overexpression was induced with 1.0 mM Isopropyl-β-D-thiogalactopyranoside (IPTG). The cells were allowed to grow for 7 to 8 hours and the agitation speed, temperature and air flow were set to 400 RPM, 28° C. and 4 SLPM, respectively. To control foaming, Polyglycol P-2000 antifoam was added as required. After 7 to 8 hours of induction, the cells were harvested by centrifugation at 8000 rpm for 15 minutes at 4° C. The cell pellets were frozen and stored at −80° C.

Purification of Recombinant Polypeptide CRYA_1B

In this preparation, the pellets, equivalent to 6 g of CRYA_1B recombinant polypeptide (SEQ ID NO: 9) was resuspended in 40 ml of Buffer A (50 mM Tris-HCl buffer) and disrupted by sonication on ice (28 cycles of 10-s pulses with 30-s intervals, 30% amplitude using an ultrasonic cell disruptor Misonix Ultrasonic Liquid Processors S-4000, USA) to obtain the total protein extract for solubility analysis. The total protein extract was centrifuged at 14,000 rpm for 45 min at 4° C. using a Sorvall RC5C Plus (USA) ultracentrifuge using a type SS-34 rotor. The supernatant was filtered through a 0.45 µm filter (Millipore) and loaded onto a Q-Sepharose anion exchange column equilibrated in the same buffer. Q-Sepharose was packed into a C 26/40 Column (GE Healthcare) to a bed height of 20 cm. A 40 mL volume of supernatant containing CRYA_1B recombinant polypeptide (SEQ ID NO: 9) was loaded onto the column using AKTA FPLC (GE Healthcare) at a flow rate of 5 ml/min. CRYA_1B recombinant polypeptide (SEQ ID NO: 9) was eluted by a concentration gradient by using an equilibrium buffer containing 50 mM Tris-HCl, NaCl buffer and collected in a single peak based on A280 absorbance for further application on the hydrophobic interaction column. The eluents collected were analyzed by 15% SDS-polyacrylamide gel electrophoresis.

Hydrophobic Interaction Chromatography

After ion exchange chromatography, the eluted CRYA_1B recombinant polypeptide (SEQ ID NO: 9) was pooled together, concentrated by Amicon Ultra 15 ml Centrifugal Filter (Merck), and subsequently added to the saturated ammonium sulphate buffer (50 mM Tris-HCl, 3.8 M ammonium sulphate, 1 mM DTT and 1 mM EDTA), resulting in a final concentration of 1.2 M ammonium sulphate. The concentrated product with adding ammonium sulphate was filtered using a 0.45 μm syringe filter (Millipore) and loaded to Hydrophobic Interaction Chromatography column (C 10/20 column, Ge Healthcare) at a flow rate of 2 ml/min. Source 15PHE (GE Healthcare) was packed into C 10/20 column (GE Healthcare) to a bed height of 10 cm and pre-equilibrated with buffer A (50 mM Tris-HCl, 1.2 M ammonium sulphate, 10% glycerol, 1 mM DTT and 1 mM EDTA). The column was washed with buffer A and the protein elution using buffer B (50 mM Tris-HCl, 10% glycerol, 1 mM DTT and 1 mM EDTA) was achieved with a linear gradient with decreasing ammonium sulphate and increasing glycerol. The eluted protein was analyzed by 15% SDS-PAGE. The fractions were further concentrated by Amicon Ultra 15 ml Centrifugal Filter (Merck).

Buffer Exchange Using Gel Filtration

The purified recombinant polypeptide was further exchanged into PBS buffer by using a Sephadex G-25 column. Sephadex G-25 was packed into a C 26/100 column (GE Healthcare) to a bed height of 85 cm and pre-equilibrated with PBS buffer at a flow rate of 1 ml/min. The concentrated protein was eluted after 2.5 hours and analyzed by 15% SDS-PAGE. The resulting eluates were then concentrated by Amicon Ultra 15 ml Centrifugal Filter (Merck).

Example 2: Methods of Inducing or Enhancing an Immune Response

Cancer cell lines were treated with CRYA_1B recombinant polypeptide (SEQ ID NO: 9), CRYA_1B recombinant polypeptide was diluted to various concentrations and incubated with human cancer cell lines H441 (lung cancer, HTB-174, ATCC), H460 (lung cancer, HTB-177, ATCC), HCT15 (colon cancer, CCL-225, ATCC) and MCF7 (breast cancer, HTB-22, ATCC) all at 37° C. As of CRT, HSP70, HSP90, and Caspase 3/7 assay, the recombinant polypeptide incubation time for H441 is 60 min, 1 hr 50 min, 1 hr 40 min, and 2 hr 45 min respectively, for H460 is 30 min, 1 hr 15 min, 1 hr 5 min, and 2 hr 30 min respectively, for HCT15 is 55 min, 1 hr 50 min, 1 hr 30 min, and 2 hr 30 min respectively, and for MCF7 is 1 hr 10 min, 1 hr 40 min, 1 hr 45 min, and 2 hr 45 min respectively. Flow cytometry was used to assess the cell surface expression of calreticulin (CRT) (FIGS. 3-6), HSP70 (FIGS. 7-10), HSP90 (FIGS. 11-14) and Caspase 3/7 (FIGS. 15-18) in cells treated with CRYA_1B recombinant polypeptide and in untreated control cells. This was performed using a FACSCalibur (BD Biosciences) using CRT mAb (Abcam), HSP70 mAb (Enzo Life Sciences), HSP90 mAb (Enzo Life Sciences) and Caspase 3/7 (Invitrogen assay), respectively.

Example 3: Treatment with Recombinant Polypeptide CRYA_1B Induces SAP Levels in Mice and CRP Levels in Human Cancers can undergo extensive genetic and phenotypic variations within tumours (intratumoural heterogeneity) but also between tumours (intertumoural heterogeneity). Recurrent tumour, often seeded from the covert subclones of primary tumour, is a leading cause of cancer mortality. Similarly, metastases, the lethal late stage of cancer progression, inherit multiple genetically distinct early subclones from primary tumour. However, the metastatic tumours exhibits less intratumoural heterogeneity than that of primary tumour. The main cause of intertumoural heterogeneity originates from the intratumoural heterogeneity of primary tumour. Because of cancer immunoediting process, tumours can develop an attenuated immunogenicity and create an immunosuppressive microenvironment to prevent tumour's eradication by host immune system.

Figure 19:
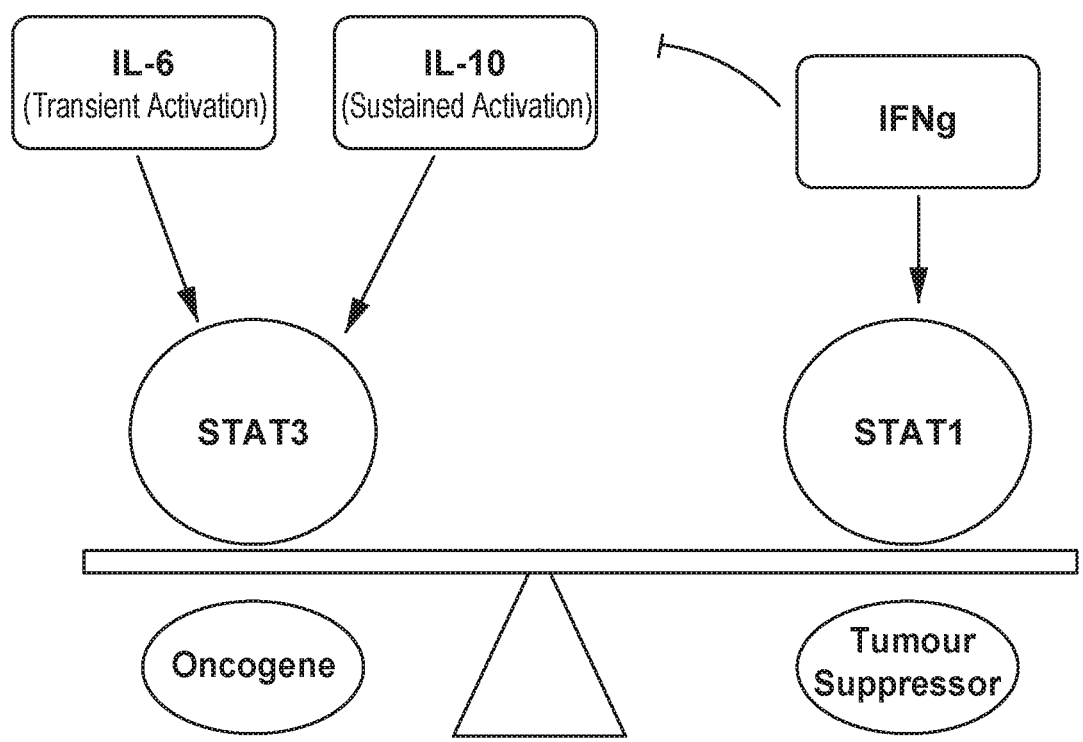
FIG. 19 shows a schematic diagram of the effects of IL-6, IL-10 and Interferon gamma (IFNg) on STAT3 and STAT1. Human STAT1 has a half-life of ~24 hours. Murine STAT1 has a half-life of ~7.8 hours. The balance of STAT3 and STAT1 affects oncogenesis and tumor suppression, respectively.
Figure 20:
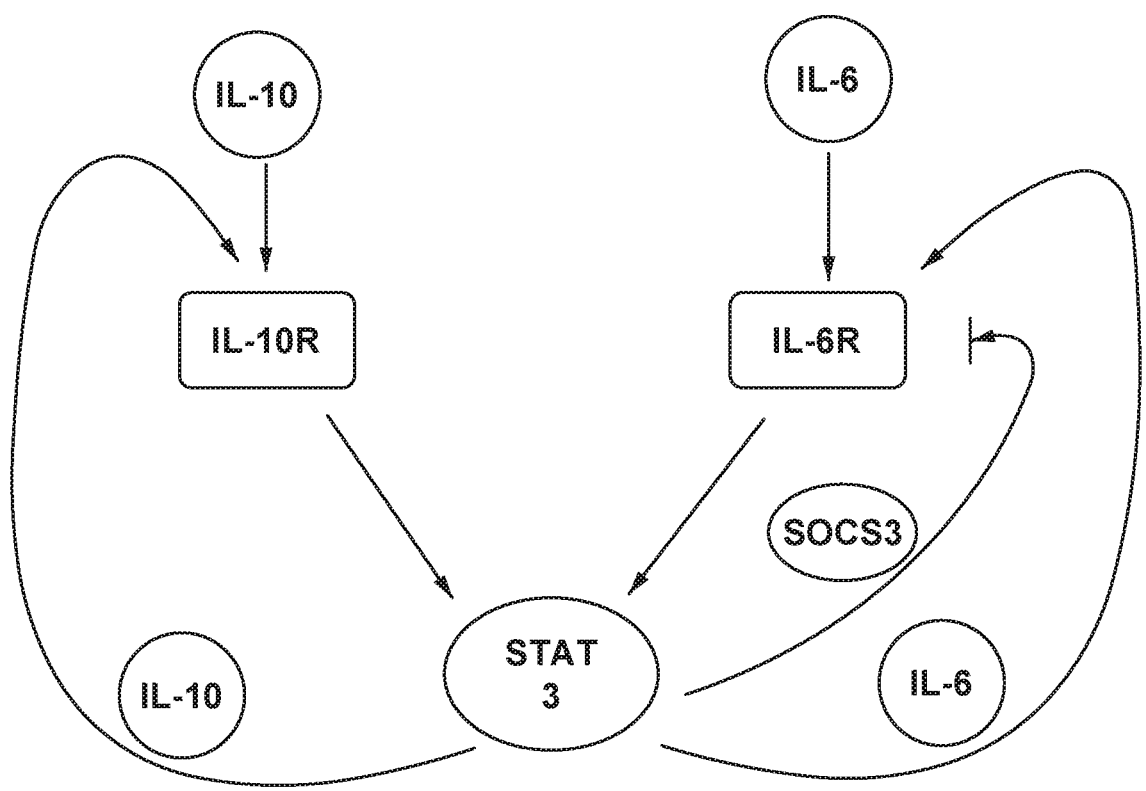
FIG. 20 shows a schematic diagram of the IL-10 and IL-6 pathways. IL-10 sustains STAT3 activation. IL-6 transiently activates STAT3 with self-inhibiting SOCS3.

Cancer cells have the ability to conceal tumor danger signals, causing chronic inflammation of the tumor microenvironment with Th2 cells which release (Interleukin (IL)-4 and IL-10) leading to a higher serum IL-10 level in cancer subjects in comparison to normal healthy subjects. IL-10 is an anti-inflammatory cytokine that induces STAT3 signaling (FIGS. 19 and 20) and inhibits DC activation and functionality. IL-10 leads to a tumor microenvironment made of myeloid-derived suppressor cells (MDSC), tumour-associated macrophages (TAM) and regulatory T cells (Treg), resulting in tumour escape. This ultimately causes reduced adaptive immune activation. By contrast, bacterial and viral infections expose danger signals, which leads to acute inflammation with Th1 cells which release L-12 and IFNg (FIG. 19) immune-stimulatory cytokines into the microenvironment, resulting in adaptive immune activation.

Calreticulin (CRT) is a danger signal that recruits dendritic cells (DC) to ingest tumours and pathogens. HSP70 and HSP90 are danger signals that induce maturation or activation of dendritic cells, which in turn produce L-12 and IL-6. Dendritic cells can then present antigens in the context of MHC-I and MHC-II to T cells in lymph nodes. Activated DC can produce L-12 which is a Th1 cytokine that promotes the activation of T cells, which in turn produces IL-2 and IFNg. The acute transient high IL-6 from activated-DC causes acute inflammation resulting in fever, which facilitates the immune T-cell activation. Chronic expression of IL-6 causes chronic inflammation, which impedes immune activation.

Serum amyloid P component (SAP) is the mouse homolog of human C-Reactive Protein (CRP). CRP and SAP are biomarkers of IL6, as IL6 induces production of SAP and CRP. MC38 tumour-bearing mice were injected with recombinant polypeptide CRYA_1B (SEQ ID NO: 9) at varying doses. Blood was sampled 20 hrs after treatment (n=2 mice for each dose). SAP was determined by Luminex assays. Treatment with recombinant polypeptide CRYA_1B (SEQ ID NO: 9) (mg/kg) correlates linearly with the SAP level (mg/L). Table 4 and FIG. 21 shows the results of this experiment. The linear correlation result shows that recombinant polypeptide CRYA_1B (SEQ ID NO: 9) induces SAP in mice. This can be used as a predictor of the effect of recombinant polypeptide CRYA_1B (SEQ ID NO:9) on CRP levels in humans or SAP levels in mice. Furthermore, as CRP/SAP is a proxy for IL-6, this result suggests that recombinant polypeptide CRYA_1B (SEQ ID NO: 9) induces production of IL-6, likely through the activation of dendritic cells.

TABLE 4

Recombinant polypeptide CRYA_1B (SEQ ID NO: 9) induces CRP in human and SAP in mice

| Recombinant polypeptide CRYA_1B (mg/kg) | CRP or SAP (mg/L) |
|---|---|
| 12 | 123 |
| 12.5 | 128 |
| 13 | 133 |
| 13.5 | 138 |
| 14 | 143 |
| 14.5 | 148 |
| 15 | 153 |
| 16 | 163 |
| 17 | 173 |
| 18 | 183 |
| 19 | 194 |
| 19.5 | 200 |
| 20 | 205 |
| 20.5 | 210 |
| 21 | 216 |
| 21.4 | 220 |

Figure 22:
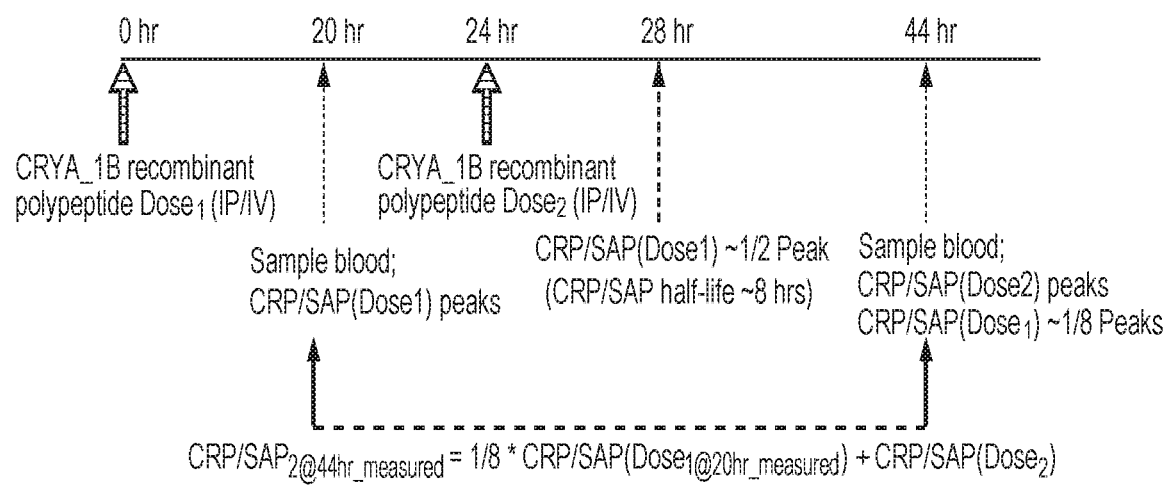
FIG. 22 shows a schematic timeline of a treatment regimen using CRYA_1B recombinant polypeptide (SEQ ID NO:9) and the predicted values of CRP/SAP. A first dose of CRYA_1B recombinant polypeptide (SEQ ID NO:9) is injected either intraperitoneally or intravenously at time 0. A second dose is injected 24 hours later. The CRP/SAP levels in the blood at 44 hrs after the initial injection is calculated with the following formula $CRP/SAP_{2@44\ hr\_measured}$=1/8*$CRP/SAP(Dose_{1@20\ hr\_measured})$+$CRP/SAP(Dose_2)$.

After treatment of mouse or human with recombinant polypeptide CRYA_1B (SEQ ID NO: 9), the SAP and CRP levels peak at about 20 hours after the injection, respectively. A schematic timeline is shown in FIG. 22. The CRP/SAP levels are reduced to half of the peak amount at about 28 hours after the initial injection. A second dose of recombinant polypeptide CRYA_1B (SEQ ID NO: 9) is injected at 24 hours after the initial dose. This second dose will cause CRP or SAP levels to peak at 44 hours after the first injection. Therefore accounting for the half-life of CRP or SAP induced by the initial dose of the recombinant polypeptide, the total CRP or SAP levels at hour 44 can be calculated using the following formula: $CRP/SAP_{2@44\ hr\_measured} = 1/8 * CRP/SAP(Dose_{1@20\ hr\_measured}) + CRP/SAP(Dose_2)$

Example 4: The Effects of Interferon Gamma on Serum IL-10

The levels of Serum IL-10 in cancer patients is increased in comparison to normal healthy subjects. For example, the serum IL-10 in human patients with lung cancer stage III-IV and a normal healthy subject is 17.7 pg/mL and 9.2 pg/mL, respectively (IL-10 ratio of 1.924). The serum IL-10 in murine C57BL/6 with B16F10 melanoma and a control healthy mouse is 95 pg/mL and 50 pg/mL, respectively (IL-10 ratio of 1.9). The serum IgG in murine C57BL/6 with B16F10 melanoma and a control healthy mouse is 1200 and 650 MFI, respectively (IgG ratio of 1.846). The serum IL-10 in murine C57BL/6 with MC38 (colon cancer) and a control healthy mouse is 70 pg/mL and 50 pg/mL respectively (IL-10 ratio of 1.4). The serum IL-10 in murine C57BL/6 with E0771 (breast cancer) and a control healthy mouse is 70 pg/mL and 50 pg/mL respectively (IL-10 ratio of 1.4).

Figure 23:
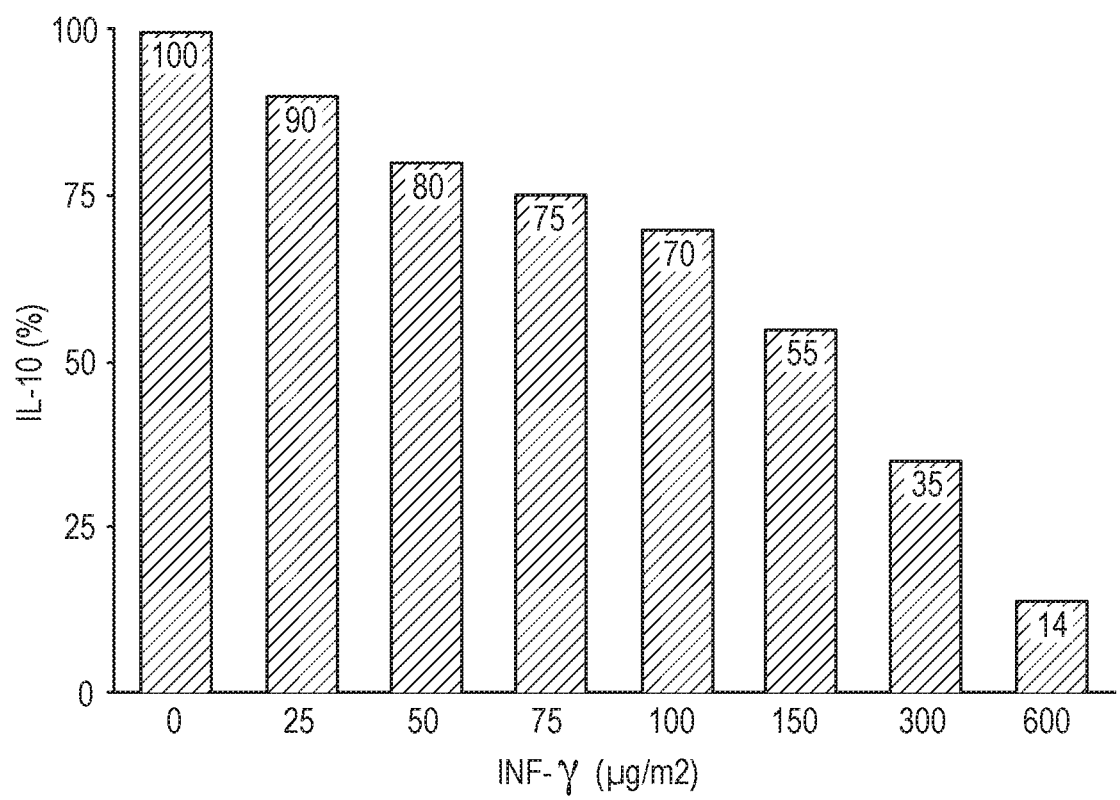
FIG. 23 shows a bar graph of the measured % serum IL-10 versus the dose of IFN gamma. An intravenous injection of IFNg at varying doses was given to B16F10 tumor bearing mice (n=2 for each IFNg dose). Blood was sampled 3.5 hours after IFNg injection and serum IL-10 was determined by Luminex assays.

As IFNg inhibits the levels of Serum IL-10, intravenous injections of IFNg were administered to B16F10 tumor bearing mice to determine the effects on serum IL-10. Blood was sampled 3.5 hours after IFNg injection and serum IL-10 was determined by Luminex assays. Table 5 and FIG. 23 show that an increased dosage of IFNg results in decreased serum IL-10 levels in mice.

TABLE 5

Percent Serum IL-10 Levels after following injection of IFNg

| In vivo IFNg dose (µg/m²) | Serum IL-10 Levels remaining |
|---|---|
| 600 | 14% |
| 300 | 35% |
| 150 | 55% |
| 100 | 70% |
| 75 | 75% |
| 50 | 80% |
| 25 | 90% |
| 0 | 100% |

Example 5: MC38, E0771 and B16F10 In Vivo Tumor Challenge and Re-Challenge Methods and Dosage Regimen Methods.

Female 10-12 weeks old C57BL/6 mice (Charles River Laboratories, USA) were housed and maintained under pathogen-free conditions in accordance with the guidelines of the Association for Assessment and Accreditation of Laboratory Animal International Care.

The C57BL/6 mice were inoculated subcutaneously with $1 \times 10^6$ MC38/E0771/B16F10 cells in 100 µl PBS into the flank. Tumour volume was measured with a caliper and calculated using the formula (A×B2)/2 [A: the largest diameter; B: the smallest diameter of tumour]. When the tumour reached approximately 100 mm3, we began recombinant polypeptide and IFN gamma treatment via intraperitoneal injection. The mice were pre-characterised the initial (pre-therapy) average serum $IL-10_i/IgG_i/IgE_i/IgA_i/IgM_i$ using control cohort (n=10 mice for each tumour model) bearing similar tumour size (~100 mm³). Because the total volume of blood in mice is low, it was not possible to sample blood on consecutive days for each mouse during the therapy. For each therapy cohort (n=10 mice for each tumour model), we assigned five mice for blood samplings in order to obtain average $SAP_{d0}$, a separate set of five mice to obtain average $SAP_{d1}$. The $IgG_{d3}/IgE_{d3}$ $IgG_{d7}/IgE_{d7}$ blood sampling was performed for each mouse. Consequently, the dose personalisation was performed as a group average instead of individually due to the constraint of available blood volume in mice.

Mouse Treatment Regimen.

One therapy treatment consists of 3-4 cycles. The treatment schedule (FIG. 24) and calculation of dosage regimen is shown below.

Cycle 1:

(Day 0): If serum $IL-10_i/IgG_i$>normal, select an IFNg dose for IP injection to normalise serum IL-10 ratio from Table 5. For MC38 and E0771 mice (IL-10 ratio=1.4×) (described in Example 4), select a 75-100 µg/m² (25-33 µg/kg) IFNg dose for IP injection. For B16F10 mice (IL-10 ratio=1.9×), select 150 µg/m² (50 µg/kg) IFNg dose. Wait 3-4 hrs after IFNg injection. Perform IP injection of recombinant polypeptide CRYA_1B (SEQ ID NO: 9) at 20 mg/kg (trial $Dose_{d0}$). Sample blood from host ~20 hrs after recombinant polypeptide CRYA_1B injection for $SAP_{d0}$ in order to determine the dose of recombinant polypeptide CRYA_1B for subsequent cycles of treatment.

(Day 1): Perform IP injection of recombinant polypeptide CRYA_1B (SEQ ID NO: 9) at 13.5 mg/kg (trial $Dose_{d1}$). Sample blood from host ~20 hrs after T-20DC injection for $SAP_{d1}$.

(Day 3): Sample blood from host for serum $IgG_{d3}/IgE_{d3}$

Cycle 2: (Day 4): If serum $IgG_{d3}$>normal, select an the IFNg dose for IP injection to normalise serum IL-10 ratio. Wait 3-4 hrs after IFNg injection. Adjust or personalise the next dose of recombinant polypeptide CRYA_1B using the following calculations and for IP Injection: Inject recombinant polypeptide CRYA_1B at $Dose_{d4}$, based on a) 200 mg/L<=$SAP^{optimal\_d}$<=220 mgL
b) 159 mg/L<=$SAP^{optimal\_d+1}$<=169 mg/L
c) y (SAP)=10.4x (Dose)−2.6
d) $SAP_{d+1}$=SAP($Dose_d$)/8+SAP($Dose_{d+1}$)

For example, if $SAP^{optimal\_d1}$=210, and $SAP^{optimal\_d2}$=164
Assume measured $SAP_{d0}$=190, $SAP_{d1}$=150 [From a) & b)=>Trial $Dose_{d0}$=20 and $Dose_{d1}$=13.5 too low for host]
Adjust y (SAP)=10.4x (Dose)−2.6=>9.81x−6.2 (Personalised dose)
=>190=20a+b
=>150-190/8=13.5a+b
=>a=9.81, b=−6.2
For SAP (Optimal $Dose_{d4}$)=$SAP^{optimal\_d1}$=210=9.81x−6.2, then x=$Dose_{d4}$=22.04 mg/Kg (Personalised dose)
For $SAP_{d5}$=$SAP^{optimal\_d2}$=164=SAP(Optimal $Dose_{d4}$)/8+ SAP ($Dose_{d5}$)=210/8+SAP ($Dose_{d5}$)
SAP ($Dose_{d5}$)=137.75=9.81x−6.2
=>x=$Dose_{d5}$=14.67 mg/kg (Personalised dose)

(Day 5): Perform IP injection of recombinant polypeptide CRYA_1B at $Dose_{d5}$ [$Dose_{d4}$-$Dose_{d5}$: 24 hrs apart]

(Day 7): Sample blood from host for serum $IgG_{d7}/IgE_{d7}$

Cycle 3. (Day 8): If serum $IgG_{d7}$>normal, Select the IFNg dose for IP injection to normalise serum IL-10. Wait 3-4 hrs after IFNg injection. IP Inject recombinant polypeptide CRYA_1B at $Dose_{d8}$=$Dose_{d4}$ (Day 9): IP injection of recombinant polypeptide CRYA_1B at $Dose_{d9}$=$Dose_{d5}$ [$Dose_{d8}$-$Dose_{d9}$: 24 hrs apart]

(Day 11): Sample blood from host for serum $IgG_{d11}/IgE_{d11}$

Results.

MC38 is a chemical-induced Grade-III SMAD4-loss metastatic colorectal adenocarcinoma for the model of metastases, and E0771, a triple-negative cancer claudin-low self-renewal spontaneous mammary adenocarcinoma for the model of relapse. The hallmark of adaptive immunity to cancer is for long-lived neoantigen-specific T cells with immunologic memory to respond faster and robustly upon re-encountering the same neoantigen in order to prevent cancer relapses. For the proof of long-term adaptive immunity memory, we pooled together the complete-response (CR) mice from the tumour challenge experiments, and then rechallenged these CR mice with live tumour cells, mimicking the spontaneous tumour recurrence by externally forced live tumour cells injection, at the opposite site of primary tumour 6-month after the complete rejection of primary tumour. When there is no sign of tumour growth, it indicates the successful murine 6-month adaptive immunity corresponding to approximately 15-20 years in human. The MC38 has the phenotype of SMAD4-loss, which is associated with colon cancer patient's metastases and poor survival. MC38 tumour challenge experiments show that primary tumour variants began to grow aggressively after the initial spontaneous partial tumour regression and approximately 40% of mice would develop 1 or 2 locoregional metastases. For the CR mice after recombinant polypeptide CRYA_1B (SEQ ID NO: 9) treatment, the metastases would undergo complete regression first whereas the primary tumour would first undergo partial regression and then eventually complete regression. We hypothesize that 1) before recombinant polypeptide CRYA_1B treatment, the preexisting T-cell's immunoselection against dominant neoantigen caused the initial spontaneous partial regression of primary tumour and the persistent immune pressure eventually led to the natural selection of dominant neoantigen-loss and/or MHC-I-deficient tumour variants; 2) primary tumour variants then suddenly grew aggressively and the locoregional metastases developed (immune escape); 3) after recombinant polypeptide CRYA_1B treatment, the drug-induced neoantigens were predominantly from metastases due to higher drug concentration coverage over smaller metastases compared to larger primary tumour variants; 4) the metastases underwent complete regression by multiple metastases-only subdominant neoantigens and putatively one shared subdominant neoantigen while the primary tumour variants were in parallel undergoing limited partial regression by one shared subdominant neoantigen; 5) after the CR of metastases, the subsequent doses of recombinant polypeptide CRYA_1B induced the multiple primary-only subdominant neoantigens in addition to the shared subdominant neoantigen; 6) the primary tumour variants eventually underwent complete regression. In contrast, if the DC-mediated neoantigen-based vaccines utilise only immunodominant neoantigen, screened ex vivo from patient's TILs or peripheral blood mononuclear cells (PBMCs), without incorporating subdominant neoantigens, then it would be impossible to completely eradicate metastases and primary tumour due to the escapes of tumour variants.

Figure 25A:
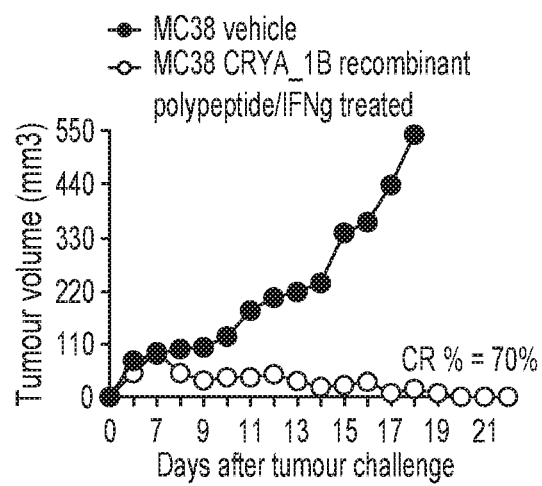
FIG. 25A-25D shows a series of line graphs depicting tumor volume in MC38 and E0771 tumor mice after treatment with the recombinant peptide and IFNg.
Figure 25B:
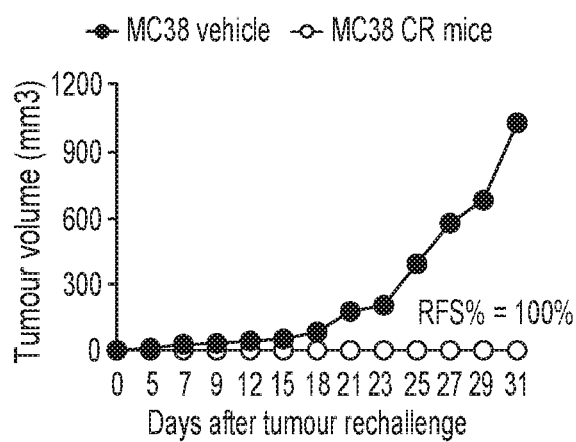
Figure 25C:
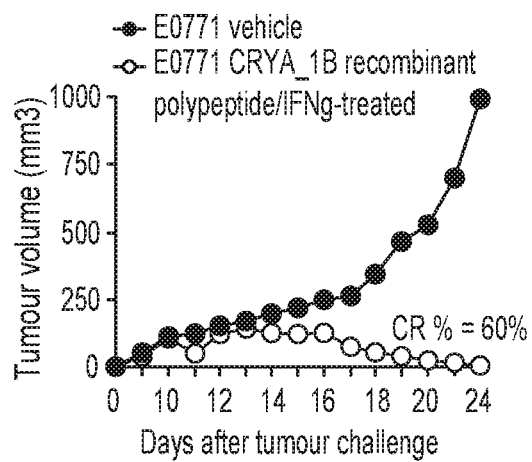
Figure 25D:
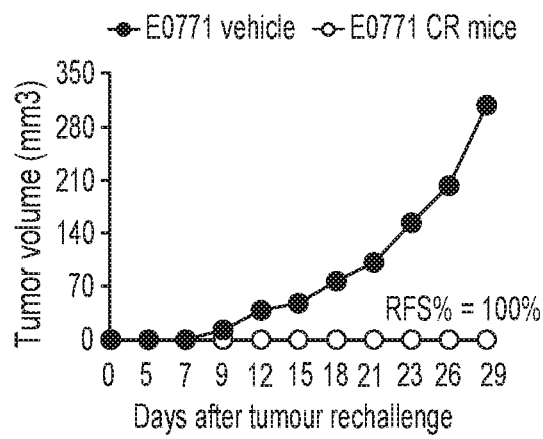
Figure 26A:
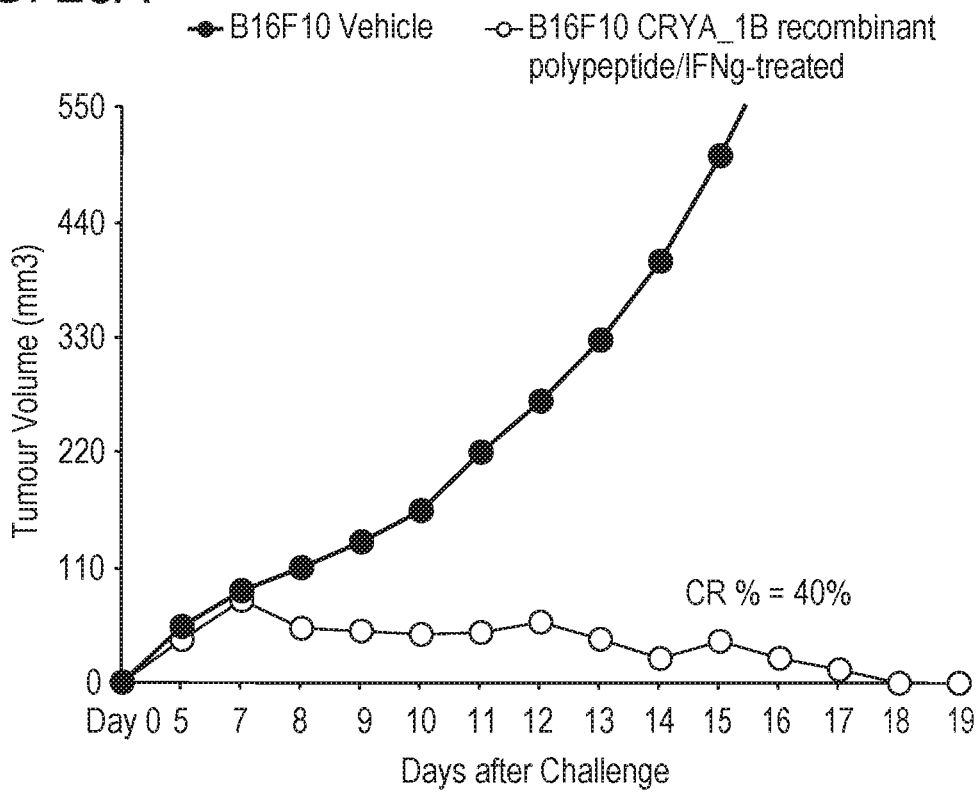
FIG. 26A-26B B1610 tumour challenge and rechallenge models in B6 mice.
Figure 26B:
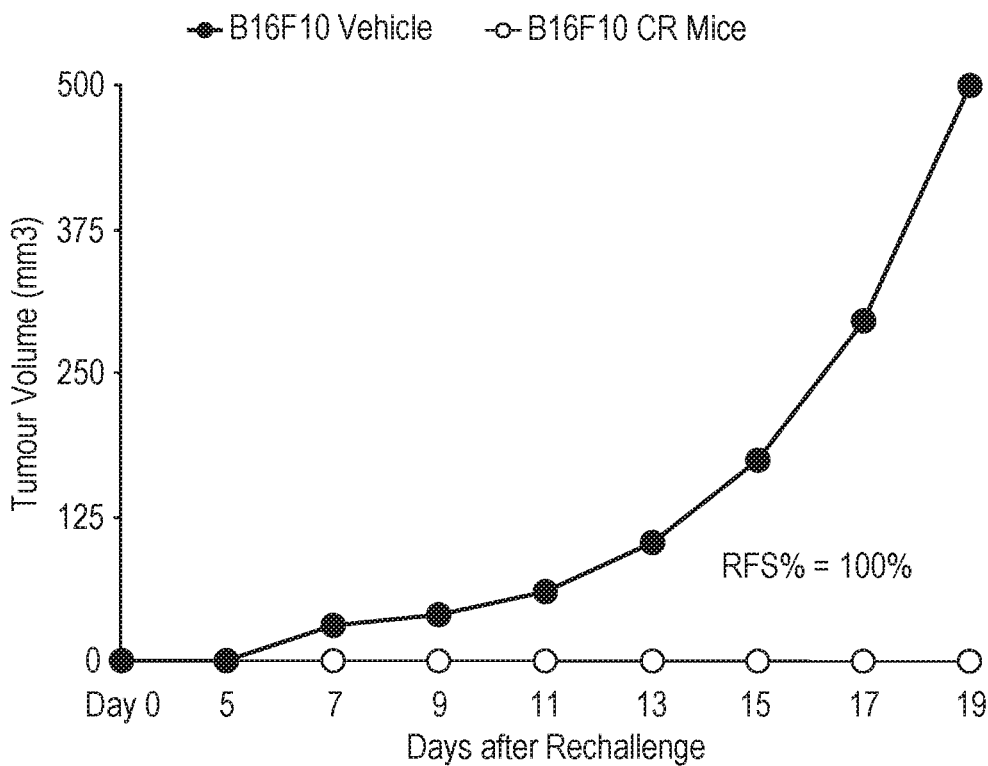

The overall CR rate of MC38 tumour challenge model was 70% after recombinant polypeptide CRYA_1B treatment and the relapse-free-survival rate for CR mice was 100% with long-term immunity without tumour recurrence after tumour rechallenge (FIGS. 25A and 25B). The triple-negative breast cancer, with extensive intratumoural heterogeneity, E0771 has a claudin-low tumour phenotype with the characteristic of enriched tumour-initiating (stem cell-like) CD44+CD24-/low cells especially after drug treatments for recurrence in human breast cancer patients. In light of E0771's stem-cell like tumour-initiating ability, we used it for the model of spontaneous tumour relapse. After recombinant polypeptide CRYA_1B treatments, we achieved the CR rate of 60% in E0771 tumour challenge model (FIG. 25C). We observed for 6 months and there was no sign of spontaneous E0771 tumour recurrence after CR. We hypothesised that recombinant polypeptide CRYA_1B simultaneously induced E0771-derived dominant neoantigen and multiple subdominant neoantigens, including those of cancer stem cell subclones, the neoantigen's multiplicity of which prevented E0771 from spontaneous relapse. Moreover, we rechallenged the CR mice with live E0771 tumour cells as externally forced tumour relapse, and there was no sign of tumour growth after rechallenge, indicating a successful long-lived adaptive immunity memory (FIG. 25D). Interestingly, we observed that there are two distinct tumour regression patterns after recombinant polypeptide CRYA_1B treatment for both MC38 and E0771 tumour models, one with continuous tumour regression until CR (FIG. 25A) whereas the other with temporary tumour flare and then later tumour regression until CR (FIG. 25C). The identical tumor challenge and tumor rechallenge experiments were carried out with B16F10 murine melanoma model. The overall CR rate of B16F10 tumour challenge model was 40% after treatment regimen and the relapse-free-survival rate for CR mice was 100% with long-term immunity without tumour recurrence after tumour rechallenge (FIGS. 26A and 26B). We hypothesize that after immunotherapy the tumour flare may occur, since the priming of immune system is complex and can be delayed while the tumour may transiently grow and/or substantial immune cells may transiently infiltrate tumour, resulting in an increase of tumour size during this period.

Additionally, recombinant polypeptide CRYA_1B (SEQ ID NO: 9) was administered daily in healthy immunocompetent B6 mice (n=7) at 1.6-fold clinical dose for seven consecutive days, with drug serum peak concentration at ~800 jag/ml, showed no significant changes in behaviour, body weight, food intake and key serum chemistry parameters at the end of experiment except the noticeable drop in body weight and food consumption after the first dose, yet usually recovered afterwards in 2-3 days without much influences by subsequent doses after the first dose.

In vitro toxicity was also investigated, by measuring Caspase 3/7, for normal human PBMCs (three healthy donors), made of innate and adaptive immune cells. Our results showed that the PBMCs viability was not significantly decreased even at 800 μg/mL injection of recombinant polypeptide CRYA_1B (SEQ ID NO: 9) (FIG. 27) which corroborated the in vivo safety profile without adverse events at comparable drug serum peak concentration. Together, this indicates that recombinant polypeptide CRYA_1B (SEQ ID NO: 9) potently activates long-term adaptive immunity devoid of cancer relapses and noticeable adverse events.

Discussion Despite the clinical success of checkpoint-blockading cancer immunotherapy for solid tumours such as anti-PD-1 therapy, there were only limited subset of patients with PD-L1+ tumour phenotype responding to anti-PD-1 therapy and very significant numbers of responding patients were subject to recurrence (mean time to relapse: 624 days) largely due to the natural selection of neoantigenloss and/or MHC-I-deficient tumour variants resulting from the immune pressure of repeated immunotherapy treatments. For better therapeutic efficacy and wider patient coverage without tumour phenotype restriction, the personalised DC-mediated neoantigen-based vaccines such as ex vivo DC vaccine, long-peptide vaccine, RNA vaccine and DNA vaccine invoked the de novo polyclonal T-cell immune responses with encouraging results. Although the polyclonal T cells can mitigate the risk of tumour outgrowth from the neoantigen-loss variants, the total loss of MHC-I presentation resulting from β2-microglobulin deficiency still remains as an effective tumour escape mechanism. Moreover, the ex vivo in silico neoantigen prediction accuracy challenge from patient's resectable tumour samples, problematic for inoperable tumours, the time-consuming (about 3-5 months) and costly GMP manufacturing are still the daunting issues to be resolved. In contrast, the intratumoural oncolytic virus (OV) therapy, an antigen-agnostic vaccine without ex vivo neoantigen prediction, uses the replication-competent adapted virus to selectively infect, multiply and lyse tumour cells via necroptosis, a programmed necrosis, which causes the permeability of cell membrane and the release of the tumor antigens and DAMPs for immunogenic cell death via endogenous DCs. Nevertheless, the systemic intravenous infusion of OV is required for the effective treatment of distant metastatic tumours; however, such systemic infusion will cause OV to be rapidly diluted in the circulation, neutralised by serum factors and sequestered in the liver and spleen. Consequently, the IV infusion of OV will require substantially higher dose, subject to manufacturing technology capability, by more than two orders of magnitude in order to achieve similar efficacy as that of intratumoural injection except with a potential dose-limiting Grade 4 toxicity. Furthermore, a biosafety regulatory approval is required for each clinical grade OV and the manufacturing technology capability for the required high clinical IV dose is still a challenge. In contrast, recombinant polypeptide CRYA_1B is a recombinant protein using the standard biologic manufacturing process. Moreover, recombinant polypeptide CRYA_1B can systemically induce multiple personalised in situ neoantigens to mitigate the escape of neoantigen-loss variants, synergistically activate CD4+ T cells, via HSP70/HSP90-peptide, and NK cells, via CD4+ helper's interleukin-2 priming for effective recognition of HSP70-expressing tumour cells, to eradicate MHC-I-deficient (NK cells susceptible) variants, and potently trigger CD70-CD27 ligation for reduced PD-1 expression on T cells to minimise PD-1/PD-L1-mediated immune peripheral tolerance. Thus, in light of attenuated immunogenicity such as neoantigen-loss, MHC-I-deficient variants and PD-1/PD-L1-mediated immune tolerance, and the immunosuppressive tumour microenvironment constituents such as myeloid-derived suppressor cells, tumour-associated macrophages and regulatory T cells, we chose to focus on how to reprogram the immunosuppressive tumour microenvironment for better DC activation in the first place. At this writing, we had screened, identified and verified an adjuvant synergistic with recombinant polypeptide CRYA_1B for reshaping tumour microenvironment, resulting in an increase of CR for both MC38 and E0771 colorectal and breast syngeneic tumour models respectively in immunocompetent mice. Together, the first-in-class recombinant α-crystallin recombinant polypeptide CRYA_1B showed the potent, systemic, real-time and in situ induction of pre-apoptotic personalised tumour-derived CRT-peptide, HSP70-peptide and HSP90-peptide, irrespective of solid-tumour cancer types and tumour phenotypes, elicited anti-tumour long-term immunity with T-cell polyclonal diversity to prevent cancer relapses, and also demonstrated minimal toxicity and adverse events to normal cells and hosts respectively.

Example 6. Use of Recombinant Polypeptide CRYA_1B (SEQ ID NO: 9) for Use in Treatment of Human Cancer The half-life of recombinant polypeptide CRYA_1B (SEQ ID NO: 9) is about 30 minutes in mice, whereas the half-life in human is about 180 min. Therefore, daily IP injection were administered twice (about 30 min. apart) in mice due to the shortened half-life (in Example 5). For humans, daily IV injection is administered once due to longer half-life.

Human Recombinant Polypeptide CRYA_1B (SEQ ID NO: 9) and Interferon Gamma Treatment Regimen.

Figure 28:
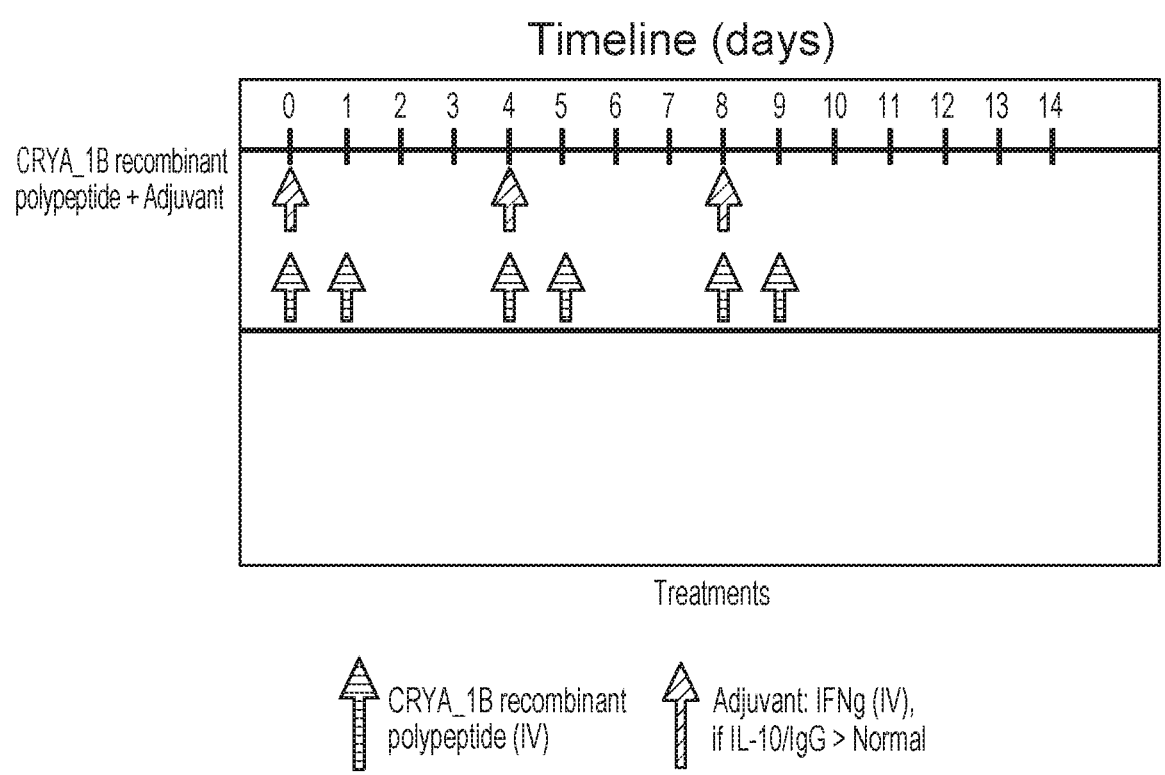
FIG. 28 shows a schematic diagram of a human dosage regimen for CRYA_1B recombinant polypeptide (SEQ ID NO: 9). Blue arrows indicated the timing of the intravenous or intraperitoneal injection of the recombinant polypeptide. Orange arrows indicate the timing of the intraperitoneal or intravenous injection of IFNg injection. Cycle 1 begins on Day 0. Cycle 2 begins on day 4. Cycle 3 begins on day 8. Optionally Cycle 4 begins on Day 12.

A schematic diagram of the human dosage treatment regimen is shown in FIG. 28. One therapy treatment consists of 3-4 cycles.

(Day −10/−14):—Sample blood from patients for serum IL-10i/IgGi/IgEi/IgAi/IgMi (Day −x: subject to IL-10 off-site turnaround; IgG/IgE/IgA/IgM: short on-site turnaround)

Cycle 1.

(Day 0): If serum IL-10i/IgGi>normal, select the IFNg dose for IV injection to normalise serum IL-10 ratio from Table 5. For example, for late-stage lung cancer patients (IL-10 ratio is ~1.924-2.28)(described in Example 4), select 150-200 μg/m² IFNg dose. Wait 3-4 hrs after IFNg injection. IV injection of recombinant polypeptide CRYA_1B (SEQ ID NO: 9) at 20 mg/kg (trial Dose$_{d0}$). Sample blood from host ~20 hrs after recombinant polypeptide CRYA_1B (SEQ ID NO: 9) injection for CRP$_{d0}$.

(Day 1): IP injection of recombinant polypeptide CRYA_1B (SEQ ID NO: 9) at 13.5 mg/Kg (trial Dose$_{d1}$)

[Dose$_{d0}$-Dose$_{d1}$: 24 hrs apart]. Sample blood from host ~20 hrs after recombinant polypeptide CRYA_1B (SEQ ID NO: 9) injection for CRP$_{d1}$.

(Day 3): Sample blood from host for serum IgG$_{d3}$/IgE$_{d3}$

Cycle 2.

(Day 4): If serum IgG$_{d3}$>normal, select the IFNg dose for IV injection to normalise serum IL-10 ratio from Table 5. Wait 3-4 hrs after IFNg injection. Adjust or Personalise the IV injection of recombinant polypeptide CRYA_1B (SEQ ID NO: 9) at Dose$_{d4}$, based on the following calculations:

200 mg/L<=CRP$^{optimal\_d}$<=220 mgL        a)

159 mg/L<=CRP$^{optimal\_d+1}$<=169 mg/L        b)

y (CRP)=10.4×(Dose)−2.6        c)

CRP$_{d+1}$=CRP(Dose$_d$)/8+CRP(Dose$_{d+1}$)        d)

For example, CRP$^{Optima\_d1}$=210 and CRP$^{optimal\_d2}$=164.
For example, if CRP$_{d0}$=224, CRP$_{d1}$=175 [Out of a) & b)=>Dose$_{d0}$=20 & Dose$_{d1}$=13.5 too high for host],
Adjust y (CRP)=10.4x (Dose)−2.6=>12x−15 (Personalised Dose)
=>224=20a+b
=>175-224/8=13.5a+b
=>a=12, b=−15
For CRP(Optimal Dose$_{d4}$)=CRP$^{optimal\_d1}$=210=12x−15, then x=Dose$_{d4}$=18.75 mg/kg (Personalised)
For CRP$_{d5}$=CRP$^{optimal\_d2}$=164=CRP(Optimal Dose$_{d4}$)/8+ CRP (Dose$_{d5}$)=210/8+CRP (Dose$_{d5}$)
=>CRP (Dose$_{d5}$)=137.75=12x−15
=>x=Dose$_{d5=12.73}$ mg/Kg (Personalised Dose)

(Day 5): IV injection of recombinant polypeptide CRYA_1B (SEQ ID NO: 9) at Dose$_{d5}$ [Dose$_{d4}$-Dose$_{d5}$: 24 hrs apart].

(Day 7):—Sample blood from host for serum IgG$_{d7}$/IgE$_{d7}$.

Cycle 3.

(Day 8): If serum IgG$_{d7}$>normal, select the IFNg dose for IV injection to normalise serum IL-10 ratio from Table 5. Wait 3-4 hrs after IFNg injection. IV Inject recombinant polypeptide CRYA_1B (SEQ ID NO: 9) at Dose$_{d8}$=Dose$_{d4}$.

(Day 9): IV injection of recombinant polypeptide CRYA_1B (SEQ ID NO: 9) at Dose$_{d9}$=Dose$_{d5}$ [Dose$_{d8}$-Dose$_{d9}$: 24 hrs apart].

(Day 11): Sample blood from host for serum IgG$_{d11}$/IgE$_{d11}$.

Cycle 4.

Perform cycle 4 if a complete response is not observed following Cycle 3. (Day 12):—If serum IgG$_{d11}$>normal, select the IFNg dose for IV injection to normalise serum IL-10 ratio. Wait 3-4 hrs after IFNg injection. IV Inject recombinant polypeptide CRYA_1B recombinant polypeptide CRYA_1B at Dose$_{d12}$=Dose$_{d4}$.

(Day 13): IV injection of recombinant polypeptide CRYA_1B (SEQ ID NO: 9) at Dose$_{d13}$=Dose$_{d5}$ [Dose$_{d12}$-Dose$_{d13}$: 24 hrs apart].

(Day 15): No treatment

If a complete response is not observed following Cycle 4, then pause treatment for 4 to 6 weeks and repeat the treatment cycles up to another four cycles (Second therapy). If a complete response is not observed after the second therapy, then the patient is deemed non-responsive to the therapy.

Example 7. Sample Calculation to Determine Recombinant Polypeptide CRYA_1B (SEQ ID NO: 9) Dose Determine the amount of recombinant polypeptide CRYA_1B (SEQ ID NO: 9) in Cycle 2 of Example 6 by performing the following calculations. Calculate the constants a and b in the following system of equations:

$$CRP_1 = a \times Amount_1 + b$$

$$CRP_2 - CRP_1/8 = a \times Amount_2 + b$$

wherein CRP$_1$ is the amount of C-Reactive Protein (CRP) in blood from the subject about 20 hours after the administration of the first amount of the recombinant polypeptide or the nucleic acid, CRP$_2$ is the amount of CRP in blood from the subject about 20 hours after the administration of the second amount of the recombinant polypeptide or the nucleic acid, Amount$_1$ is the first amount of the recombinant polypeptide or the nucleic acid and Amount$_2$ is the second amount of the recombinant polypeptide or the nucleic acid If Amount$_1$=20 mg/kg; Amount$_2$=13.5 mg/kg; CRP$_1$=224 mg/L; and CRP$_2$=175 mg/L, then,
224=20a+b
175−(224/8)=13.5a+b
Therefore, a=11.85 and b=−13

Calculate the third amount of recombinant polypeptide using the following equation: Amount$_3$, wherein $$Amount_3 = \frac{CRP^{Optimal1} - b}{a},$$

wherein CRP$^{Optimal1}$ is the intended optimal amount of CRP present in the blood of the subject after administration of the third amount of the recombinant polypeptide or the nucleic acid;

If CRP$^{Optimal1}$=210 mg/L, then Amount$_3$=(210-(−13))/11.85
Therefore, Amount$_3$=18.82 mg/kg Calculate the fourth amount of recombinant polypeptide using the following equation:

$$Amount_4 = \frac{(CRP^{Optimal2} - CRP^{Optimal1}/8) - b}{a};$$

If CRP$^{Optimal}$2=164 mg/L, then Amount$_4$=((164−(210/8))−(−13))/11.85
Therefore, Amount$_4$=12.72 mg/kg Example 8. Sample Calculation to Determine Recombinant Polypeptide CRYA_1B (SEQ ID NO: 9) Dose Determine the amount of recombinant polypeptide CRYA_1B (SEQ ID NO: 9) in Cycle 2 of Example 6 by performing the following calculations. Calculate the constants a and b in the following system of equations:

$$CRP_1 = a \times Amount_1 + b$$

$$CRP_2 - CRP_1/8 = a \times Amount_2 + b$$

wherein CRP$_1$ is the amount of C-Reactive Protein (CRP) in blood from the subject about 20 hours after the administration of the first amount of the recombinant polypeptide or the nucleic acid, CRP$_2$ is the amount of CRP in blood from the subject about 20 hours after the administration of the second amount of the recombinant polypeptide or the nucleic acid, Amount₁ is the first amount of the recombinant polypeptide or the nucleic acid and Amount₂ is the second amount of the recombinant polypeptide or the nucleic acid If $Amount_1=20$ mg/kg; $Amount_2=13.5$ mg/kg; $CRP_1=190$ mg/L; and $CRP_2=150$ mg/L, then, $190=20a+b$ $150-(224/8)=13.5a+b$ Therefore, $a=9.81$ and $b=-6.2$ Calculate the third amount of recombinant polypeptide using the following equation: $Amount_3$, wherein $$Amount_3 = \frac{CRP^{Optimal1} - b}{a},$$

wherein $CRP^{Optimal1}$ is the intended optimal amount of CRP present in the blood of the subject after administration of the third amount of the recombinant polypeptide or the nucleic acid;

If $CRP^{Optimal1}=210$ mg/L, then $Amount_3=(210-(-6.2))/9.81$

Therefore, $Amount_3=22.04$ mg/kg

Calculate the fourth amount of recombinant polypeptide using the following equation:

$$Amount_4 = \frac{(CRP^{Optimal2} - CRP^{Optimal1}/8) - b}{a}$$

If $CRP^{Optrima2}=164$ mg/L, then $Amount_4=((164-(210/8))-(-6.2))/9.81$

Therefore, $Amount_4=14.67$ mg/kg

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of treating cancer in a subject in need thereof comprising:
   a) administering a first amount of an agent that reduces IL-10 to the subject;
   b) administering a first amount of a recombinant polypeptide comprising an amino acid sequence having at least 99% sequence identity to the polypeptide of SEQ ID NO: 9 or a nucleic acid encoding the recombinant polypeptide comprising an amino acid sequence having at least 99% sequence identity to the polypeptide of SEQ ID NO: 9 to the subject between 2-24 hours after the administration of the first amount of the agent; and
   c) administering a second amount of the recombinant polypeptide or the nucleic acid to the subject at least 20 hours after the administration of the first amount of the recombinant polypeptide or the nucleic acid.

2. The method of claim 1, wherein
the first amount of the recombinant polypeptide or the nucleic acid of b) is administered to the subject at about 3-4 hours after the administration of the first amount of the agent; and
the second amount of the recombinant polypeptide or the nucleic acid of c) is administered to the subject at least 24 hours after the administration of the first amount of the recombinant polypeptide or the nucleic acid.

3. The method of claim 1, further comprising:
   d) administering a second amount of the agent to the subject at least 24 hours after the administration of the second amount of the recombinant polypeptide or the nucleic acid;
   e) administering a third amount of the recombinant polypeptide or the nucleic acid to the subject between 2-24 hours after the administration of the second amount of the agent to the subject; and
   f) administering a fourth amount of the recombinant polypeptide or the nucleic acid to the subject at least 20 hours after the administration of the third amount of the recombinant polypeptide or the nucleic acid to the subject.

4. The method of claim 3, wherein
the third amount of the recombinant polypeptide or the nucleic acid of e) is administered to the subject at about 3-4 hours after the administration of the second amount of the agent; and
the fourth amount of the recombinant polypeptide or the nucleic acid of f) is administered to the subject at least 24 hours after the administration of the third amount of the recombinant polypeptide or the nucleic acid.

5. The method of claim 3, further comprising:
   g) administering a third amount of the agent to the subject at least 24 hours after the administration of the fourth amount of the recombinant polypeptide or the nucleic acid;
   h) administering a fifth amount of the recombinant polypeptide or the nucleic acid between 2-24 hours after the administration of the third amount of the agent; and
   i) administering a sixth amount of the recombinant polypeptide or the nucleic acid to the subject at least 20 hours after the administration of the fifth amount of the recombinant polypeptide or the nucleic acid.

6. The method of claim 5, wherein
the fifth amount of a recombinant polypeptide or the nucleic acid of h) is administered to the subject at about 3-4 hours after the administration of the third amount of the agent; and the sixth amount of the recombinant polypeptide or the nucleic acid of i) is administered to the subject at least 24 hours after the administration of the fifth amount of the recombinant polypeptide or the nucleic acid.

7. The method of claim 3, wherein the third amount of the recombinant polypeptide or the nucleic acid is determined by:
   a) determining the constants a and b in the following system of equations:

$$CRP_1 = a \times Amount_1 + b$$
   $$CRP_2 - CRP_1/8 = a \times Amount_2 + b$$

wherein $CRP_1$ is the amount of C-Reactive Protein (CRP) in blood from the subject about 20 hours after the administration of the first amount of the recombinant polypeptide or the nucleic acid, $CRP_2$ is the amount of CRP in blood from the subject about 20 hours after the administration of the second amount of the recombinant polypeptide or the nucleic acid, $Amount_1$ is the first amount of the recombinant polypeptide or the nucleic acid and $Amount_2$ is the second amount of the recombinant polypeptide or the nucleic acid; and
   b) determining the third amount of the recombinant polypeptide or the nucleic acid, $Amount_3$, wherein $$Amount_3 = \frac{CRP^{Optimal1} - b}{a},$$

wherein $CRP^{Optimal1}$ is the intended optimal amount of CRP present in the blood of the subject after administration of the third amount of the recombinant polypeptide or the nucleic acid;
   wherein the $CRP_1$ and $CRP_2$ is measured in mg/L; and wherein the $CRP^{Optimal}$ is between about 170 mg/L to about 220 mg/L.

8. The method of claim 7, wherein the $CRP^{Optimal1}$ is between about 200 mg/L to about 220 mg/L.

9. The method of claim 3, wherein the fourth amount of the recombinant polypeptide or the nucleic acid is determined by:
   a) determining the constants a and b in the following system of equations:

$$CRP_1 = a \times Amount_1 + b$$
   $$CRP_1 = a \times Amount_1 + b$$
   $$CRP_2 - CRP_1/8 = a \times Amount_2 + b$$

wherein $CRP_1$ is the amount of CRP in blood from the subject about 20 hours after the administration of the first amount of the recombinant polypeptide or the nucleic acid, $CRP_2$ is the amount of CRP in blood from the subject about 20 hours after the administration of the second amount of the recombinant polypeptide or the nucleic acid, $Amount_1$ is the first amount of the recombinant polypeptide or the nucleic acid and $Amount_2$ is the second amount of the recombinant polypeptide or the nucleic acid;
   b) determining the fourth amount, $Amount_4$, wherein $$Amount_4 = \frac{(CRP^{Optimal2} - CRP^{Optimal1}/8) - b}{a};$$

wherein $CRP_1$ and $CRP_2$ is measured in mg/L; and wherein the $CRP^{Optimal2}$ is between about 130 mg/L to about 180 mg/L.

10. The method of claim 9, wherein the $CRP^{Optimal2}$ is between about 159 mg/mL to about 169 mg/mL.

11. The method of claim 5, wherein the fifth amount of the recombinant polypeptide or the nucleic acid is the same as the third amount of the recombinant polypeptide or the nucleic acid.

12. The method of claim 5, wherein the sixth amount of the recombinant polypeptide or the nucleic acid is the same as the fourth amount of the recombinant polypeptide or the nucleic acid.

13. The method of claim 5, wherein any of the first amount, the second amount or the third amount of the agent are administered via intravenous injection or intraperitoneal injection.

14. The method of claim 5, wherein any of the first amount, the second amount, the third amount, the fourth amount, the fifth amount or the sixth amount of the recombinant polypeptide or the nucleic acid are administered via intravenous injection or intraperitoneal injection.

15. The method of claim 1, wherein any of the first amount, the second amount or the third amount of the agent is selected based on the ratio: $IL\text{-}10_{subject}:IL\text{-}10_{healthy}$,
   wherein $IL\text{-}10_{subject}$ is the amount of IL-10 in serum from the subject prior to administration of any of the first amount, the third amount or the fifth amount of recombinant polypeptide or the nucleic acid and wherein $IL\text{-}10_{healthy}$ is the amount of IL-10 in serum from a healthy subject.

16. The method of claim 15, wherein any of the first amount, the second amount or the third amount of the agent is selected from: about 25 µg/m² when the ratio is between about 1.09 to about 1.13, about 50 µg/m² when the ratio is about 1.23 to about 1.27, about 75 µg/m² when the ratio is about 1.30 to about 1.35, about 100 µg/m² when the ratio is about 1.40 to about 1.45, about 150 µg/m² when the ratio is about 1.80 to about 1.85, about 300 µg/m² when the ratio is about 2.80 to about 2.90 or about 600 µg/m² when the ratio is about 7.10 to about 7.20.

17. The method of claim 1, wherein the first amount of recombinant polypeptide or the nucleic acid is effective to obtain an amount of C-Reactive Protein (CRP) in the blood from the subject of between about 170 mg/L to about 220 mg/L and wherein the first amount of the recombinant polypeptide is between about 18 mg/kg to about 22 mg/kg.

18. The method of claim 1, wherein the first amount of the recombinant polypeptide is about 20 mg/kg.

19. The method of claim 1, wherein the second amount of the recombinant polypeptide or the nucleic acid is effective to obtain an amount of CRP in the blood from the subject of between about 130 mg/L to about 180 mg/L and wherein the second amount of the recombinant polypeptide is between about 11 mg/kg to about 16 mg/kg.

20. The method of claim 1, wherein the second amount of the recombinant polypeptide is about 13.5 mg/kg.

21. The method of claim 1, wherein the recombinant polypeptide comprises an amino acid sequence of SEQ ID NO: 9 or a nucleic acid encoding the recombinant polypeptide comprising an amino acid sequence of SEQ ID NO: 9.

22. The method of claim 1, wherein the agent that reduces IL-10 is interferon gamma (IFNg), an IFNg mimetic, an IFNg agonist or a combination thereof.

23. The method of claim 22, wherein the agent that reduces IL-10 is IFNg.

24. The method of claim 1, wherein the cancer is a recurrence of an earlier presentation of cancer or is a metastasis of an earlier presentation of cancer.

25. The method of claim 1, wherein the cancer is a solid tumor cancer.

26. The method of claim 1, wherein any of the first amount, the second amount, or the third amount of the agent is selected based on the ratio: $IgG_{subject}:IgG_{healthy}$,
wherein $IgG_{subject}$ is the amount of IgG in serum from the subject prior to administration of the first amount, the third amount, or the fifth amount of recombinant polypeptide or the nucleic acid and wherein $IgG_{healthy}$ is the amount of IgG in serum from a healthy subject.

27. A method of treating cancer in a subject comprising:
a) administering a first amount of a recombinant polypeptide comprising an amino acid sequence having at least 99% sequence identity to the polypeptide of SEQ ID NO: 9 or a nucleic acid encoding the recombinant polypeptide comprising an amino acid sequence having at least 99% sequence identity to the polypeptide of SEQ ID NO: 9 to the subject; and
b) administering a second amount of the recombinant polypeptide or the nucleic acid to the subject at least 20 hours after the administration of the first amount of the recombinant polypeptide or the nucleic acid.

28. The method of claim 27, wherein the recombinant polypeptide comprises an amino acid sequence of SEQ ID NO: 9 or a nucleic acid encoding the recombinant polypeptide comprising an amino acid sequence of SEQ ID NO: 9.

* * * * *

UNITED STATES PATENT AND TRADEMARK OFFICE
CERTIFICATE OF CORRECTION

PATENT NO. : 10,675,332 B1
APPLICATION NO. : 16/551659
DATED : June 9, 2020
INVENTOR(S) : Ya-Huei Chen et al.

Page 1 of 1

It is certified that error appears in the above-identified patent and that said Letters Patent is hereby corrected as shown below:

In the Claims

At Column 121, Claim number 7, Line number 14:
"$CRP_2 - CRP_1/8 = a \times Amount_2 + b$"
Should read:
-- $CRP_2 - {}^{CRP_1}\!/_8 = a \times Amount_2 + b$ --

At Column 121, Claim number 7, Line number 40:
"wherein the $CRP^{Optimal}$ is between about 170 mg/L to"
Should read:
-- wherein the $CRP^{Optimal1}$ is between about 170 mg/L to --

At Column 121, Claim number 9, Line number 50-55:
"$CRP_1 = a \times Amount_1 + b$ $CRP_1 = a \times Amount_1 + b$
$CRP_2 - CRP_1/8 = a \times Amount_2 + b$"
Should read:
-- $CRP_1 = a \times Amount_1 + b$
$CRP_2 - {}^{CRP_1}\!/_8 = a \times Amount_2 + b$ --

At Column 122, Claim number 9, Line number 4:
" $Amount_4 = \dfrac{(CRP^{Optimal_2} - CRP^{Optimal_1}/8) - b}{a}$ ; "
Should read:
$Amount_4 = \dfrac{(CRP^{Optimal_2} - CRP^{Optimal_1}/8) - b}{a}$ ;
-- --

Signed and Sealed this
First Day of September, 2020

Andrei Iancu
*Director of the United States Patent and Trademark Office*